US012702797B2

(12) United States Patent
Pesce et al.

(10) Patent No.: US 12,702,797 B2
(45) Date of Patent: Aug. 11, 2026

(54) DELIVERY SYSTEM FOR A HEART VALVE SUPPORT DEVICE

(71) Applicant: TriFlo Cardiovascular Inc., Newport Beach, CA (US)

(72) Inventors: Luca Pesce, Huntington Beach, CA (US); Michael Nadolny, Santa Ana, CA (US); John Paul Ussia, Rome (IT); Christine Thanh Nguyen, Santa Ana, CA (US); Christine Thao Nguyen, Santa Ana, CA (US); Oladipo Akerele-Ale, Huntington Beach, CA (US); Hykaz Paronian, Costa Mesa, CA (US)

(73) Assignee: TriFlo Cardiovascular Inc., Newport Beach, CA (US)

( * ) Notice: Subject to any disclaimer, the term of this patent is extended or adjusted under 35 U.S.C. 154(b) by 964 days.

(21) Appl. No.: 17/649,329

(22) Filed: Jan. 28, 2022

(65) Prior Publication Data

US 2022/0395669 A1 Dec. 15, 2022

Related U.S. Application Data

(60) Provisional application No. 63/142,853, filed on Jan. 28, 2021.

(51) Int. Cl.
*A61F 2/24* (2006.01)
*A61M 25/01* (2006.01)

(52) U.S. Cl.
CPC ....... *A61M 25/0136* (2013.01); *A61F 2/2436* (2013.01); *A61M 25/0138* (2013.01); *A61M 25/0147* (2013.01)

(58) Field of Classification Search
CPC ...... A61F 2/2427; A61F 2/243; A61F 2/2439; A61F 2/2436
See application file for complete search history.

(56) References Cited

U.S. PATENT DOCUMENTS

| | | | |
|---|---|---|---|
| 5,954,766 | A | 9/1999 | Azizi et al. |
| 6,048,189 | A | 4/2000 | Kurihara et al. |
| 6,569,198 | B1 | 5/2003 | Wilson et al. |
| 6,764,510 | B2 | 7/2004 | Vidlund et al. |

(Continued)

FOREIGN PATENT DOCUMENTS

| | | | |
|---|---|---|---|
| CN | 102781371 | A | 11/2012 |
| CN | 104220027 | A | 12/2014 |

(Continued)

OTHER PUBLICATIONS

Pesce et al.; U.S. Appl. No. 18/335,600 entitled "Heart valve support device," filed Jun. 15, 2023.

*Primary Examiner* — Alvin J Stewart
(74) *Attorney, Agent, or Firm* — Shay Glenn LLP

(57) ABSTRACT

Devices for assisting with the functioning of a tricuspid valve of a heart include a shaft, a flow optimizer, and an anchoring mechanism. A tilting mechanism can be configured to tilt the shaft relative to a central axis of the anchoring mechanism. Leaflets (e.g., multi-layer leaflets) of the flow optimizer can include a membrane and a rim, and the rim can have a higher stiffness than the membrane. A delivery system can be configured to deliver the device and adjust the position of the flow optimizer with respect to the anchoring mechanism.

9 Claims, 85 Drawing Sheets

(56) References Cited

U.S. PATENT DOCUMENTS 6,797,002 B2 9/2004 Spence et al.
6,848,440 B2 2/2005 Han et al.
7,611,534 B2 11/2009 Kapadia et al.
7,704,277 B2 4/2010 Zakay et al.
7,789,909 B2 9/2010 Andersen et al.
7,854,762 B2 12/2010 Speziali et al.
7,901,454 B2 3/2011 Kapadia et al.
8,092,525 B2 1/2012 Eliasen et al.
8,109,996 B2 2/2012 Stacchino et al.
8,377,115 B2 2/2013 Thompson
8,408,214 B2 4/2013 Spenser
8,449,599 B2 5/2013 Chau et al.
8,470,028 B2 6/2013 Thornton et al.
8,475,525 B2 7/2013 Maisano et al.
8,597,347 B2 12/2013 Maurer et al.
8,641,757 B2 2/2014 Pintor et al.
8,778,017 B2 7/2014 Eliasen et al.
8,932,348 B2 1/2015 Solem et al.
8,961,596 B2 2/2015 Maisano et al.
9,011,523 B2 4/2015 Seguin
9,161,837 B2 10/2015 Kapadia
9,232,998 B2 1/2016 Wilson et al.
9,232,999 B2 1/2016 Maurer et al.
9,241,702 B2 1/2016 Maisano et al.
9,307,980 B2 4/2016 Gilmore et al.
9,414,918 B2 8/2016 Chau et al.
9,474,605 B2 10/2016 Rowe et al.
9,504,570 B2 11/2016 Hauser et al.
9,629,720 B2 4/2017 Nguyen et al.
9,636,223 B2 5/2017 Khalil et al.
9,750,604 B2 9/2017 Naor
9,827,099 B2 11/2017 Mathis et al.
10,136,993 B1 11/2018 Metchik et al.
10,195,033 B2 2/2019 Tuval et al.
10,231,837 B1 3/2019 Metchik et al.
10,238,490 B2 3/2019 Gifford
10,238,493 B1 3/2019 Metchik et al.
10,327,743 B2 6/2019 St. Goar et al.
10,413,402 B2 9/2019 Squara
10,420,565 B2 9/2019 Garcia et al.
10,524,913 B2 1/2020 Delgado et al.
10,595,997 B2 3/2020 Metchik et al.
10,765,518 B2 9/2020 Pesce
10,779,829 B2 9/2020 Wei
10,779,837 B2 9/2020 Lee et al.
10,799,360 B2 10/2020 Kapadia
10,813,760 B2 10/2020 Metchik et al.
10,842,626 B2 11/2020 de Canniere
10,842,628 B1 * 11/2020 Pesce .................... A61F 2/246
10,856,858 B2 12/2020 Thambar et al.
10,888,424 B2 1/2021 Kuetting et al.
10,912,644 B2 2/2021 Argento et al.
10,945,718 B2 3/2021 Hiorth et al.
10,966,823 B2 4/2021 Suri et al.
10,980,632 B2 4/2021 Burriesci et al.
11,000,372 B2 5/2021 Khairkhahan et al.
11,007,060 B2 5/2021 He et al.
11,007,061 B2 5/2021 Passman et al.
11,020,221 B2 6/2021 Arcaro et al.
11,026,785 B2 * 6/2021 Barash .................. A61F 2/2415
11,045,311 B2 6/2021 Vaturi et al.
11,058,535 B2 7/2021 Noe et al.
11,090,158 B2 8/2021 Noe et al.
11,547,564 B2 1/2023 Metchik et al.
11,576,781 B2 2/2023 Kim
11,602,431 B2 3/2023 Delgado et al.
11,717,406 B2 * 8/2023 Pesce .................... A61F 2/246
623/2.1
11,801,140 B2 10/2023 Abunassar
11,826,249 B2 11/2023 Morriss et al.
11,833,038 B2 12/2023 Kovalsky et al.
11,849,937 B2 12/2023 Darabian
11,850,153 B2 12/2023 Delgado et al.
11,864,995 B2 1/2024 Gross et al.
11,883,291 B2 1/2024 Gifford, III et al.
11,903,832 B2 2/2024 Feld
11,925,558 B2 3/2024 Kim et al.
11,957,585 B2 4/2024 Wang et al.
11,957,586 B2 4/2024 Anderson et al.
11,969,346 B2 4/2024 Cao
11,974,921 B2 5/2024 Khairkhahan et al.
12,029,425 B2 7/2024 Ketai et al.
12,042,379 B2 7/2024 Kim et al.
12,053,373 B2 8/2024 McLean et al.
12,138,167 B2 11/2024 Yeo et al.
12,150,856 B2 11/2024 Khairkhahan et al.
12,156,813 B2 12/2024 Karapetian et al.
12,161,554 B2 12/2024 Delgado et al.
12,186,191 B2 1/2025 Delgado et al.
12,239,532 B2 3/2025 Seguin
12,245,942 B2 3/2025 Siegel et al.
12,251,309 B2 3/2025 Freschauf et al.
12,285,336 B2 4/2025 Khairkhahan
12,295,845 B2 5/2025 Khairkhahan et al.
12,383,400 B2 * 8/2025 Valdez .................. A61F 2/2436
2002/0077696 A1 6/2002 Azizi et al.
2002/0095209 A1 7/2002 Azizi et al.
2004/0260317 A1 12/2004 Bloom et al.
2005/0070999 A1 3/2005 Spence
2006/0178700 A1 8/2006 Quinn
2006/0241745 A1 10/2006 Solem
2007/0185571 A1 8/2007 Kapadia et al.
2007/0203391 A1 8/2007 Bloom et al.
2007/0282429 A1 12/2007 Hauser et al.
2007/0293943 A1 12/2007 Quinn
2008/0033541 A1 2/2008 Gelbart et al.
2009/0222081 A1 9/2009 Linder et al.
2010/0298929 A1 11/2010 Thornton et al.
2011/0022164 A1 1/2011 Quinn et al.
2011/0054598 A1 3/2011 Johnson
2011/0077733 A1 3/2011 Solem
2013/0238089 A1 9/2013 Lichtenstein et al.
2014/0031928 A1 1/2014 Murphy et al.
2014/0067048 A1 3/2014 Chau et al.
2014/0114390 A1 4/2014 Tobis et al.
2014/0163652 A1 6/2014 Witzel et al.
2015/0100116 A1 4/2015 Mohl et al.
2015/0134057 A1 5/2015 Rourke et al.
2015/0173896 A1 6/2015 Richter et al.
2015/0257885 A1 9/2015 McGuckin
2015/0327971 A1 11/2015 Mujwid et al.
2016/0030169 A1 2/2016 Shahriari
2016/0089238 A1 3/2016 Centola et al.
2016/0113766 A1 4/2016 Ganesan et al.
2016/0166382 A1 6/2016 Nguyen
2016/0199181 A1 7/2016 Kramer
2016/0331523 A1 11/2016 Chau et al.
2016/0367367 A1 12/2016 Maisano et al.
2017/0056176 A1 3/2017 Rowe et al.
2017/0079797 A1 3/2017 Maisano et al.
2017/0112618 A1 4/2017 Li et al.
2017/0239041 A1 8/2017 Quinn
2017/0258589 A1 9/2017 Pham et al.
2018/0036119 A1 2/2018 Wei et al.
2018/0078361 A1 3/2018 Naor et al.
2018/0168803 A1 * 6/2018 Pesce .................... A61F 2/2409
2018/0207336 A1 7/2018 Solem
2018/0311037 A1 11/2018 Morriss et al.
2019/0000618 A1 1/2019 Schweich et al.
2019/0060072 A1 2/2019 Zeng
2019/0069997 A1 3/2019 Ratz et al.
2019/0083262 A1 3/2019 Hariton et al.
2019/0201190 A1 7/2019 Dakin et al.
2019/0314155 A1 10/2019 Franklin et al.
2019/0343629 A1 11/2019 Solem
2020/0000592 A1 1/2020 Lee et al.
2020/0060818 A1 2/2020 Geist et al.
2020/0069419 A1 3/2020 Lee et al.
2020/0113679 A1 4/2020 Pesce et al.
2020/0138570 A1 5/2020 Biadillah et al.
2020/0205966 A1 7/2020 Khairkhahan et al.
2020/0222185 A1 7/2020 Kappetein et al.
2020/0237512 A1 7/2020 McCann et al.
2020/0261220 A1 8/2020 Argento et al.

(56) References Cited

U.S. PATENT DOCUMENTS

| | | | |
|---|---|---|---|
| 2020/0323616 | A1 | 10/2020 | Lashinski et al. |
| 2020/0337843 | A1 | 10/2020 | Khairkhahan et al. |
| 2020/0352707 | A1 | 11/2020 | Gifford |
| 2020/0367871 | A1 | 11/2020 | Van Hoven et al. |
| 2021/0022851 | A1 | 1/2021 | Pesce et al. |
| 2021/0022860 | A1 | 1/2021 | Lally et al. |
| 2021/0022864 | A1 | 1/2021 | Machold et al. |
| 2021/0030534 | A1 | 2/2021 | Siegel et al. |
| 2021/0038377 | A1 | 2/2021 | Pesce et al. |
| 2021/0038378 | A1 | 2/2021 | Sutherland et al. |
| 2021/0068950 | A1 | 3/2021 | Quill et al. |
| 2021/0085451 | A1 | 3/2021 | Kim |
| 2021/0128298 | A1 | 5/2021 | Rengarajan et al. |
| 2021/0154011 | A1 | 5/2021 | Christianson et al. |
| 2021/0161668 | A1* | 6/2021 | Metchik ................ A61F 2/2463 |
| 2023/0000619 | A1 | 1/2023 | Vidlund et al. |
| 2023/0346556 | A1 | 11/2023 | Metchik et al. |
| 2023/0355391 | A1 | 11/2023 | Basude et al. |
| 2024/0016607 | A1 | 1/2024 | Abunassar |
| 2024/0033083 | A1 | 2/2024 | Khairkhahan |
| 2024/0033085 | A1 | 2/2024 | Wu et al. |
| 2024/0041601 | A1 | 2/2024 | Khairkhahan et al. |
| 2024/0050228 | A1 | 2/2024 | Dixon et al. |
| 2024/0058128 | A1* | 2/2024 | Pesce ...................... A61F 2/246 |
| 2024/0065837 | A1 | 2/2024 | Hoffer et al. |
| 2024/0091010 | A1 | 3/2024 | Zheng et al. |
| 2024/0122709 | A1 | 4/2024 | Freschauf et al. |
| 2024/0148507 | A1 | 5/2024 | Scheinblum et al. |
| 2024/0156598 | A1 | 5/2024 | Oliver et al. |
| 2024/0164905 | A1 | 5/2024 | Herman et al. |
| 2024/0197473 | A1 | 6/2024 | Chau |
| 2024/0197475 | A1 | 6/2024 | Salsac et al. |
| 2024/0225837 | A1 | 7/2024 | Martin et al. |
| 2024/0238091 | A1 | 7/2024 | Duffy et al. |
| 2024/0245512 | A1 | 7/2024 | Padala et al. |
| 2024/0277468 | A1 | 8/2024 | Siegel et al. |
| 2024/0277476 | A1 | 8/2024 | Dixon et al. |
| 2024/0299034 | A1 | 9/2024 | Coleman et al. |
| 2024/0299169 | A1 | 9/2024 | Oberwise et al. |
| 2024/0299170 | A1 | 9/2024 | Gabbay |
| 2024/0307184 | A1 | 9/2024 | Edwards et al. |
| 2024/0335287 | A1 | 10/2024 | Chau et al. |
| 2025/0000652 | A1 | 1/2025 | Basude et al. |
| 2025/0090306 | A1 | 3/2025 | Keränen |
| 2025/0090325 | A1 | 3/2025 | Navia et al. |
| 2025/0143703 | A1 | 5/2025 | Hernandez et al. |
| 2025/0152357 | A1 | 5/2025 | Zeng |
| 2025/0152358 | A1 | 5/2025 | Yaron et al. |

FOREIGN PATENT DOCUMENTS

| | | | |
|---|---|---|---|
| CN | 104994811 | A | 10/2015 |
| CN | 105188599 | A | 12/2015 |
| CN | 109310500 | A | 2/2019 |
| CN | 110290764 | A | 9/2019 |
| WO | WO2005/027797 | A1 | 3/2005 |
| WO | WO2008/141325 | A1 | 11/2008 |
| WO | WO2013/173587 | A1 | 11/2013 |
| WO | WO2016/180529 | A1 | 11/2016 |
| WO | WO2018/042439 | A1 | 3/2018 |
| WO | WO2018/145055 | A1 | 8/2018 |
| WO | WO2018/232026 | A1 | 12/2018 |
| WO | WO2019/010370 | A1 | 1/2019 |
| WO | WO2019/157331 | A1 | 8/2019 |
| WO | WO2020/117888 | A1 | 6/2020 |
| WO | WO2020/167677 | A1 | 8/2020 |
| WO | WO2020/176310 | A1 | 9/2020 |
| WO | WO2020/197854 | A1 | 10/2020 |
| WO | WO2020/231237 | A2 | 11/2020 |
| WO | WO2020/236417 | A1 | 11/2020 |
| WO | WO2020/236735 | A1 | 11/2020 |
| WO | WO2021/055983 | A1 | 3/2021 |
| WO | WO2021/067043 | A1 | 4/2021 |
| WO | WO2021/076555 | A1 | 4/2021 |
| WO | WO2021/111451 | A1 | 6/2021 |
| WO | WO2023/004098 | A1 | 1/2023 |
| WO | WO2023/015601 | A1 | 2/2023 |

* cited by examiner

Note: Arm 515a removed for clarity

500

Note: Cross-section

Note: Cross-section

500

Note: Cross-section

500

Note: Leaflets 550 removed for clarity

Note: Leaflets 550 removed for clarity 700
719
779
771
721
710
775
715a
722c
777
773
779
740
715c 700
719
779
721
771
775
740
715a
722c
777
773
779
740
715c

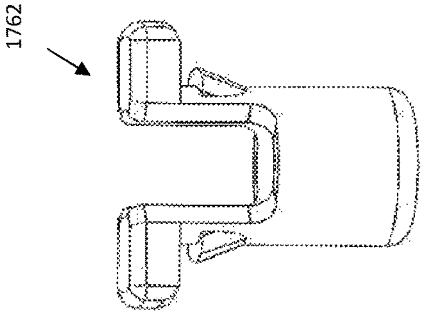
FIG. 17E
FIG. 17B
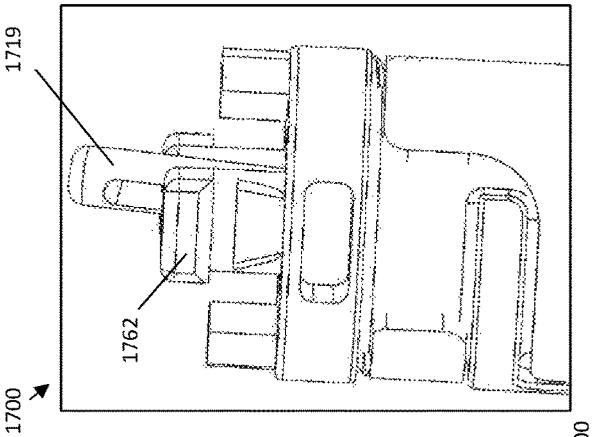
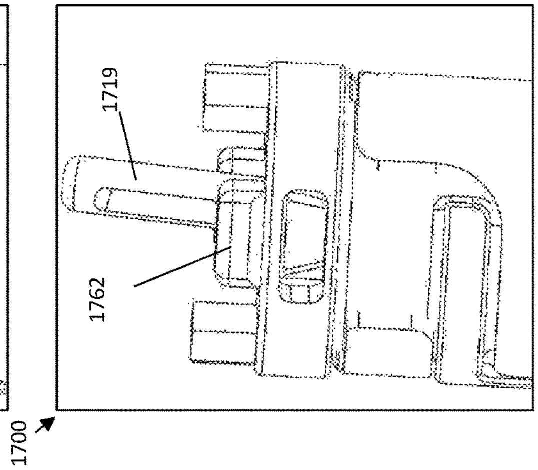
FIG. 17D
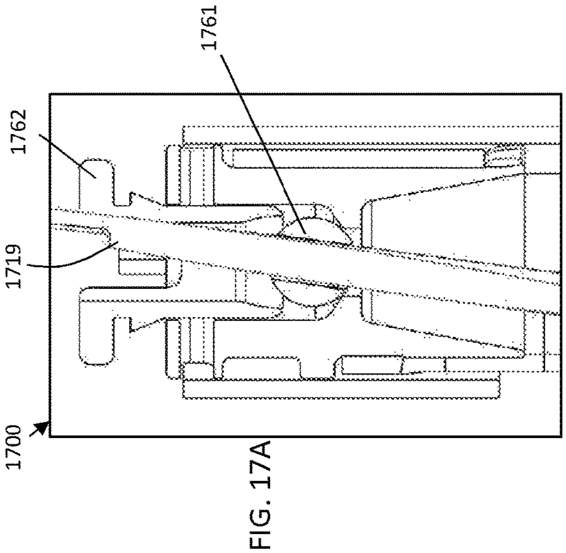
FIG. 17A
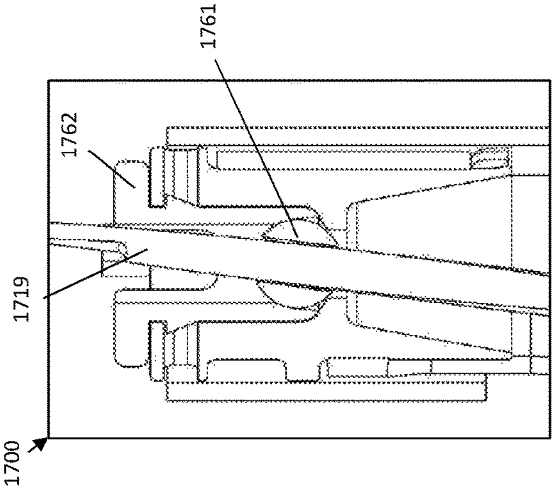
FIG. 17C

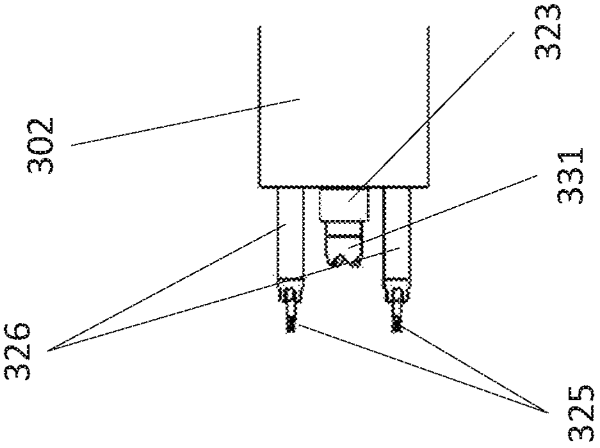
FIG. 23C
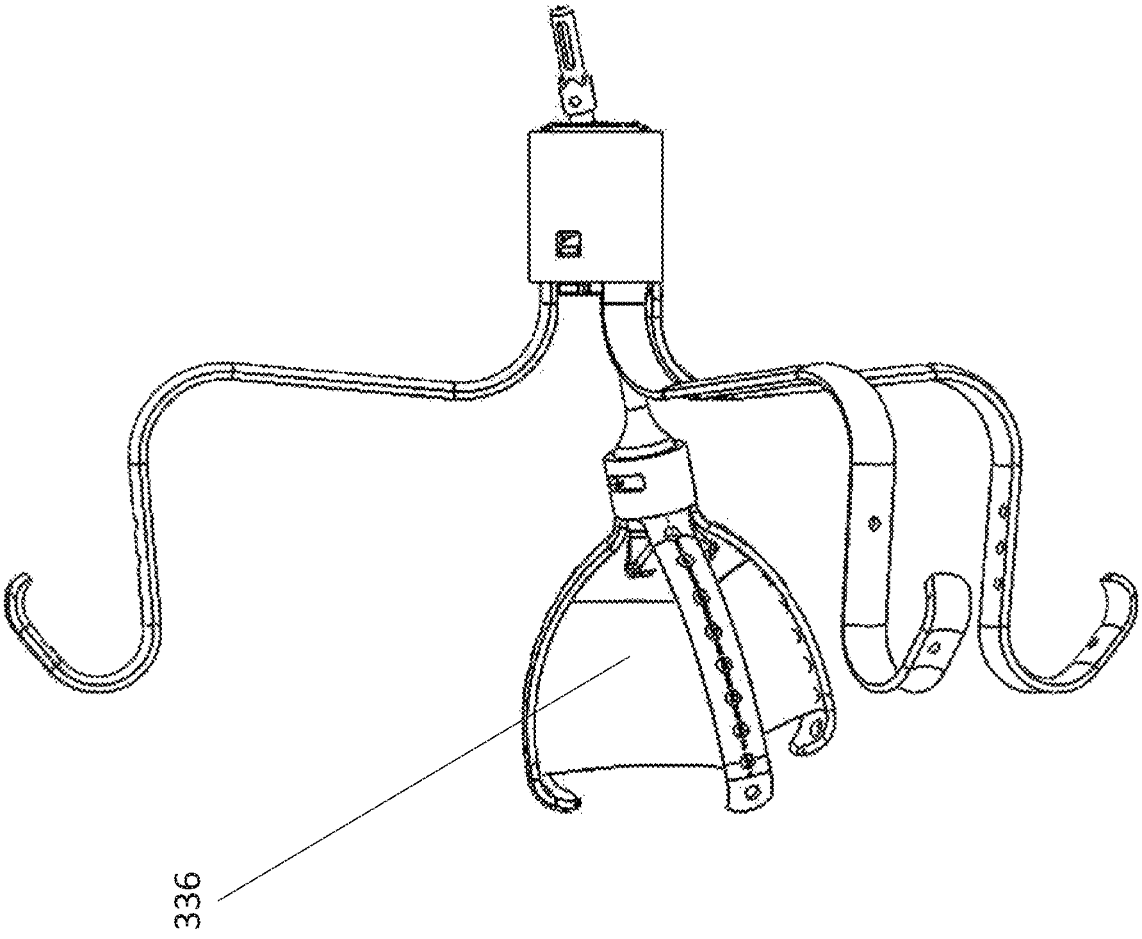

1916
351
1920
325
329
352
326
3930
3938
3934
4004
4003
331
1918
328
4204
1924
311
314
306
338
4001
336
3602
1925
354
353
344
356
356

DELIVERY SYSTEM FOR A HEART VALVE SUPPORT DEVICE

CROSS REFERENCE TO RELATED APPLICATIONS

This application claims the benefit of U.S. Provisional Application No. 63/142,853, filed Jan. 28, 2021, titled "Heart Valve Support Device".

The application may be related to U.S. application Ser. No. 16/882,226, filed May 22, 2020, now U.S. Pat. No. 10,842,628, U.S. Provisional Application No. 62/851,503, titled "Heart Valve Support Device," filed on May 22, 2019, and U.S. Provisional Application No. 62/976,232, titled "Heart Valve Support Device," filed on Feb. 13, 2020, the entireties of which are incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

The tricuspid valve (TV) is an atrioventricular valve located in the right side of the human heart between the right atrium (RA) and the right ventricle (RV). The TV includes three asymmetrical leaflets (septal, anterior, and posterior) supported by a complex sub-valvular apparatus that includes the chordae tendineae and the papillary muscles. The TV is also in proximity to the tendon of Todaro, where the heart's delicate atrioventricular node is located.

Regurgitant flow occurs during the systolic phases of the cardiac cycle when the tricuspid valve becomes incompetent. The incompetence is often caused by the pathology-induced progressive enlargement of the valve's annulus, which prevents the leaflets from reaching full coaptation during systole (or during the systole phase of the cardiac cycle). The lack of coaptation can cause the development of a regurgitant orifice within the valve, through which blood can reenter the right atrium instead of exiting the right ventricle via the pulmonary valve. This condition can induce a cardiac overload with subsequent enlargement of the right ventricle and the right atrium, reduction of the right ventricular stroke volume, increase in systemic vein congestion, and other symptoms of congestive heart failure. Tricuspid valve regurgitation can be isolated from or associated with other valvulopathies and can lead to congestive heart failure, reduced functional cardiovascular capacity, and increased risks of untimely mortality.

Surgical repair or replacement are the most commonly used techniques for treating tricuspid valve regurgitation, but the clinical results (e.g. mortality and recurrence) are suboptimal. Moreover, due to the common presence of several comorbidities in patients affected by tricuspid regurgitation, the majority of patients are ineligible for surgical repair or replacement because of the high risk correlated with those procedures.

Transcatheter therapy does not require open-heart surgery and could be a viable and safer alternative. The unique anatomical features of the tricuspid valve, however, are a significant challenge for developing a safe and effective transcatheter implant. For example, anchoring the implant in the tricuspid valve may require burdening the adjacent cardiac structure (e.g. superior or inferior vena cava, the atrioventricular node, the coronary sinus, the right coronary artery, or the ventricular myocardium). Additionally, the low pressure and output of the hemodynamic flow at the tricuspid valve in the right side of the heart increases the risks of inducing atrioventricular pressure gradient and thrombogenesis. Accordingly, a transcatheter tricuspid valve implant that overcomes some or all of these challenges is desired.

SUMMARY OF THE DISCLOSURE

In a first aspect, a delivery system for adjusting a device for assisting with functioning of a valve of a heart is provided. The system comprises a steerable catheter control section comprising a steerable catheter configured to navigate through the vasculature to the tricuspid valve; and controls configured to control navigation of the steerable catheter through the vasculature to the tricuspid valve; and an implant delivery catheter control section comprising a delivery catheter configured to navigate through the steerable catheter and configured to allow passage of the device comprising a device shaft; a flow optimizer fixedly connected to a distal end region of the device shaft; and a plurality of anchoring arms connected to a proximal region of the device shaft; a shaft positioned within the delivery catheter and configured to move relative to the delivery catheter, wherein translation of the shaft relative to the delivery catheter is configured to expose the device from within the delivery catheter; a flexible member extending through the delivery catheter and configured to butt up against a proximal portion of the device shaft, wherein manipulation of the wherein a distal portion of the flexible member is configured to interact with a proximal end of the device shaft, and wherein rotation and translation of the flexible member is configured to cause rotation and translation of the device shaft, thereby adjusting a position of the flow optimizer relative to the anchoring arms.

In another aspect, a delivery system for adjusting a device for assisting with functioning of a valve of a heart is provided. The system comprises a delivery catheter configured to navigate through the vasculature and configured to allow passage of the device comprising a device shaft; a flow optimizer fixedly connected to a distal end region of the device shaft; and a plurality of anchoring arms connected to a proximal region of the device shaft; a shaft positioned within the delivery catheter and configured to move relative to the delivery catheter, wherein translation of the shaft relative to the delivery catheter is configured to expose the device from within the delivery catheter; a flexible member extending through the delivery catheter and configured to butt up against a proximal portion of the device shaft, wherein a distal portion of the flexible member is configured to interact with a proximal end of the device shaft, and wherein rotation and translation of the flexible member is configured to cause rotation and translation of the device shaft, thereby adjusting a position of the flow optimizer relative to the anchoring arms.

In some embodiments, the system comprises an adjustment member extending through the delivery shaft and over the flexible member, a distal portion of the adjustment member biased to be bent, the adjustment member able to move from a straighter configuration when positioned in the delivery shaft to a more bent configuration when at least a portion of the adjustment member is positioned out of the shaft. The adjustment member can be configured to bend the flexible member when it is in its more bent configuration out of the shaft. In some embodiments, the flexible member, when bent, is configured to tilt a flow optimizer of the device relative to an anchoring mechanism of the device. The adjustment member can be configured to rotate, wherein rotation of the adjustment member changes an orientation of the flexible member. In some embodiments, the system comprises an adjustment member control section comprising a knob controlling axial translation of the adjustment member. The system can comprise an adjustment member control section comprising a knob controlling rotation of the adjustment member.

In some embodiments, the system comprises a steerable catheter through which the delivery catheter extends. The system can comprise one or more pull wires configured to control deflection of the catheter. The steerable catheter can comprise comprises a distal section comprising a distal portion configured to deflect up to 180 degrees; a midportion proximal to the distal portion configured to deflect up to 60 degrees; and a proximal portion proximal to the midportion configured to bilaterally deflect up to 45 degrees. In some embodiments, the steerable catheter comprises an atraumatic distal tip. The steerable catheter can comprise a distal surface that tapers towards a longitudinal axis of the steerable catheter.

The system can comprise a first control for the distal portion, a second control for the midportion, and a third control for the proximal portion. In some embodiments, the distal portion comprises a first cut pattern, the midportion comprises a second cut pattern, and the proximal portion comprises a third cut pattern, and wherein the first, second, and third cut patterns are all different.

The system can comprise a hemostasis hub configured to allow aspiration of a delivery catheter positioned within the steerable catheter without any fluid loss.

In some embodiments, the system comprises one or more screw torqueing tubes configured to screw fasteners into a joint to lock a position of the device. The system can comprise one or more screw torqueing tubes configured to screw fasteners into a ball joint to lock a position of a shaft of the device relative to an anchoring mechanism of the device. In some embodiments, the system comprises one or more screw guidewires connected to the fasteners and over which the screw torqueing tubes extend. The torqueing tubes can comprise a rigid tube near a proximal end of the torqueing tubes. In some embodiments, the torqueing tubes comprise a knob at a proximal end of the torqueing tubes.

The system can comprise a tensioning wire extending through the handle and connected to a proximal end of a shaft of the device. The wire can be looped through the shaft of the device. The system can comprise a spool around which the wire can be tensioned.

In some embodiments, the system comprises a flexible member control section comprising a knob controlling axial translation of the flexible member. The system can comprise a flexible member control section comprising a knob controlling rotation of the flexible member.

The system can comprise a hemostasis valve near a proximal end of the adjustment member. In some embodiments, the system comprises a hemostasis valve near a proximal end of the flexible member.

The system can comprise a sealing block comprising a plurality of lumens configured to correspond to the plurality of lumens of the delivery shaft, the sealing block comprising a seal overlapping the adjustment member and an injection port.

In some embodiments, the system comprises a sliding platform configured to hold the handle. The system can comprise a first sliding platform for holding a portion of the handle fixed to the delivery shaft and a second sliding platform for holding a portion of the handle fixed to a catheter through which the delivery shaft extends. Each sliding platform can be configured to be locked in position. In some embodiments, each sliding platform comprises a standoff comprising a cutout configured to mate with a reciprocating cutout on the handle.

The system can comprise a rail upon which various components of the handle are positioned, the various components comprising a lead screw extending through the various components, wherein the lead screw is configured to be used to translate the various components along the rail. In some embodiments, the various components comprise an engager configured to allow engagement or disengagement of the component to the lead screw. The various components can comprise a clamp configured to clamp or release a positioned of the component with respect to the rail.

In some embodiments, a distal end of the delivery shaft comprises one or more steps configured to stagger the release of arms of the device.

The system can comprise an arm loop extending through the shaft to a distal portion of a loop shaft positioned within the shaft, the distal portion of the loops shaft configured to be positioned around height of the anchoring arms of the device an arm of the device, the arm loop looped secured to the arm and returning to a loop control portion of the delivery system. The arm loop can be configured to control expansion and contraction of the arm. In some embodiments, the system comprises a knob connected to the arm loop and configured to control tightening or loosening of the arm loop. The loop shaft can comprise an aperture allowing egress of the arm loop. In some embodiments, the loop shaft comprises a wire extending along the loop shaft and around which the loops are looped. The system can comprise an enlarged diameter portion of the wire at its distal end, the enlarged diameter portion having a greater diameter than a distal opening of the loop shaft. The enlarged diameter portion can comprise a coiled portion.

In some embodiments, the system comprises a tilt member extending distally through the delivery shaft to a rotation member connected to a proximal portion of the shaft, the tilt member looping through one or more apertures on the rotation member, free ends of the tilt member connected to one or more controls on the delivery system, wherein tensioning and loosening of the tilt member results in tilting of the rotation member. The tilt member can comprise a wire. In some embodiments, the shaft comprises two tilt members looped through the rotation member. The tilt member can be threaded through the rotation member such that it enters and exits the rotation member at least two times.

In yet another aspect, a method for positioning a device for assisting with functioning of a valve of a heart is provided. The method comprises advancing a flexible member through a delivery shaft until it butts up against a shaft of the device; axially translating the flexible member, to adjust a height of a flow optimizer fixed to the shaft relative to an anchoring assembly of the device; and fixing the shaft to the anchoring assembly, thereby fixing the position of the flow optimizer relative to the shaft.

In some embodiments, the method comprises rotating the flexible member to adjust a rotational position of the flow optimizer relative to the anchoring assembly of the device. The method can comprise tilting the flexible member to adjust a tile of the flow optimizer relative to the anchoring assembly of the device.

In some embodiments, adjusting a tilt comprises advancing a tilt adjustment member comprising a bend near its distal end over the flexible member and through the delivery shaft such that at least a portion of the tilt adjustment member advances past a distal end of the delivery shaft, thereby causing the portion to move from a straightened configuration to a bent configuration and causing a bend in the flexible member and causing the flow optimizer to tilt relative to the anchoring assembly. The method can comprise rotating the tilt adjustment member, thereby rotating the flow optimizer relative to the anchoring assembly. In some embodiments, the method comprises adjusting the portion of the tilt adjustment member advanced past the distal end of the delivery shaft, thereby adjusting a degree of tilt of the flow optimizer.

Adjusting the tilt can comprise adjusting tensioning on tilt members extending through the delivery shaft and threading through a rotation member at an end of the delivery shaft, thereby causing rotation of the rotation member and tilting of the flexible member extending through a lumen in the rotation member.

In some embodiments, fixing the shaft to the anchoring assembly comprises screwing a fastener into a ball joint connecting the anchoring assembly to the shaft. Screwing the fastener can comprise advancing a torqueing tube through the delivery shaft and to the fastener. In some embodiments, advancing the torqueing tube is done over a guidewire. The method can comprise locking the torqueing tube to the fastener. In some embodiments, the method comprises engaging the torqueing tube to the fastener using an interference fit. The method can comprise locking the torqueing tube to the fastener by advancing an outer member over the engaged torqueing tube and fastener. In some embodiments, the method comprises retracting the torqueing tube and guidewire after screwing the fastener.

The method can comprise removing a wire connecting the delivery system to the device after confirming proper positioning of the device. In some embodiments, removing the wire comprises unlooping the wire from the shaft of the device.

In some embodiments, the advancing and/or the axially translating is performed using a lead screw. In some embodiments, the advancing and/or the axially translating comprises sliding one or more components along a rail.

The method can comprise retracting the delivery shaft to expose arms of the device. In some embodiments, the delivery shaft comprises a distal end, and further comprising retracting the delivery shaft to expose arms of the device in a staggered manner.

The method can comprise expanding an arm of the device by loosening an arm loop, the arm loop extending through the handle to the device, looping around the arm, and returning to the handle. In some embodiments, the method comprises contracting an arm of the device by tightening an arm loop, the arm loop extending through the handle to the device, looping around the arm, and returning to the handle. Adjusting an arm loop can comprise turning a knob on the handle.

The method can comprise navigating a steerable catheter through the catheter, the steerable catheter having a distal section comprising a distal portion, a midportion, and a proximal portion. In some embodiments, the method comprises deflecting the distal portion in a first direction and amount, the midportion in a second direction and amount, and the proximal portion in a third direction and amount, wherein the first, second, and third directions and amounts are different from one another.

In another aspect, a device for adjusting anchoring arms of a device for supporting a heart valve is provided. The device comprises a base; a circular groove in the base, the circular groove comprising angle markings; and a plurality of sliders positioned within the groove and configured to slide within the groove, each slider comprising a slot configured to receive a portion of an anchoring arm.

In a further aspect, a method for preoperatively adjusting anchoring arms of a device for support a heart valve is provided. The method comprises placing arms of the device within openings on sliders of an alignment device; and sliding the sliders around a circular groove of the device until the sliders line up with predetermined arm angles using markings of the device.

In yet another aspect, a delivery system for adjusting a device for assisting with functioning of a valve of a heart is provided. The system comprises a delivery shaft comprising a plurality of lumens; a tilt member extending through the delivery shaft to a rotation member positioned near a distal end of the delivery shaft; the tilt member looping through one or more apertures on the rotation member and extending, free ends of the tilt member connected to one or more controls on the handle, wherein tensioning and loosening of the tilt member results in tilting of the rotation member.

The tilt member can comprise a wire. The shaft can comprise two tilt members looped through the rotation member. In some embodiments, the tilt member is threaded through the rotation member such that it enters and exits the ball at least two times. The tilt member can be threaded through the rotation member in such a manner that frictional force secures the relative position of the tilt member and the ball. The rotation member can comprise a lumen allowing passage of a flexible member therethrough, wherein tilting of the rotation member results in tilting of the flexible and thereby tilting of a device shaft, when the device shaft is interacting with the flexible member.

In another aspect, a delivery system for adjusting a device for assisting with functioning of a valve of a heart is provided. The system comprises a delivery shaft; a plurality of loops extending distally along the delivery shaft and configured to be secured to arms of the device, a proximal end of each loop connected to a control knob on the handle, wherein manipulation of the control knob is configured to cause tensioning or loosening of the loop, thereby causing expansion or contraction of the arm to which the loop is secured.

The loops can be configured to extend along a loop shaft positioned within the delivery shaft. The system can comprise a wire extending along the loop shaft and around which the loops are looped. In some embodiments, the system comprises an enlarged diameter portion of the wire at its distal end, the enlarged diameter portion having a greater diameter than a distal opening of the loop shaft. The enlarged diameter portion can comprise a coiled portion. IN some embodiments, each loop exits the handle through a loop port and is directed to its corresponding control knob. The loop control knobs can be arranged in a configuration to mimic the configuration of their corresponding device arms.

In another aspect, a steerable catheter for use in delivering a heart valve support device is provided. The steerable catheter comprises a distal section of the steerable catheter comprising a distal portion configured to deflect up to 180 degrees; a midportion proximal to the distal portion configured to deflect up to 90 degrees; and a proximal portion proximal to the midportion configured to bilaterally deflect up to 90 degrees.

In some embodiments, the midportion is configured to deflect up to 60 degrees and the proximal portion is configured to bilaterally deflect up to 45 degrees. The steerable catheter can comprise an atraumatic distal tip. In some embodiments, the atraumatic tip comprises a distal surface that tapers towards a longitudinal axis of the steerable catheter. The steerable catheter can comprise a first control for the distal portion, a second control for the midportion, and a third control for the proximal portion. In some embodiments, the distal portion comprises a first cut pattern, the midportion comprises a second cut pattern, and the proximal portion comprises a third cut pattern, and wherein the first, second, and third cut patterns are all different. The steerable catheter can comprise a hemostasis hub configured to allow aspiration of a delivery catheter positioned within the steerable catheter without any fluid loss. In some embodiments, the distal portion, the midportion, and the proximal portion are configured to enable navigation of the steerable catheter to a tricuspid valve of a patient.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 17A is a cross-sectional view of the proximal end of a valve support device with an annular lock in a proximal (unlocked) configuration.

FIG. 17B is a perspective view of the valve support device of FIG. 17A with the annular lock in the proximal configuration.

FIG. 17C is a cross-sectional view of the valve support device of FIG. 17A with the annular lock in the distal (locked) configuration.

FIG. 17D is a perspective view of the valve support device of FIG. 17A with the annular lock in the distal configuration.

FIG. 17E is a perspective view of the annular lock of the device of FIG. 17A.

FIG. 23C shows a top view of the device of FIGS. 18A and 18B after removal of the wire of FIG. 23B.

FIGS. 45A-45D show various views of an embodiment of an adjustment member control section.

DETAILED DESCRIPTION

Described herein are catheter-delivered intracardiac implants for supporting and improving the function of the tricuspid valve. The tricuspid valve implants (also called tricuspid valve support devices) can include a flow optimizer and/or an anchor, either or both of which can be configured to accommodate the anatomically and hemodynamically challenging location within the tricuspid valve. The flow optimizer, for example, can be configured such that, during the diastolic phase of the cardiac cycle, it minimizes its cross-sectional area and allows hemodynamic flow around and through the implant, thus minimizing the potential risk of inducing atrioventricular pressure gradient and thrombogenesis. During the systolic phase, the flow optimizer can expand to seal or minimize the regurgitant orifice and reinstate the efficacy of the tricuspid valve. Further, the anchor, for example, can be configured to anchor the implant proximate to the tricuspid valve without requiring traumatic interaction with the tricuspid valve, right atrium, or right ventricle. The implant can permit intra-procedural adjustments under standard imaging techniques (e.g. fluoroscopy, echocardiography) of the position of the flow optimizer within the native tricuspid valve, thereby providing for real-time optimization of the hemodynamic flow across the tricuspid valve. The implant described herein can advantageously increase the efficacy, safety, and procedural success of transcatheter therapy of tricuspid valve regurgitation.

The flow optimizer can be placed within the lumen of the tricuspid valve and can permit diastolic hemodynamic flow from the right atrium into the right ventricle and, during systole, reduce or prevent blood regurgitation from the right ventricle into the right atrium. The flow optimizer can be placed within the tricuspid valve on the ventricular (distal or bottom) side. The anchor, to which the flow optimizer can be directly connected, can engage the tricuspid valve annulus at the commissures of the native leaflets. Anchoring can be achieved from the atrial (proximal or top) side. In some embodiments, the device can be anchored within the right atrium at the commissures. When implanted at the tricuspid valve, the device can seal the coaptation gap between the native leaflets during the systolic phase of the cardiac cycle and allow blood flow from the right atrium to the right ventricle during the diastolic phase of the cardiac cycle.

The tricuspid valve support devices described herein can be used to reduce or prevent tricuspid regurgitation. The devices can be configured to adopt a crimped conformation so as to be deployed using a standard intravascular catheter. Further, the devices can be configured to adopt a deployed conformation upon placement within the body.

Although shown and described with reference to a tricuspid valve, the device, the flow optimizer and/or the anchoring mechanism can be adapted for use in any valve of the heart.

Figure 1A:
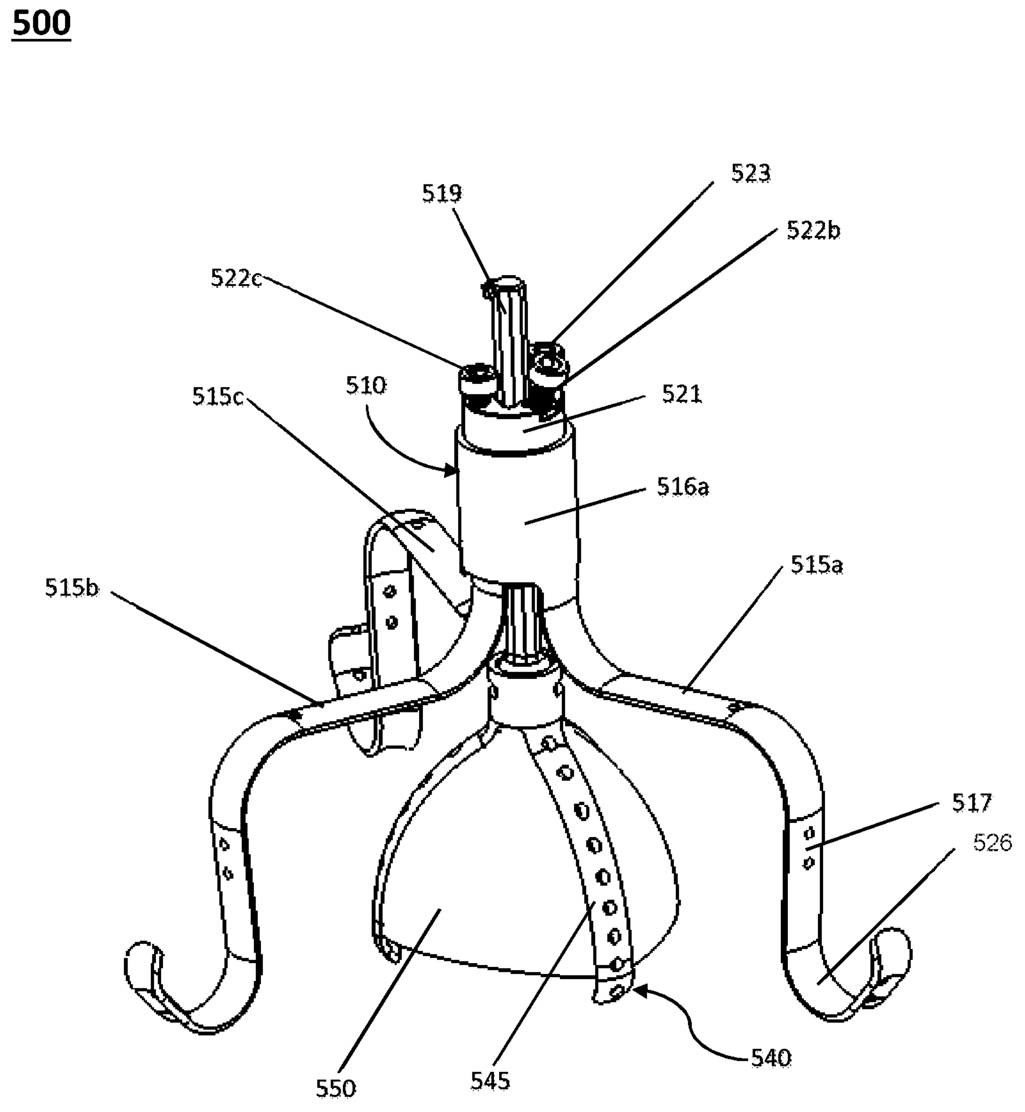
FIG. 1A is a side perspective view of a valve support device.
Figure 1B:
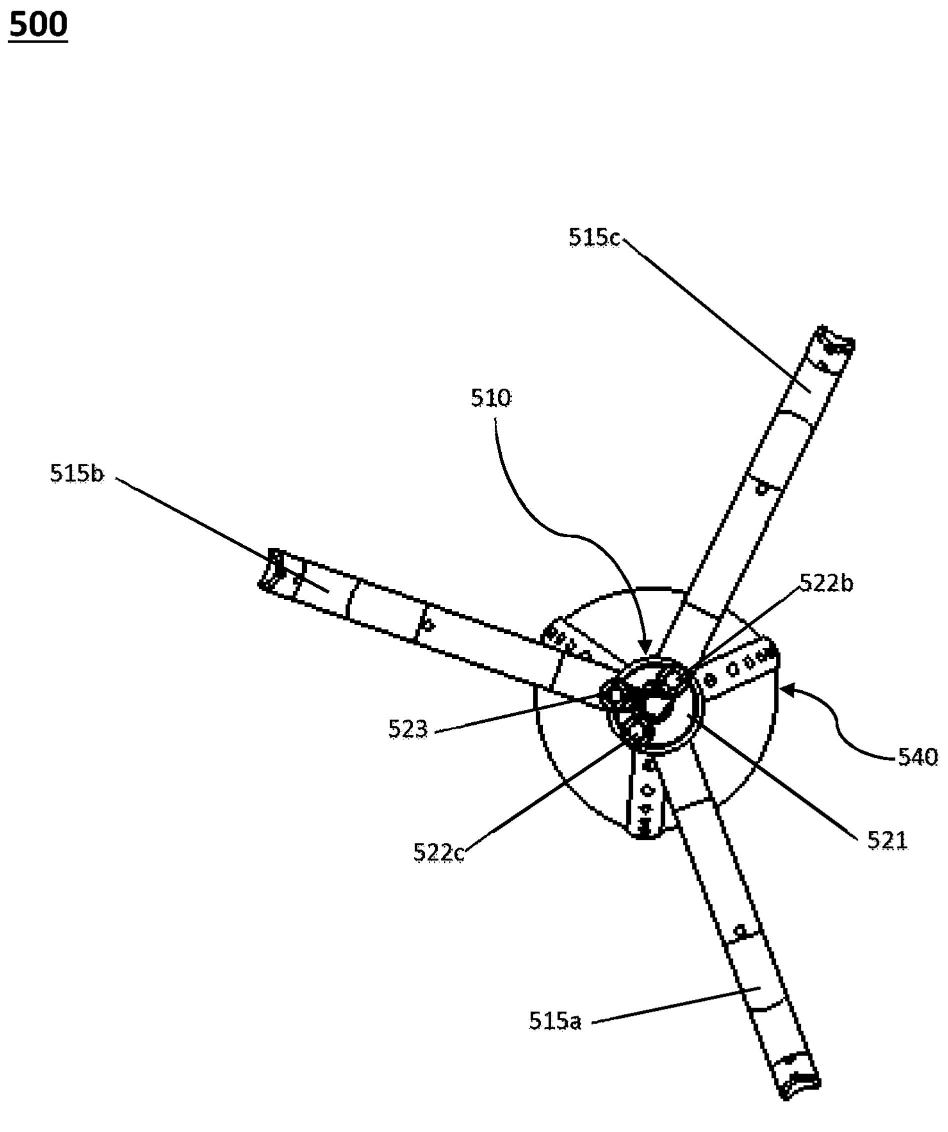
FIG. 1B is a top view of the valve support device of FIG. 1A.

FIGS. 1A-1B illustrate a tricuspid valve support device 500 in a deployed configuration (and with leaflets expanded). The device 500 is configured to be anchored at the annulus of the tricuspid valve. The device 500 includes an anchoring mechanism 510 and a flow optimizer 540 connected with a shaft 519.

Figure 2:
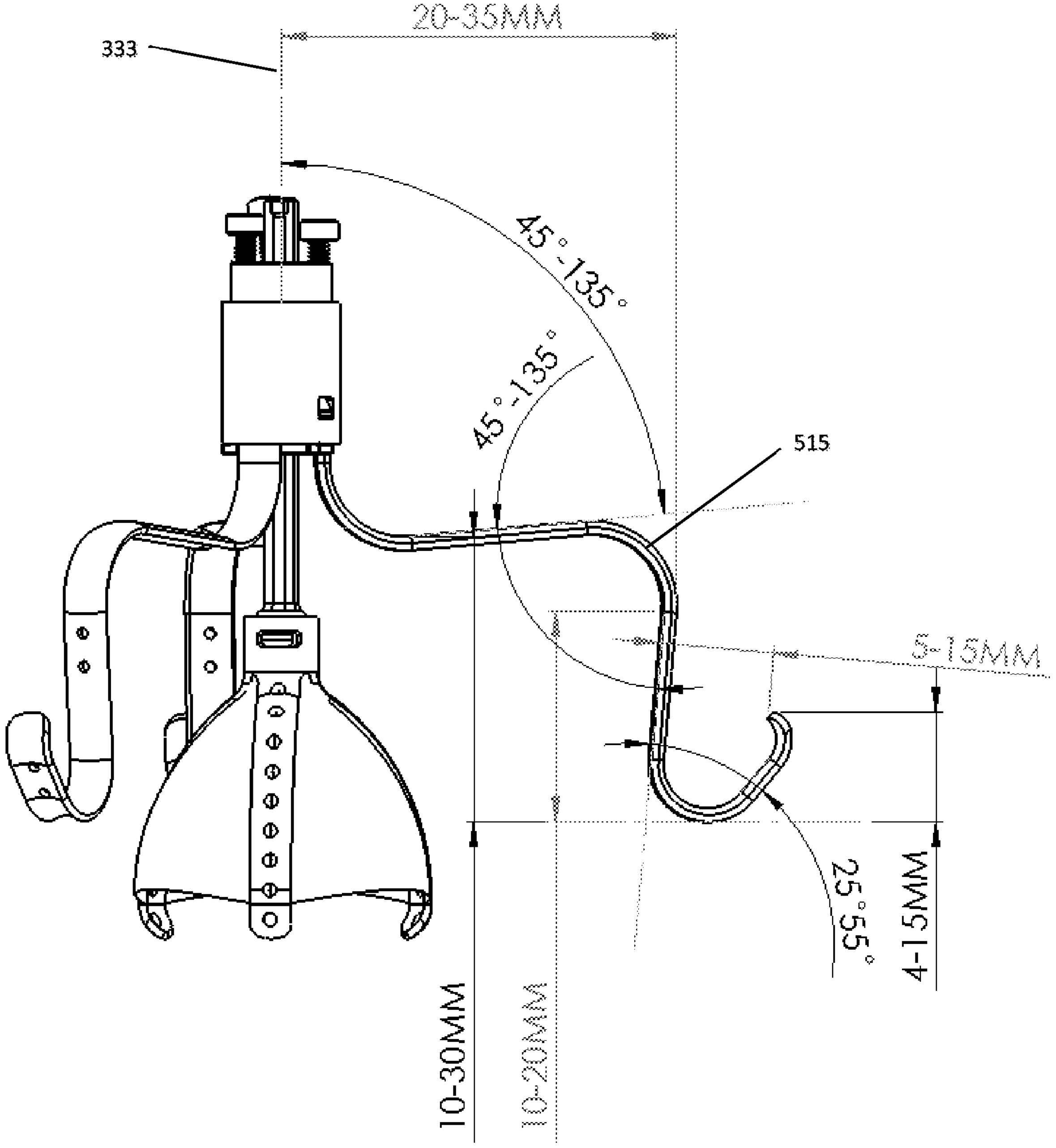
FIG. 2 is a side view of a valve support device showing exemplary dimensions.
Figure 3:
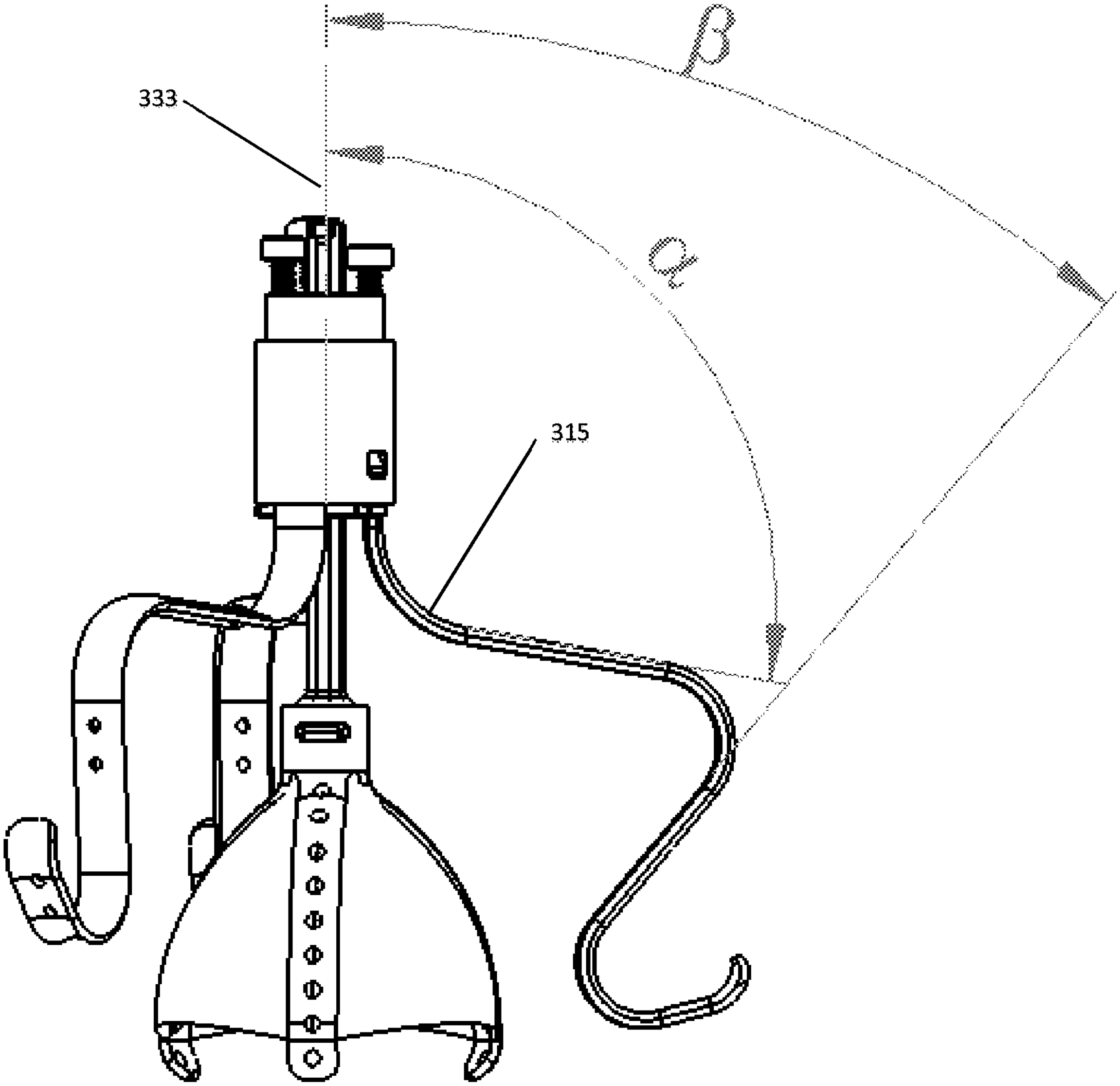
FIG. 3 is a side view of a valve support device with exemplary defined angles.

The anchoring mechanism 510 include a plurality of arms 515*a-c* that are radially disposed around and from an inner core 521 of the device 500. The end region (or distal end region) 526 of the arms 515*a*-515*c* can be contoured to mate with the tissue wall of the tricuspid valve annulus at the commissures of the native leaflets. The intermediate portion 517 of the arms 515*a-c* can be shaped to conform to the inner supra-annular wall of the right atrium to provide further support and/or stabilization. The arms 515*a-c* can be made, for example, of a shape memory material, such as nitinol, so as to collapse for delivery and self-expand outward to conform to the anatomy of the tricuspid valve. When deployed in the tricuspid valve, the end regions 526 of the arms 515*a*-515*c* can mate with the tissue wall of the tricuspid valve annulus at the commissures of the leaflets, and the intermediate portion 517 can rest against the inner supra-annular wall of the right atrium to provide further retention and stabilization to the tricuspid valve flow optimizer 540. Exemplary dimensions and angles of an arm 515 (which can be any of arms 515*a-c*) are shown in FIG. 2. The specific shape of the arms 515*a-c* is exemplary, and it should be understood that other shapes, and corresponding dimensions and angles, are possible. For example, FIG. 3 shows an arm 315 that extends at a wider angle α and angle θ relative to the longitudinal axis 333 of the device than the arm 515.

Figure 4A:
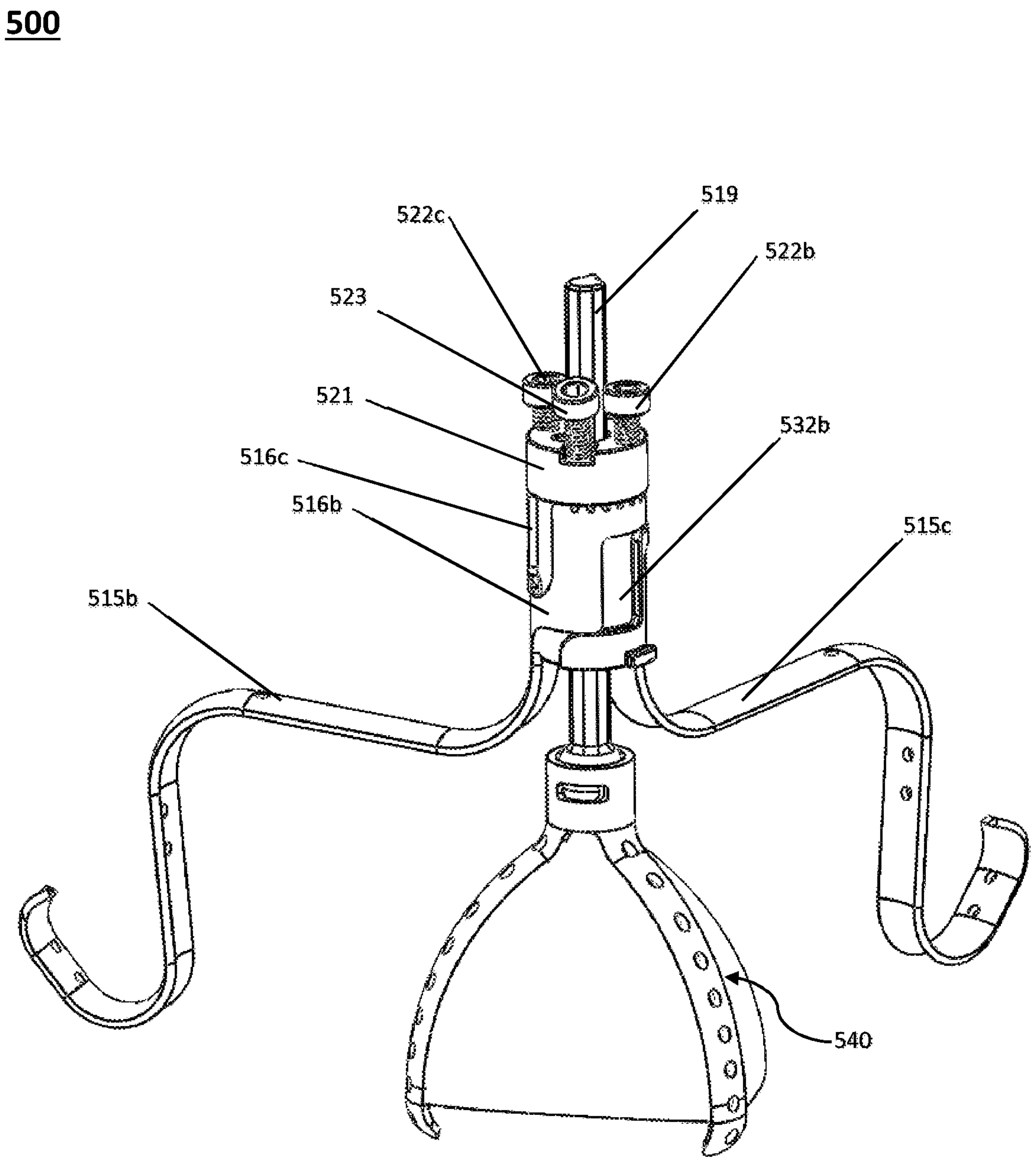
FIG. 4A is a perspective view of the valve support device of FIGS. 1A-1B with one anchoring arm removed for clarity.
Figure 4B:
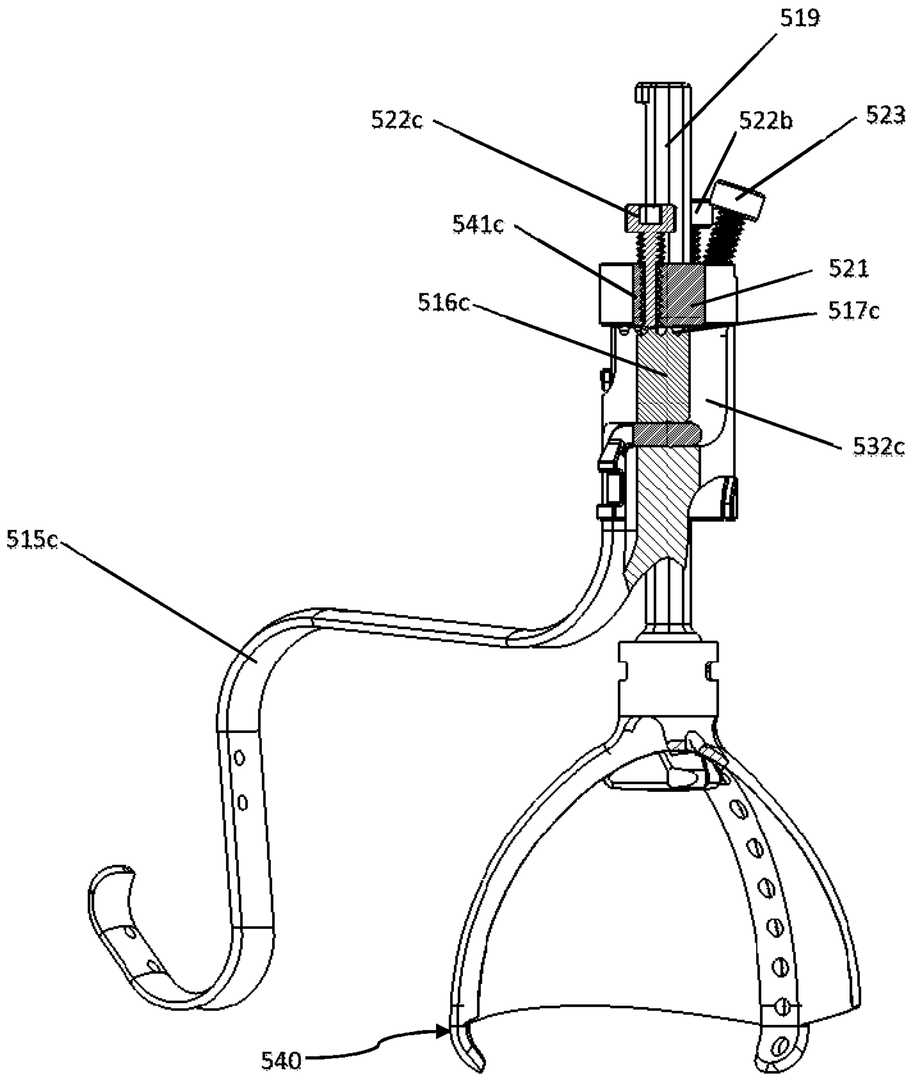
FIG. 4B is a cross-sectional view of the valve support device of FIGS. 1A-1B.
Figure 4C:
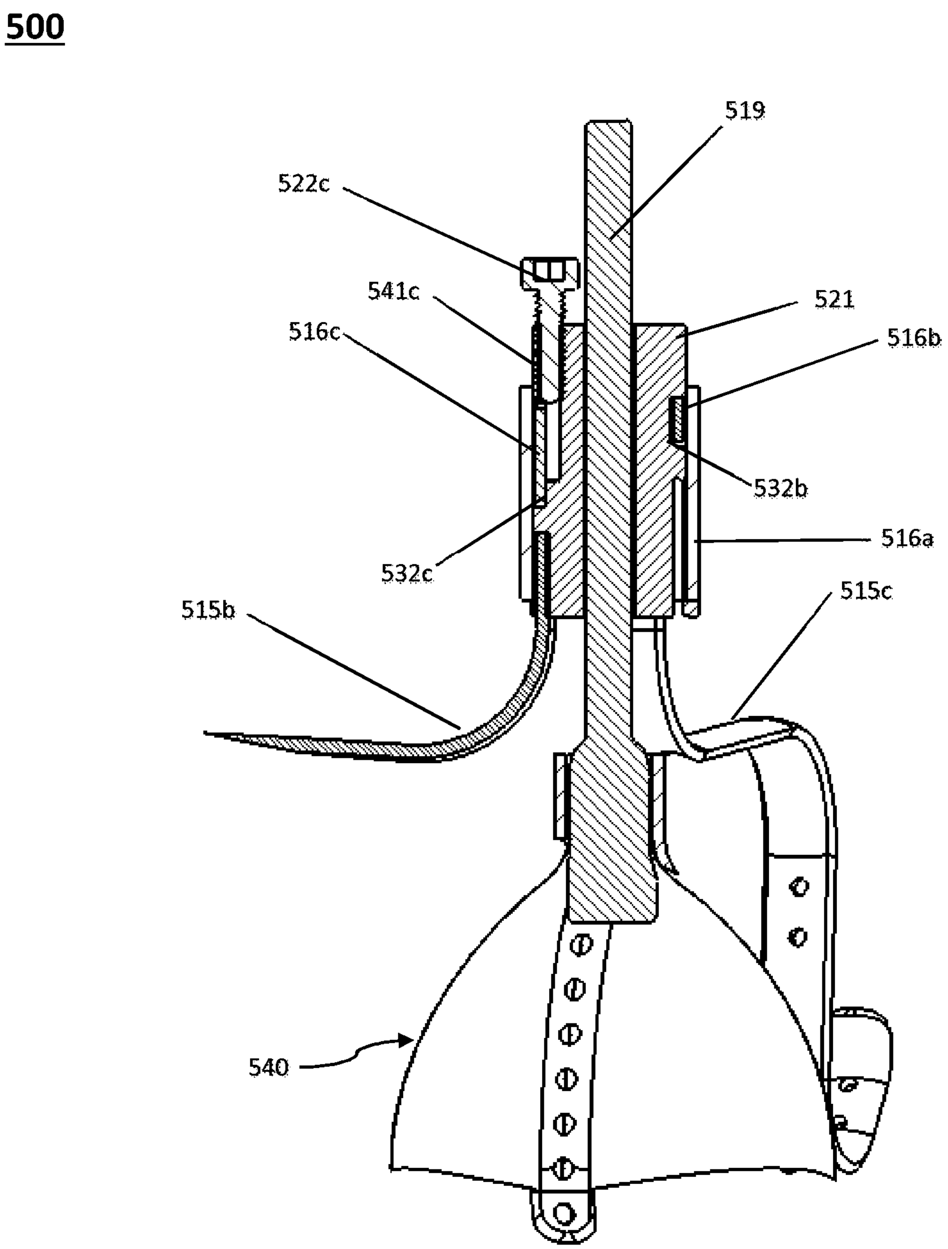
FIG. 4C is another cross-sectional view of the valve support device of FIGS. 1A-1B.

Referring to FIGS. 4A-4C, one or more of the arms 515*a-c* of the anchoring assembly 510 of device 500 can be configured to rotate about the inner core 521. In one embodiment, one arm (515*a*) can remain fixed relative to the inner core 521 while the other two arms (515*b*, 515*c*) can independently rotate clockwise or counterclockwise relative to the inner core 521. For example, fixed arm 515*a* can have a cylindrical proximal portion 516*a*, which can be fixed to the inner core 521, for example, via a snap fit mechanism. The second arm 515*b* can have a proximal portion 516*b* that slides circumferentially along a cam surface 532*b* on the inner core 521. Similarly, the third arm 515*c* can have a proximal portion 516*c* that slides circumferentially along a second cam surface 532*c* on the inner core 521. Once the arms 515*b,c* have reached their desired circumferential position, the arms 515*b,c* can be individually locked in place via activation of the screws 522*b*, 522*c*. For example, screw 522*c* can be configured to extend through a threaded hole 541*c* in the inner core 521. When the screw 522 extends distally out of the hole 541*c*, it can engage with the undulated proximal edge 517*c* of proximal portion 516*c*. In some embodiments, engagement with this undulated edge 517*c* can prevent the arm 515*c* from moving. In other embodiments, the screw 522*c* can extend between the inner core 521 and the proximal portion 516*c* to force the proximal portion 516*c* against the cylindrical proximal portion 516*a* of fixed arm 515*a*, thereby preventing the arm 515*c* from moving due to friction. The screw 522*b* can similarly lock the arm 515*b* in place.

By rotating the arms 515*b*, 515*c*, an operator can advantageously individually position arms 515*b*-515*c* at different relative angles relative to the arm 515*a*, thereby matching angles across the commissures of the leaflets of the patients' native tricuspid valves. As described in further detail below, the rotation and locking of the arms 515*b-c* can be performed pre-procedurally (for example, prior to loading of the device 500 into the delivery catheter), and/or intra-procedurally.

Figure 5A:
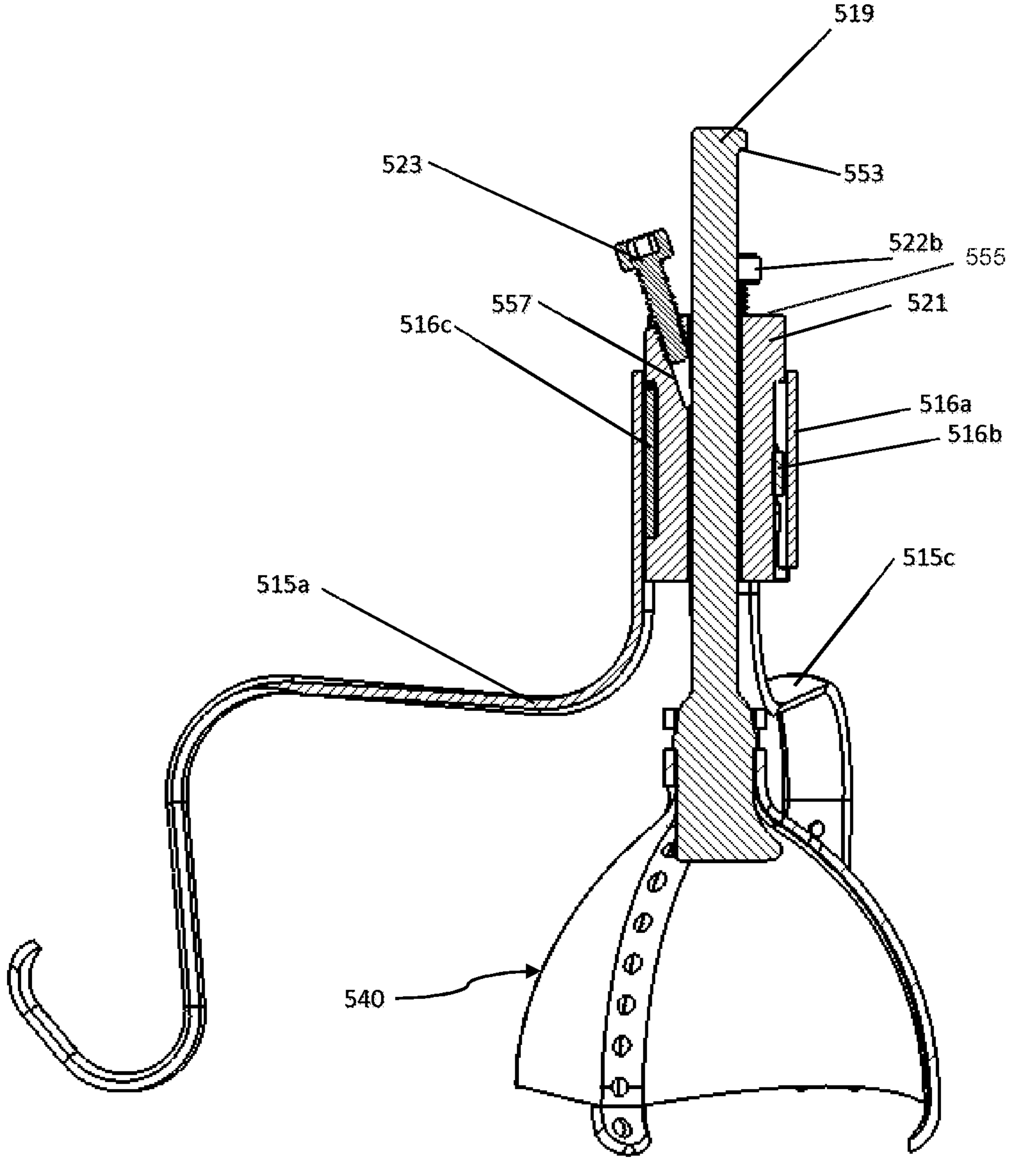
FIG. 5A is another cross-sectional view of the valve support device of FIGS. 1A-1B.
Figure 5B:
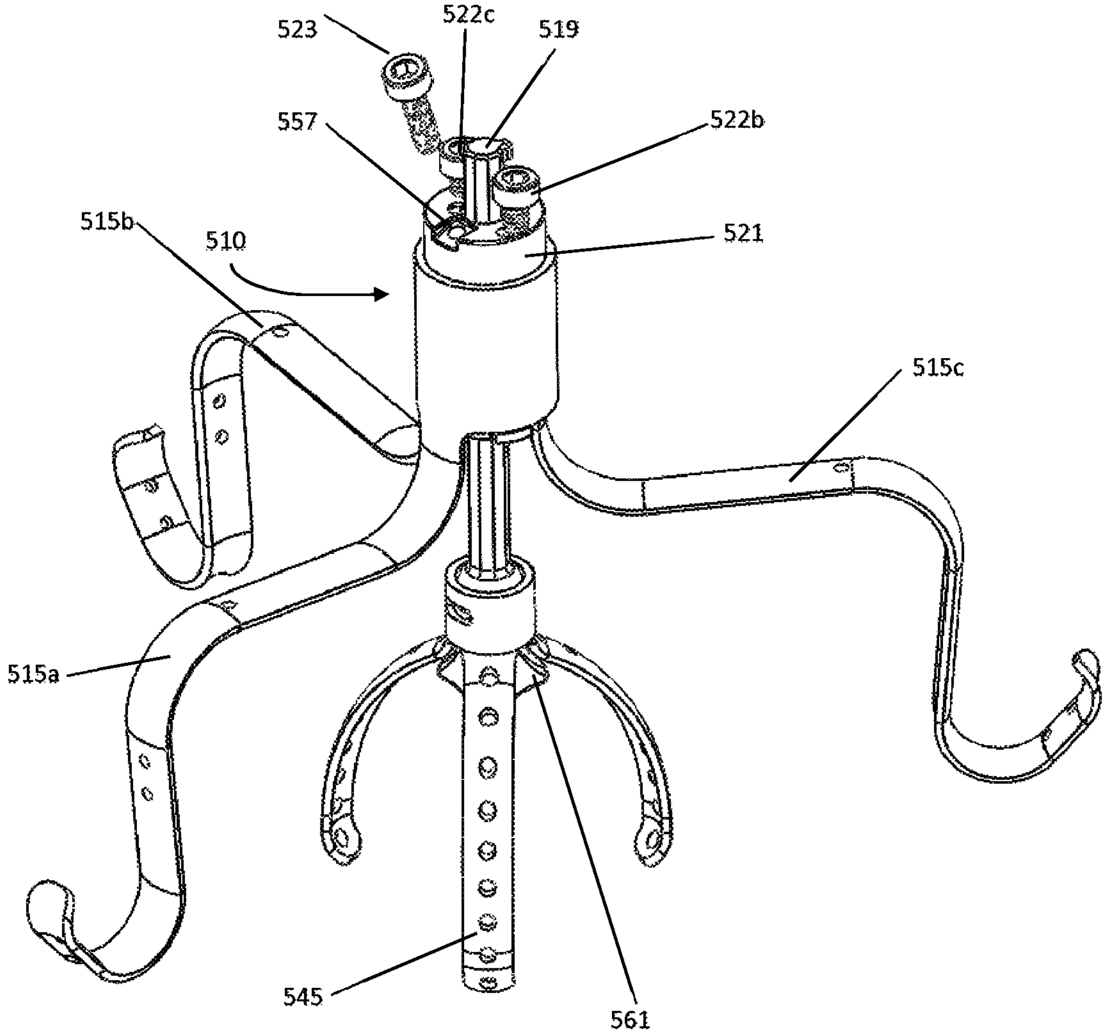
FIG. 5B is a perspective view of the valve support device of FIGS. 1A-1B without the leaflets for clarity.

Referring to FIGS. 5A-5B, the shaft 519, which is fixed to the flow optimizer 540, can be configured to slide and/or rotate axially relative to the anchoring mechanism 510 to provide for axial and rotational adjustment of the relative positions of the anchoring mechanism 510 and the flow optimizer 540 in device 500. For example, the shaft 519 can slide or rotate within a central lumen 551 of the inner core 521. A lip 553 on the proximal end of the shaft 519 can be configured to butt against the proximal end 555 of the inner core 521 to prevent the flow optimizer 540 from completely disengaging with the anchoring assembly 510. Further, once the flow optimizer 540 and anchoring assembly 510 are at the desired relative positions, the flow optimizer 540 and anchoring assembly 510 can be locked in position relative to one another via activation of the screw 523. The screw 523 can engage with (and rotate within) a threaded hole 557 in the inner core 521. The threaded hole 557 can extend at an angle relative to the longitudinal axis of the device (e.g., at an angle of 30-45 degrees). As the screw 523 is moved into engagement with the shaft 519, it can push the shaft 519 against the inner core 521, thereby preventing movement of the shaft 519 relative to the inner core 521 via friction.

The axial and rotational positioning of the flow optimizer 540 relative to the anchoring assembly 510 can be performed pre-procedurally (for example, prior to loading of the device 400 into the delivery catheter), and/or intra-procedurally. Advantageously, when performed while the device 500 is in place in the body, the axial position can be set without requiring rotation of the flow optimizer 540, thereby reducing unwanted interaction with, and/or catching on, the native anatomy. Further, the rotational position of the flow optimizer 540 relative to the anchoring assembly 510 can advantageously be specifically set by rotating the shaft 510 (e.g., once the device 500 is in place in the body), thereby allowing precise positioning of the flow optimizer 540 relative to the native tricuspid valve and optimization of its position relative to the regurgitant orifice. Positioning of the flow optimizer is described in further detail below.

Figure 6:
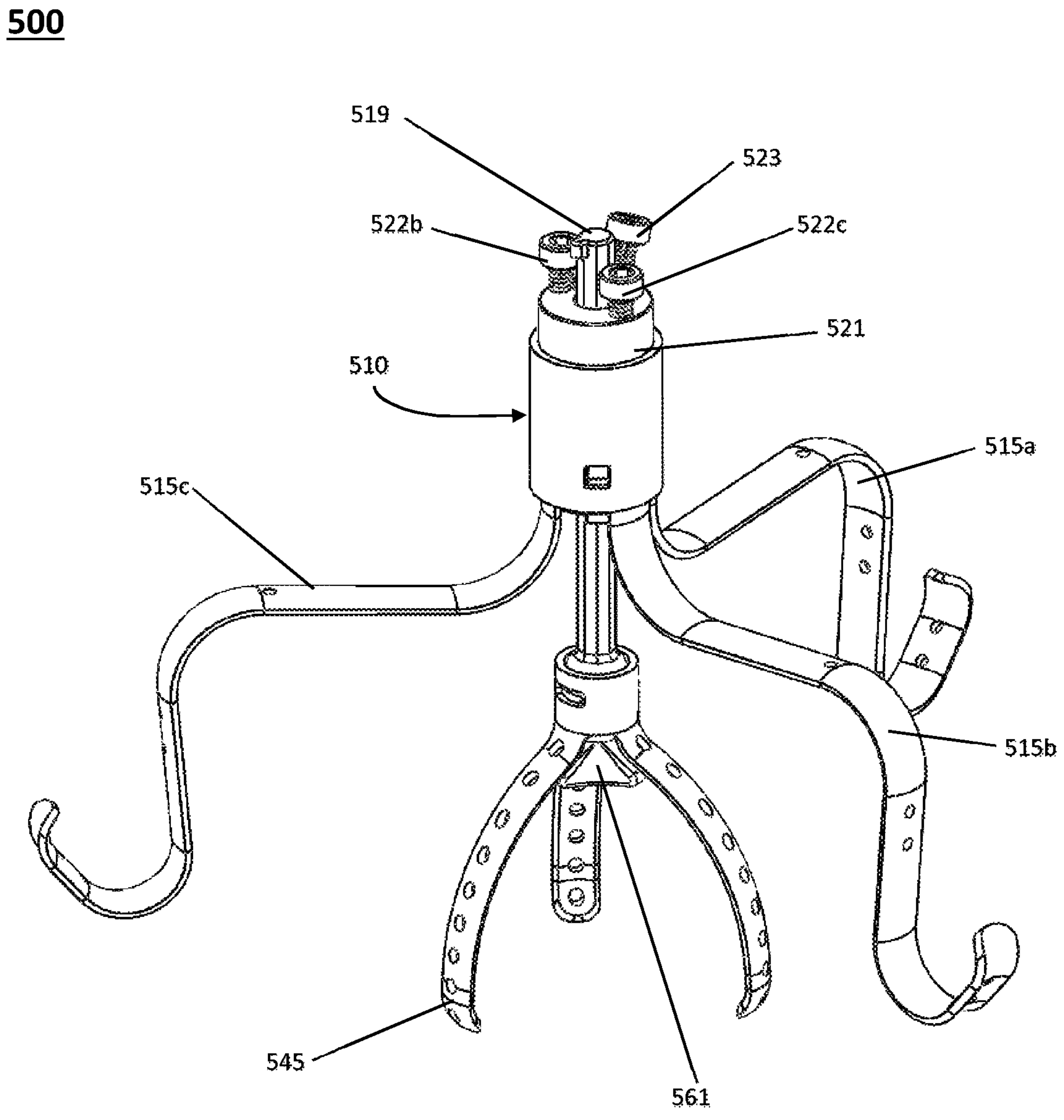
FIG. 6 is another perspective view of the valve support device of FIGS. 1A-1B without the leaflets for clarity.
Figure 7B:
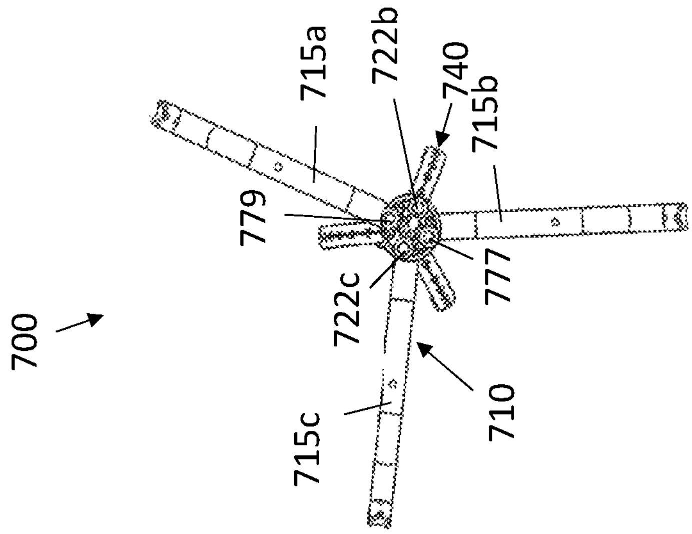
FIG. 7B is a top view of the valve support device of FIG. 7A.
Figure 7A:
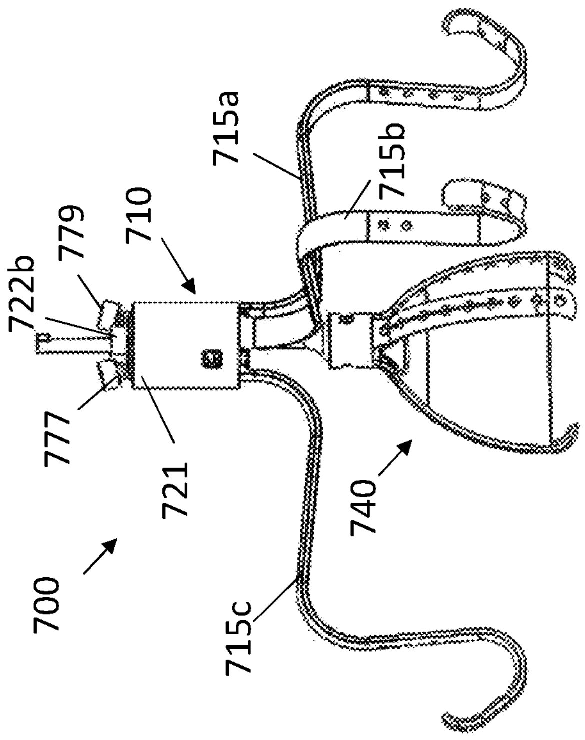
FIG. 7A is a side perspective view of another valve support device.
Figure 7C:
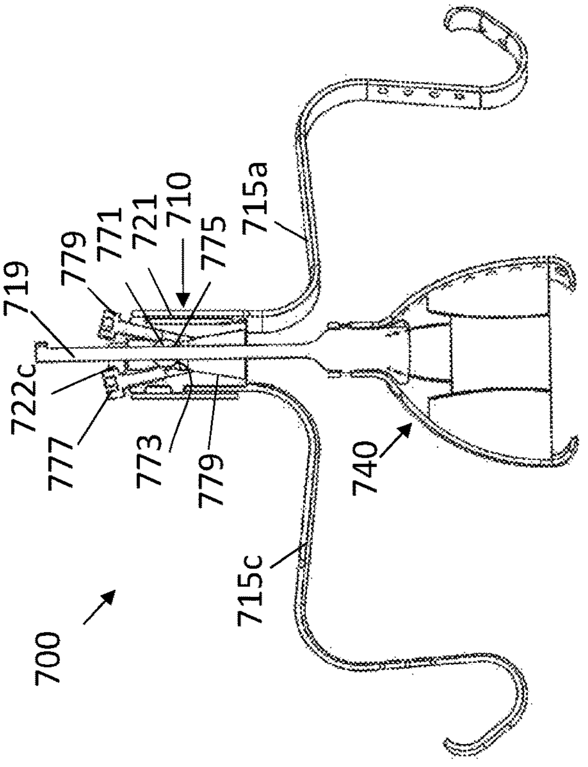
FIG. 7C is a cross-sectional view of the valve support device of FIG. 7A.
Figure 8A:
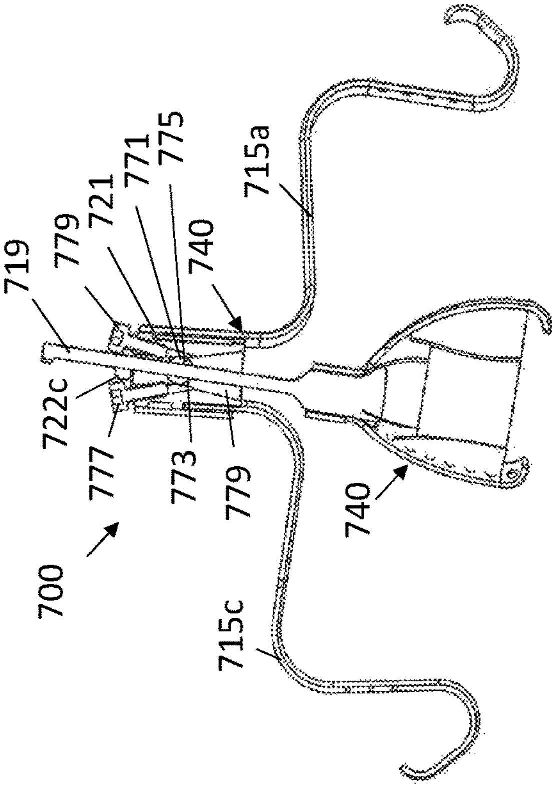
FIG. 8A is a cross-sectional view of the valve support device of FIG. 7A with the flow optimizer tilted relative to the anchoring assembly.
Figure 8C:
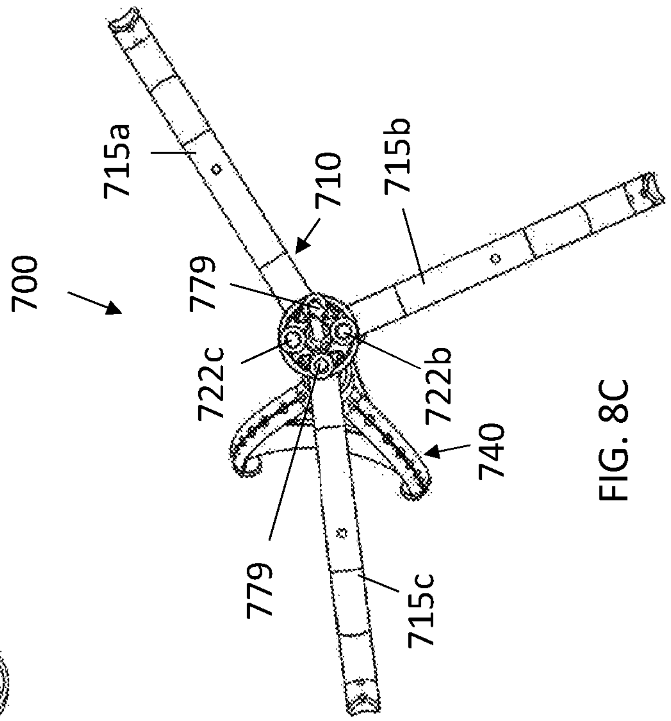
FIG. 8C is a top perspective view of the valve support device of FIG. 8A.
Figure 8B:
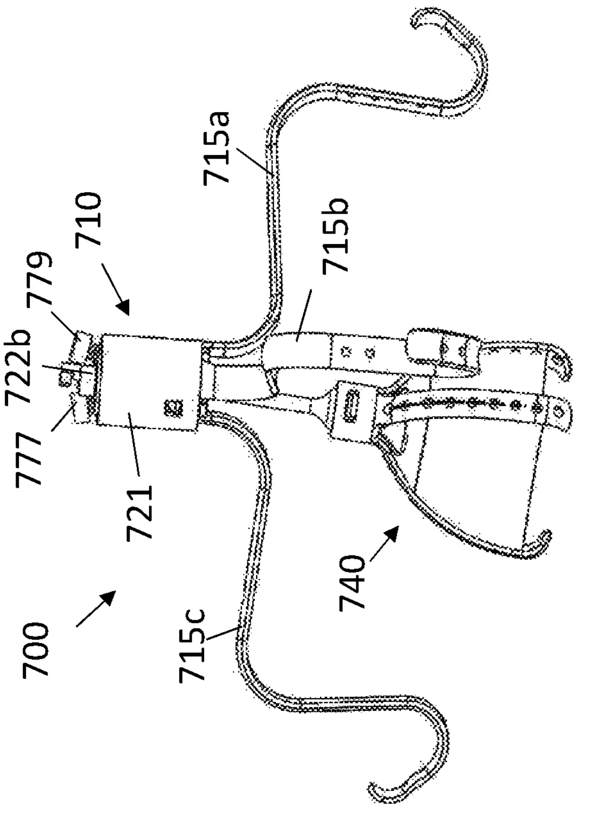
FIG. 8B is a side perspective view of the valve support device of FIG. 8A

Referring back to FIG. 1A, the flow optimizer 540 can include a frame 545 supporting leaflets 550 that are radially expanded (as shown in FIG. 1A) during systole and radially collapsed towards the central axis during diastole. The frame 545 can include a plurality of convex arms extending from the shaft 519. The convex arms can ensure that the flow optimizer 540 maintains a substantially convex cup shape when expanded. This can advantageously ensure that no blood pools between the anchor assembly 510 and the flow optimizer 540 during systole. Further, as shown in FIG. 6, the distal end 561 of the shaft 519 can have detents cut therein to avoid interaction with the collapsed leaflets 550 during diastole.

During diastole, when blood flows from the right atrium into the right ventricle through the tricuspid valve under atrial contraction, the atrioventricular hemodynamic pressure gradient opens the tricuspid valve leaflets (similar to as shown in FIGS. 7A-8C). The atrioventricular hemodynamic pressure gradient can collapse the leaflets 550 of flow optimizer 540 towards the center axis of the frame 545, such that the three-dimensional volume and cross sectional area of the flow optimizer 540 can be reduced, thereby allowing blood to flow unrestricted into the ventricle around the flow optimizer 540. During systole (i.e., ventricular contraction), when the tricuspid valve leaflets coapt around the flow optimizer 540, the ventricular hemodynamic pressure can inflate the leaflets 550 to their full or partial three-dimensional volume, which can be sufficient to close the tricuspid valve regurgitant orifice and reduce or prevent blood flow into the right atrium.

Advantageously, the device 500 can ensure that the pressure gradient across the tricuspid valve after implantation remains low, such as less than 3 or less than 2 mmHg.

Device 500 can be loaded, for example, within an intravascular catheter and delivered to the right atrium and into the tricuspid valve either via transfemoral access through the IVC, or via right internal jugular vein access of the IVC.

Another embodiment of a tricuspid valve support device 700 is shown in a deployed configuration (and with leaflets collapsed) in FIGS. 7A-8C. The support device 700 is similar to support device 500 and includes an anchoring mechanism 710 with a plurality of arms 715*a-c* that are radially disposed around and from an inner core 721 (and that can be locked with screws 722*b,c*). Further, the shaft 719, which is fixed to the flow optimizer 740, can be configured to slide and rotate axially relative to the anchoring mechanism 710 (similar to device 500), and the leaflets of the flow optimizer can expand and collapse during systole and diastole, respectively.

Unlike device 500, however, the shaft 719 and flow optimizer 740 of device 700 is configured so as to also be adjustably positioned off-axis relative to the anchoring mechanism 710 (i.e., can be configured to tilt). This tilting adjustment can allow for precise angular positioning of the flow optimizer 740 relative to the native tricuspid valve. To enable adjustable angular positioning of the flow optimizer 740, the device 700 (e.g., the core 721) includes a ball 771 positioned within a socket 773. The ball 771 includes a lumen 775 through which the shaft 719 extends, and the shaft 719 can slide or rotate within the central lumen 775. Further, the ball 771 can rotate within the socket 773, thereby allowing placement of the flow optimizer 740 off-axis relative to the anchoring mechanism 710 (see FIGS. 8A-8C). An angled ledge 779 on the lumen 751 of the core 721 can prevent the flow optimizer 740 from extending at too large of an angle relative to the anchoring mechanism 710 (e.g., the angle of the axis of the anchoring mechanism 710 relative to the axis of the flow optimizer 740 can be limited to less than 45 degrees, such as less than 35 degrees, such as less than 25 degrees. Adjusting the tile of the flow optimizer is described in further detail below.

Once the flow optimizer 740 and anchoring assembly 710 are at the desired relative positions, the flow optimizer 740 and anchoring assembly 710 can be locked in position relative to one another via activation of screws 777, 779. The screws 777, 779 can engage with (and rotate within) threaded holes in the inner core 721. The threaded holes can extend at an angle relative to the longitudinal axis of the device (e.g., at an angle of 5-45 degrees, such as 10-30 degrees). The screws 777, 779 can be configured to extend through the holes until they engage with the ball 771. Upon engagement by a first amount, the position of the ball 771 can be fixed, thereby fixing the angular position of the anchoring assembly 710 relative to the flow optimizer 740. At this first amount, the shaft 719 can still be permitted to move (e.g., axially slide and rotate) within the lumen 775 (e.g., for axial or rotational positioning of the flow optimizer 740 relative to the anchoring assembly 710). Upon tightening the screws 777 by a second additional amount, the ball 771 can push against the shaft 719 and thereby prevent the shaft 719 from moving within the lumen 775 and fixing the axial and rotational position of the flow optimizer 740 relative to the anchoring assembly 710.

FIGS. 16A-16D show another embodiment of a tricuspid valve support device 1600. The device 1600, similar to device 700, includes a shaft 1619 and flow optimizer 1640 that are configured to be positioned off-axis relative to the anchoring mechanism 1610 (i.e., can be configured to tilt). Like device 700, the device 1600 includes a ball 1671 positioned within a socket 1673. Unlike device 700, however, device 1600 includes an annular lock 1662 configured to fit within the inner core 1621. The annular lock 1662 can include threaded grooves 1664 along the outside thereof configured to engage with threaded grooves 1666 on an inner surface of the inner core 1621. In use, the annular lock 1662 can be positioned in a proximal configuration (shown in FIGS. 16A-16B) such that the flow optimizer 1640 is free to tilt relative to the anchoring assembly 1610. Once the flow optimizer 1640 and anchoring assembly 1610 are at the desired relative positions, the flow optimizer 1640 and anchoring assembly 1610 can be locked in positioned relative to one another via activation of the annular lock 1662. To do so, the annular lock 1662 can be rotated within the inner core 1621, resulting in the annular lock 1662 moving distally towards the ball 1671 and into a distal configuration (shown in FIG. 16C). Upon engagement with the ball 1671 by a first amount, the position of the ball 1671 can be fixed, thereby fixing the angular position of the anchoring assembly 1610 relative to the flow optimizer 1640. At this first amount, the shaft 1619 can still be permitted to move (e.g., axially slide and rotate) within the lumen 1675. Upon further rotation of the annular lock 1662 distally, the ball 1671 can push against the shaft 1619 and thereby prevent the shaft 1619 from moving within the lumen 1675 and fix the axial and rotational position of the flow optimizer 1640 relative to the anchoring assembly 1610.

FIGS. 17A-17E show another embodiment of the proximal end of a tricuspid valve support device 1700. The device 1700, similar to device 1600, includes an annular lock 1762 to lock the tilting position of flow optimizer relative to the anchor assembly. The annular lock 1762, in contrast to annular lock 1662, can be a snap fit lock (rather than a screw lock). As shown in FIGS. 17A-17B, the annular lock 1762 can be positioned in a proximal configuration in which the lock 1762 is not engaged with the ball 1761 and the shaft 1719 is free to tilt (and/or rotate or move axially). As shown in FIGS. 17C-17D, the annular lock 1762 can be pushed distally (i.e., rather than rotated) to the distal configuration in which the lock 1762 engages with the ball 1761 to lock the position of the shaft 1719.

Advantageously, the adjustability of the arms of the anchoring mechanisms described herein (e.g., shape and rotational position) in combination with the adjustability of the position of the anchoring mechanism relative to the flow optimizer as described herein (e.g., rotational, angular, and/or axial) provides for precise alignment of the device relative to the native tricuspid valve. The device can be fully integrated with the tricuspid valve and annulus, moving harmonically and ergonomically in systolic and diastolic phases without impeding the atrium or ventricle. Additionally, this adjustability can be performed live by the operator, thereby allowing immediate assessment and adjustments before permanently implanting the device, improving treatment outcome. Similarly, the amount of seal (partial or total) within the tricuspid valve provided by the flow optimizers described herein can be adjusted intraprocedurally (via tilt, rotation, and axial adjustment of the flow optimizer relative to the anchoring mechanism) and can be based on assessment or monitoring of the patient's RV functionality and pulmonary artery pressure.

Figure 9A:
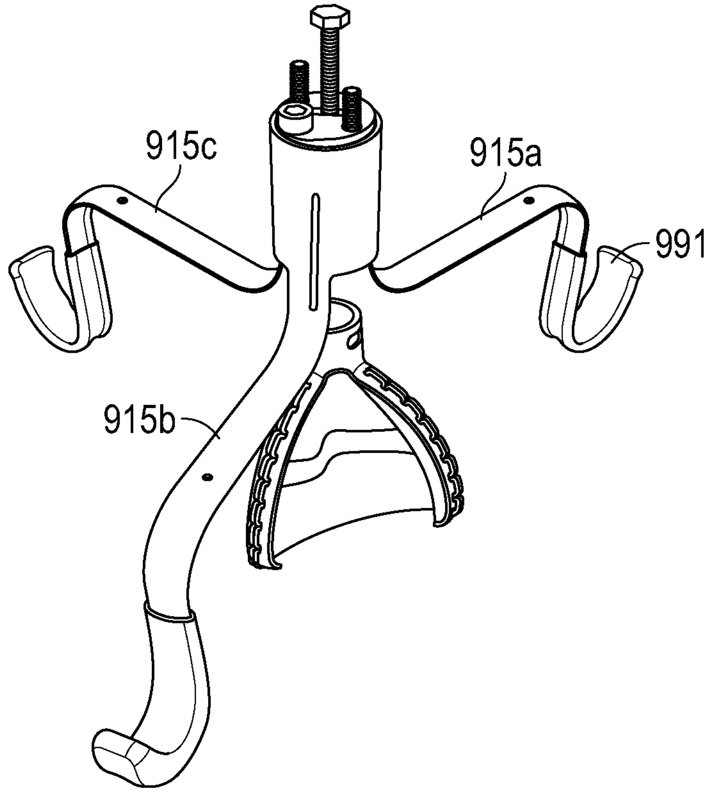
FIG. 9A is a perspective view of a valve support device having a covering on the outer tips of the anchoring arms.
Figure 9B:
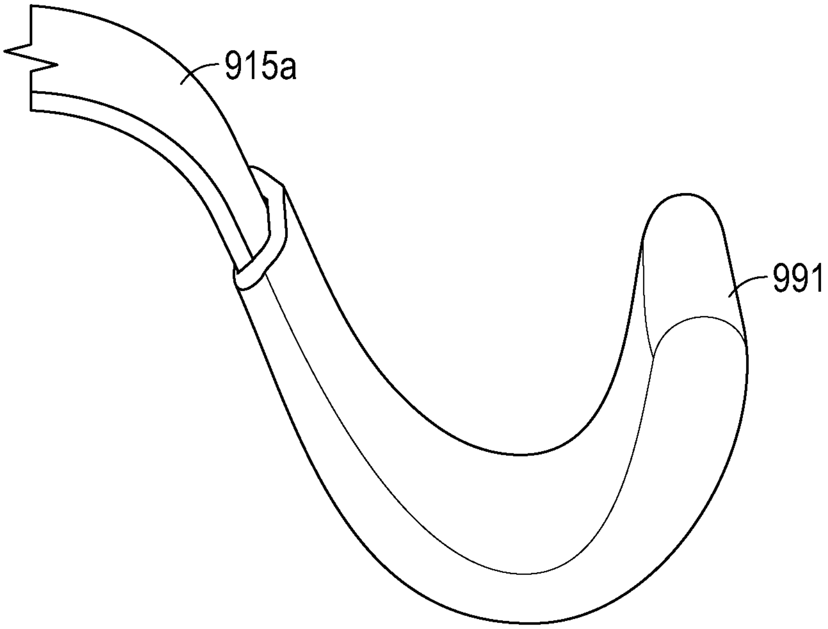
FIG. 9B is a close-up view of the outer tips of the anchoring arms of the device of FIG. 9A.

Referring to FIGS. 9A-9B, in some embodiments, the anchoring arms 915*a-c* of any of the devices described herein (e.g., arms 515*a-c* and 715*a-c*) can include a covering 991 on the outer tips thereof. The covering 991 can be made, for example, of polyethylene terephthalate fabric. In some embodiments, the covering 991 can extend only around the outer portion of the arms 915*a*, such as along the outer 10-40%, such as 25-35% of the arms 915*a-c*. The covering 991 can advantageously enhance endothelial growth and subsequent encapsulation of the outer tips of the anchors 915*a-c* (e.g., at the annulus). The remaining portions of the arms 915*a-c* can remain uncovered, thereby helping to prevent thrombus formation during use.

Figure 15A:
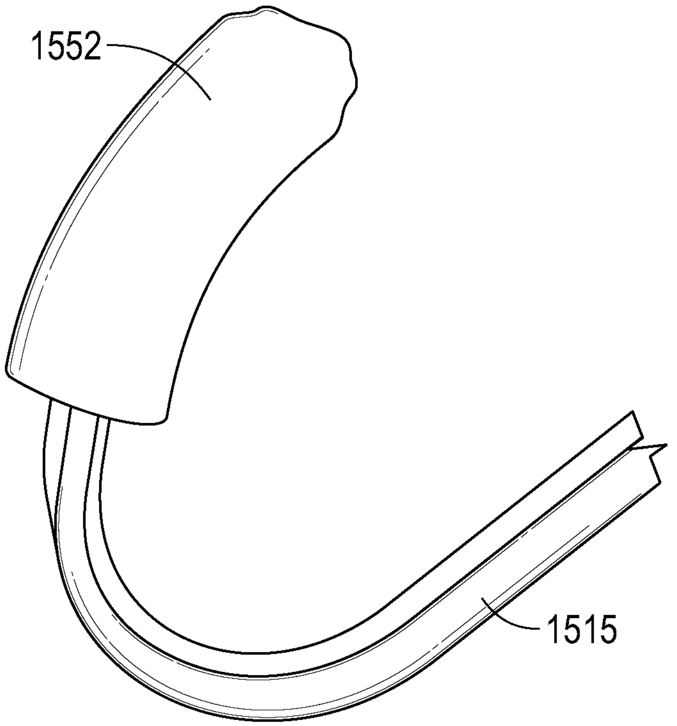
FIG. 15A shows the distal tip of a valve support device anchoring arm with a cushion thereon (outer sleeve is removed for clarity).
Figure 15B:
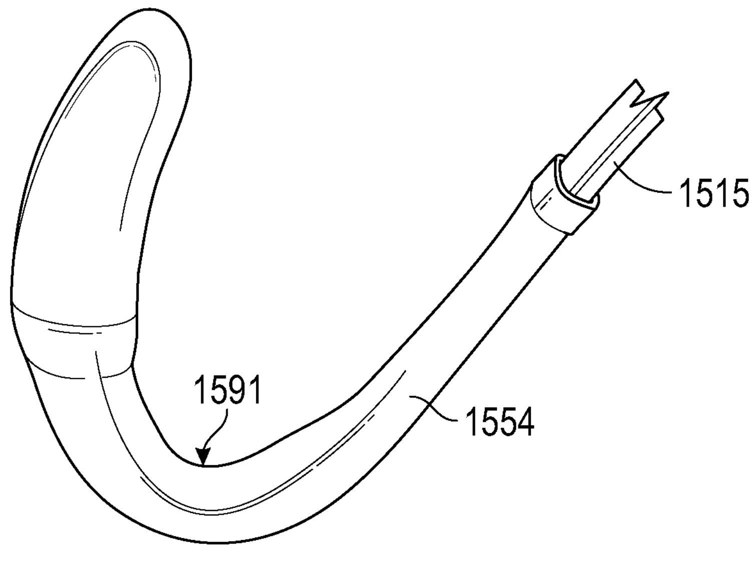
FIG. 15B shows the distal tip of FIG. 15A with the sleeve thereover.
Figure 16A:
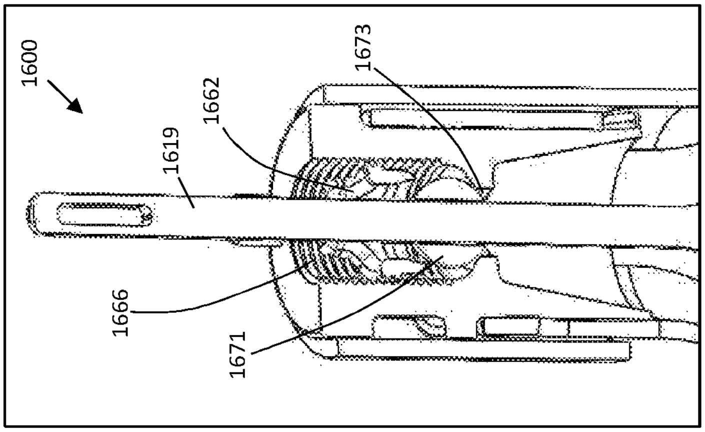
FIG. 16A is a cross-sectional view of the proximal end of a valve support device with an annular lock in a proximal (unlocked) configuration.
Figure 16B:
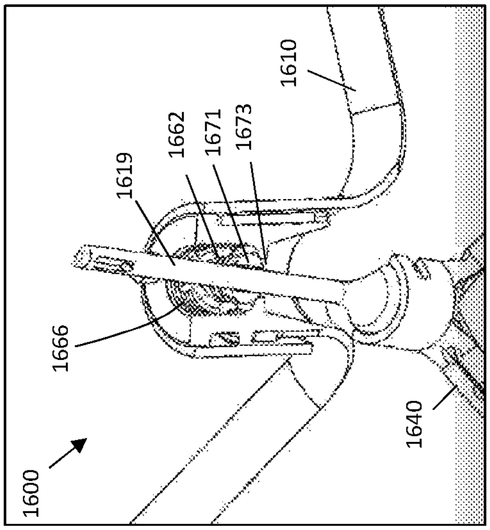
FIG. 16B is a perspective view of the valve support device of FIG. 16A with the annular lock in the proximal position and the flow optimizer tilted relative to the anchoring mechanism.
Figure 16C:
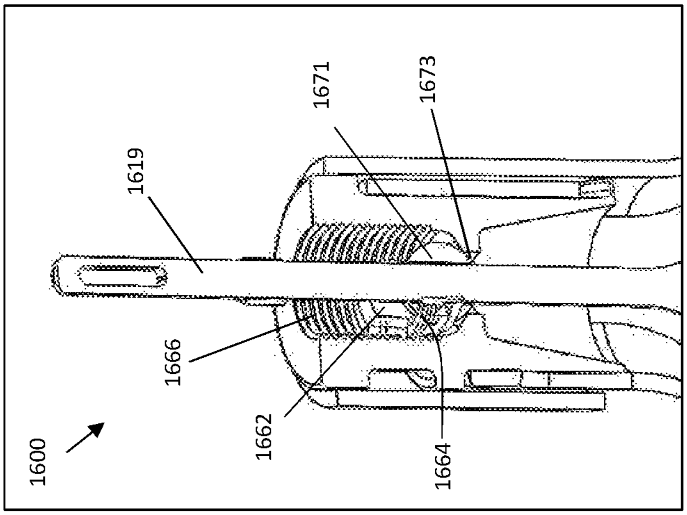
FIG. 16C is a cross-sectional view of the valve support device of FIG. 16A with the annular lock in the distal (locked) configuration.
Figure 16D:
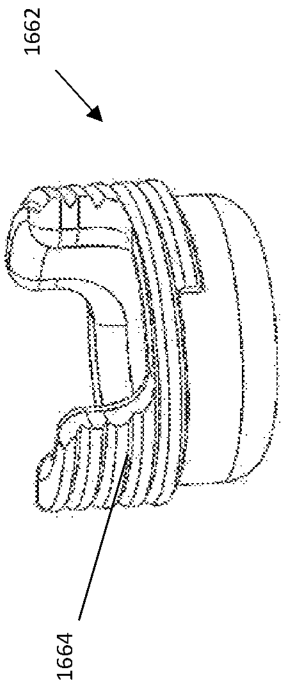
FIG. 16D is a perspective view of the annular lock of the device of FIG. 16A.

Referring to FIGS. 15A-15B, in some embodiments, the covering 1591 (e.g., covering 991) can include a cushion 1552 and a sleeve 1554. The cushion 1552 can extend, for example, only on the distal tip of each arm 1515, such as along the portion of the arms 1515 that hooks backwards (e.g., within the outer 10% of the arm 1515). The sleeve 1554 can be placed over the cushion 1552 and the arms 1515 and can extend the full length of the covering 1591. The cushion 1552 can advantageously aid in making the tips of the arms 1515 atraumatic. In some embodiments, the cushion 1552 can be made of a plurality of layers of fabric, such as 3-10, such as 4-8 layers of fabric that are sealed together. For example, the cushion 1552 can be made of layers of polyethylene terephthalate (PET) fabric. In some embodiments, the cushion 1552 can be made of a single piece of foam.

The leaflets for any of the devices described herein can be made of a material that is impermeable to blood cells and, preferably, impermeable to blood fluids (e.g., aqueous solutions). For example, the leaflets can be formed from any suitable biocompatible material including, for example, woven or nonwoven polymer fabrics or sheets and/or biological tissue harvested from animals (e.g., bovine, porcine, and equine) or humans. Suitable biological tissue includes, for example, tissue obtained from the pericardial sac of the donor animal and/or human. In some embodiments, the leaflets can be made of a composite polymer material. The composite material can be made of a two-dimensional woven (or braided or knitted) fabric (e.g., a PET fabric sheet) or of a three-dimensional thermo-formed fabric (e.g., a PET fabric shape). The fabric layer can advantageously carry the cyclic fatigue loading exerted on the leaflets by the cardiac cycle's hemodynamic flow. The porosity of the fabric can be engineered to allow coating it with a biocompatible and anti-thrombus coating, such as polyurethane (PU) or polyurethane-silicone (PU-Sil), without significantly affecting the fabric's flexibility. In some embodiments, the coating can be applied in liquid form to the fabric using standard coating manufacturing processes (i.e. dipping, spraying, electro-spinning). The coating can fully cover and isolate the fabric from the blood stream. In some embodiments, the final composite material (e.g., PET+PU or PET+PU-Sil) can provide high fatigue resistance due to the woven fabric substrate and strong chemical stability due to the coating.

The leaflets can be sutured or attached with other standard fastening methods (e.g. adhesives) on the arms of the frame (e.g., frame 545). Additionally and/or alternatively, the leaflets can be molded in the desired three dimensional shape as a single sub-assembly mountable on the frame.

Figure 10A:
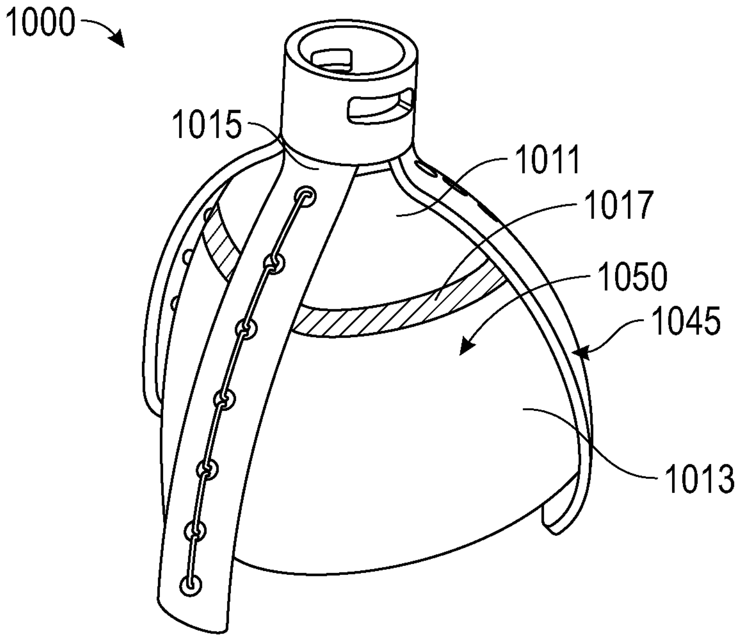
FIG. 10A is a perspective view of a flow optimizer with multi-layered leaflets in the expanded configuration.
Figure 10B:
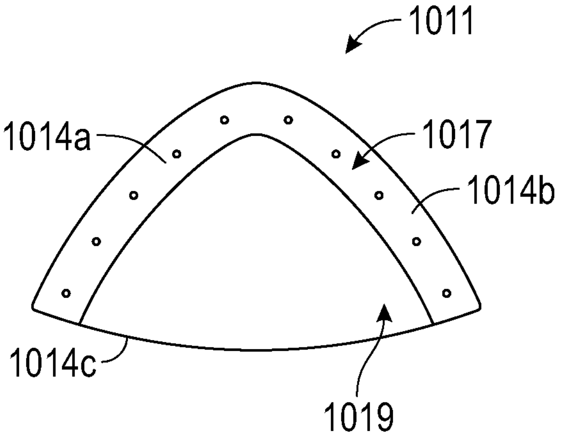
FIG. 10B shows a top layer of the leaflets of FIG. 10A.
Figure 10C:
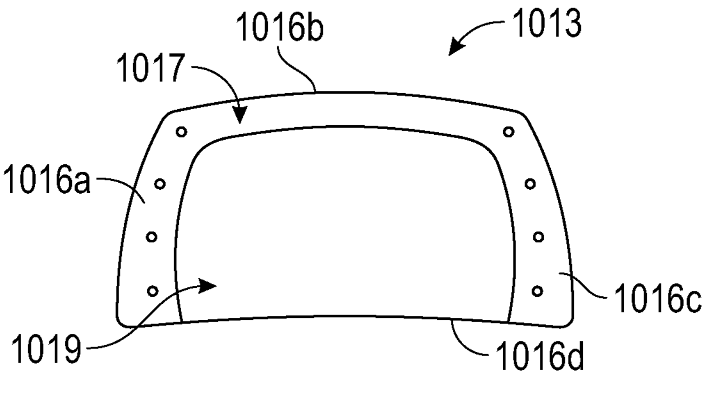
FIG. 10C shows a bottom layer of the leaflets of FIG. 10B.

Referring to FIGS. 10A-10C, in some embodiments, the leaflets 1050 (which can be any of the leaflets described herein) of device 1000 can be composed of two circumferential layers. That is, each leaflet can have a top layer 1011 (positioned towards the apex 1015 at the atrial end of the frame 1045) and a bottom layer 1013 (positioned towards the ends or tips of the convex frame arms at the ventricular end of the frame 1045). The top layer 1011 can be substantially triangular in shape while the bottom layer 1013 can be substantially rectangular or quadrilateral in shape. The layers 1011, 1013 can be in a radially overlapping configuration with the bottom layer 1013 positioned radially outwards of the top layer 1011. During systole, the leaflets 1050 can be substantially convex (as shown in FIG. 10A), and layers 1011 and 1013 can be sealed against and/or in contact with one another.

As shown in FIGS. 10B-10C, each individual leaflet layer 1011, 1013 can include a rim 1017 and a membrane 1019. The membrane 1019 can include a thin layer of polymeric material, such as polyurethane-silicone. The rim 1017 of the top layer 1011 can extend along first and second edges 1014*a,b* (closest to the apex 1015) while leaving the third edge 1014*c* (the ventricular-most edge) without a rim. Similarly, the rim 1017 of the bottom layer 1013 can extend along first, second, and third edges 1016*a, b, c* while leaving the fourth edge 1016*d* (the ventricular-most edge) without a rim. The rim 1017 can be made, for example, of a fabric, such as polyethylene terephthalate fabric. In some embodiments, the rim 1017 can have a coating thereover, such as a coating of polyurethane and/or silicone. Further, the rim 1017 can be thicker and/or have greater stiffness than the membrane 1019.

Figure 11A:
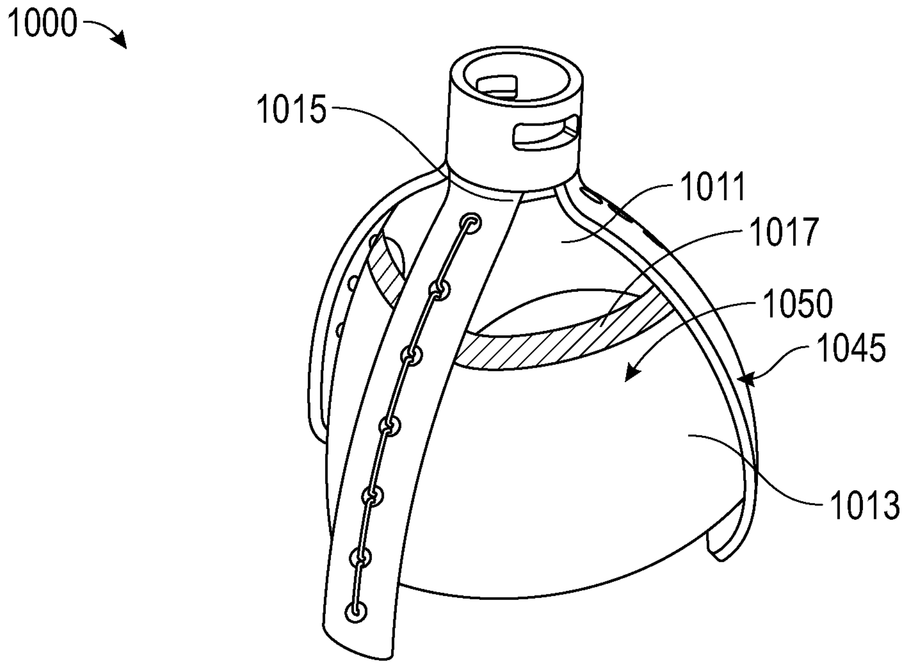
FIG. 11A is a perspective view of the flow optimizer of FIG. 10A with the top layer collapsed and the bottom layer expanded.
Figure 11B:
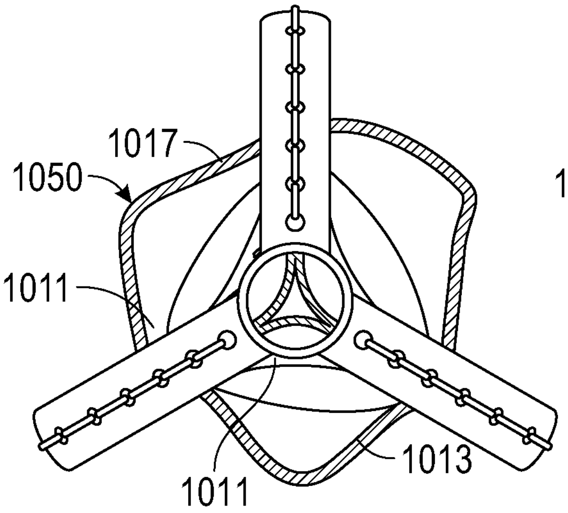
FIG. 11B is a top view of the flow optimizer of FIG. 11A.
Figure 11C:
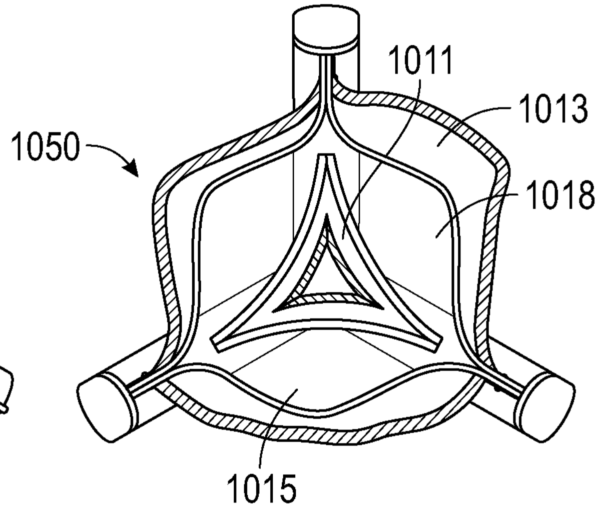
FIG. 11C is a bottom view of the flow optimizer of FIG. 11A.

Referring to FIGS. 11A-11C, during diastole, when blood flows from the right atrium into the right ventricle, the hemodynamic pressure gradient can cause the leaflets 1050 of device 1000 to collapse towards the center axis of the frame 1045 and/or to become concave (the concave leaflets 1050 are shown in FIG. 11A). As shown in FIGS. 11B-11C, because the overlapping layers 1013, 1011 have varying stiffness (i.e., due to the position and size of the rims 1017), the top layer 1011 can collapse first, thereby leaving a gap 1018 between the top layer 1011 and the bottom layer 1013. That is, the stiffness of the rim 1017 along the edges 1016*a, b, c* of the bottom layer 1013 can hold the bottom layer 1013 radially outwards longer than the unrimmed overlapping bottom edge 1014*c* of the top layer 1011. Having the layers 1011, 1013 move sequentially (e.g., the top layer 1011 move radially inwards before the bottom layer 1013) can allow blood to flow through the gap 1018, minimizing the potential areas for blood stagnation and thus preventing thrombus formation in or around the leaflets 1050. Additionally, the sequential collapse can help minimize obstruction of atrioventricular flow during the diastolic phase by reducing the effective orifice area (e.g., can help maintain the gradient of less than 3 mmHg, such as less than 2 mmHg post-implantation). In other embodiments, the top and bottom layers 1011, 1013 can be configured so as to collapse simultaneously.

Figure 12A:
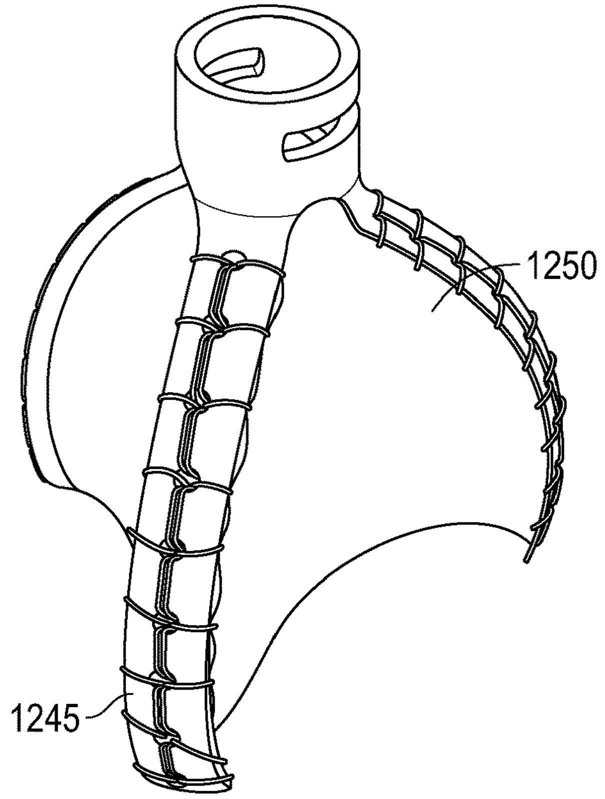
FIG. 12A is a perspective view of a flow optimizer with leaflets sewn to the frame in a first stitch pattern.
Figure 12B:
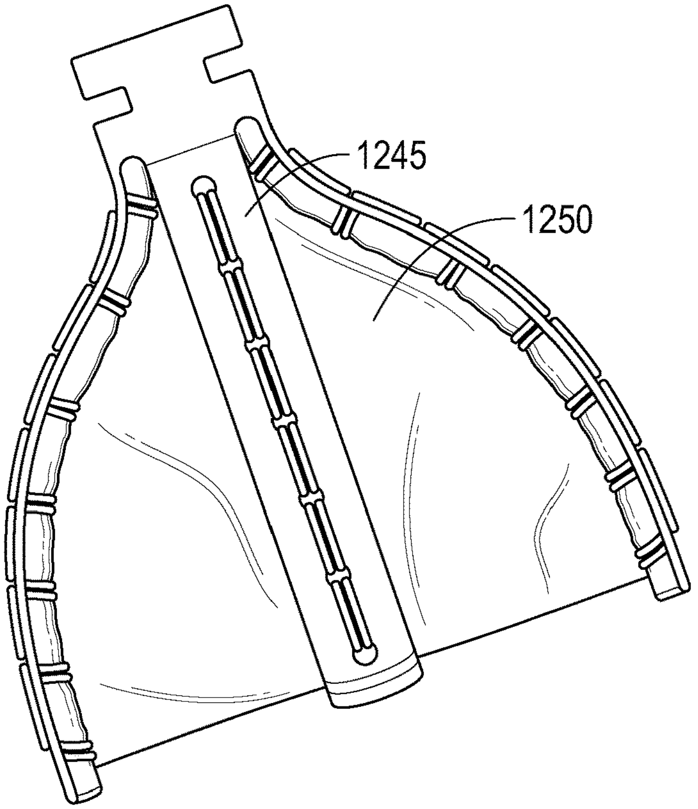
FIG. 12B is a perspective view of a flow optimizer with leaflets sewn to the frame in a second stitch pattern.

Referring to FIGS. 12A-12B, the leaflets 1250 (which can be any of the leaflets described herein) can be sewn to the frame 1245 along the rims (e.g., the rims 1017, 1019 along edges 1014*b,c* and 1016*a, b, c* of FIGS. 10A-10C). The stitches can be parallel with the rims, which can advantageously reduce the impact on blood flow and reduce the risk of thrombosis. In some embodiments, the stitches can be positioned through predrilled (e.g., laser cut) holes to ensure alignment of the components when sewn together. The stitches can be wrapped around the arms of the frame 1245 (as shown in FIG. 12A) or extend only in direction parallel to the arms of the frame 1256 (as shown in FIG. 12B).

Figure 13A:
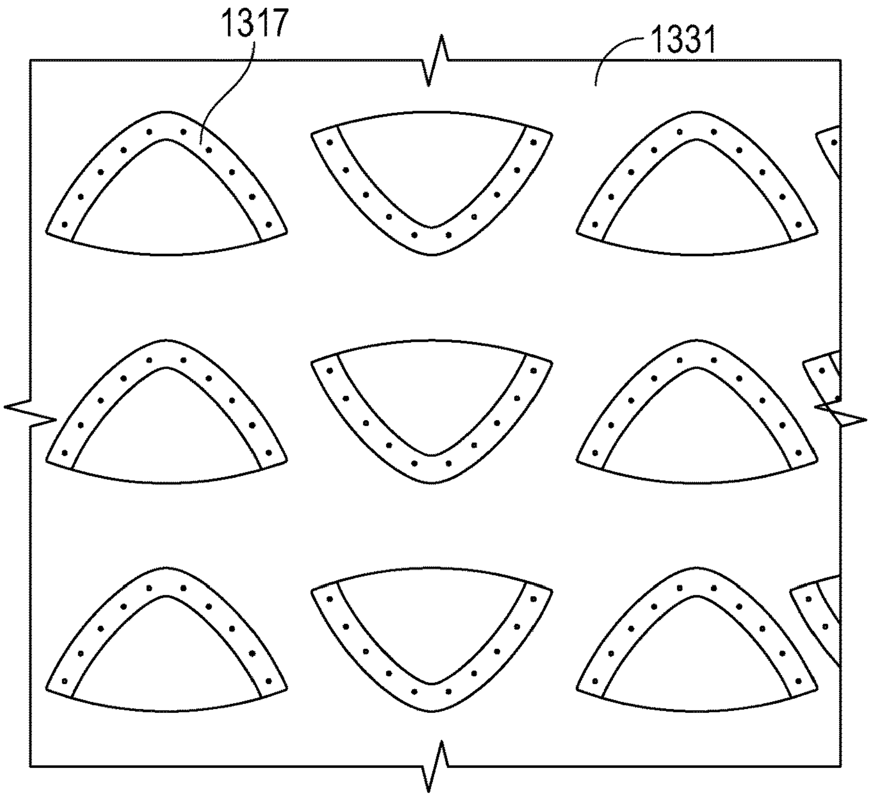
FIG. 13A shows a pattern for cutting a top layer of leaflets.
Figure 13B:
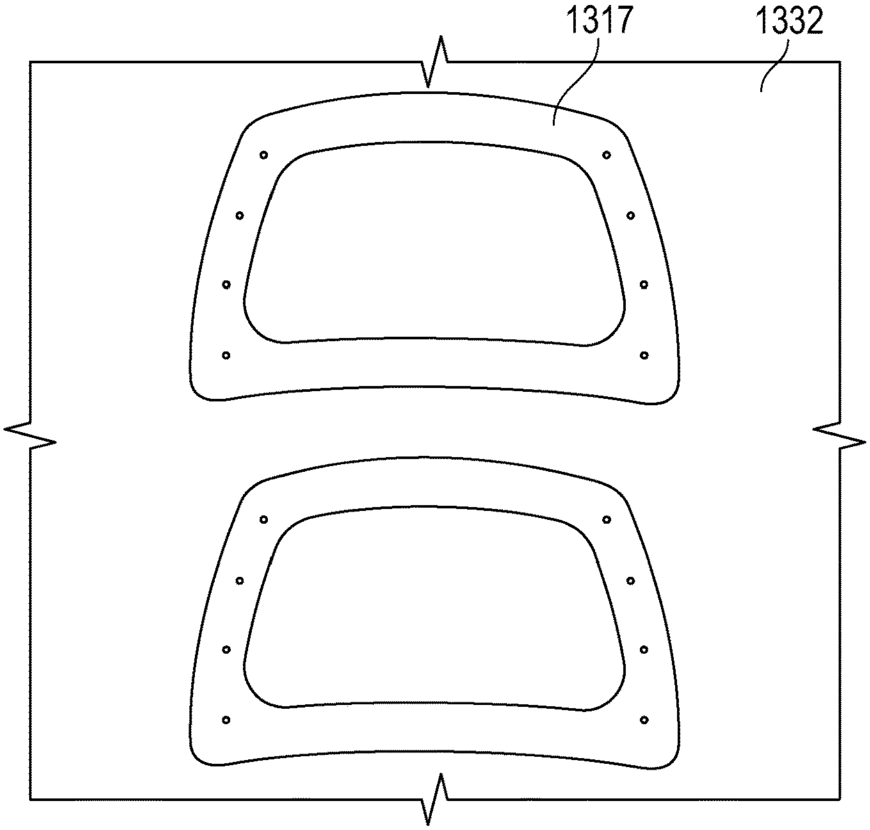
FIG. 13B shows a pattern for cutting a bottom layer of leaflets.

Referring to FIGS. 13A-13B, an exemplary method of manufacturing leaflets includes:

1) Obtaining a panel 1331, such as polyethylene terephthalate fabric coated with polyurethane and silicone. The panel 1331 can be, for example, 40 μm thick.
2) Laying the panel 1331 on a tray, such as a borosilicate glass tray.
3) Laser cutting the pattern of the top leaflets (as shown in FIG. 13A) into the panel 1331.
4) Removing the center portion of the top leaflets from the panel 1331, leaving only the rims 1317.
5) Repeating steps 1-5 for the bottom leaflets (the patterned panel 1332 for which is shown in FIG. 13B).
6) Coating the entire surface of the panels 1331, 1332, including the cut-out portions, with one layer of a coating, such as a coating of polyurethane and silicone. The coating can be, for example, 20 μm thick. The coating can create the membrane between the rims 1307.
7) Repeating step 7 to apply additional coating layers as required to reach a thickness of the rim and membrane as desired.
8) Cutting the completed leaflets away from the panels 1331, 1332.

Figure 14A:
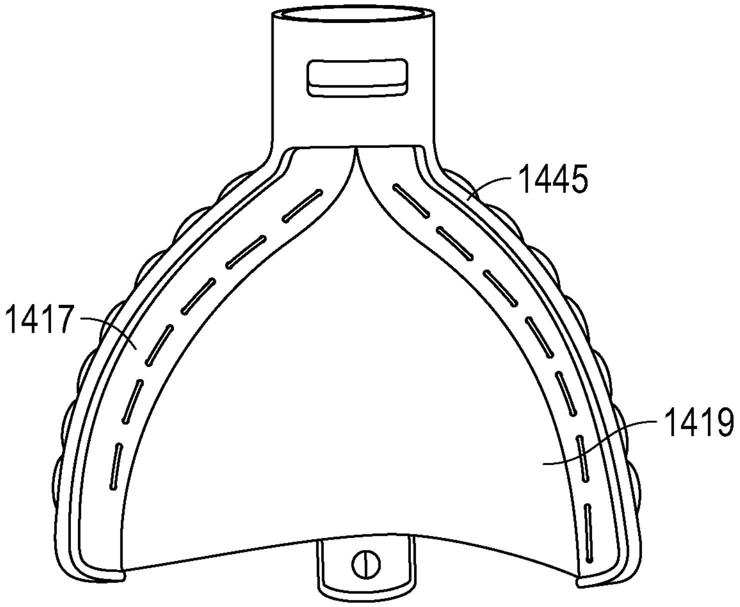
FIG. 14A is a perspective view of a flow optimizer with single-layer leaflets.
Figure 14B:
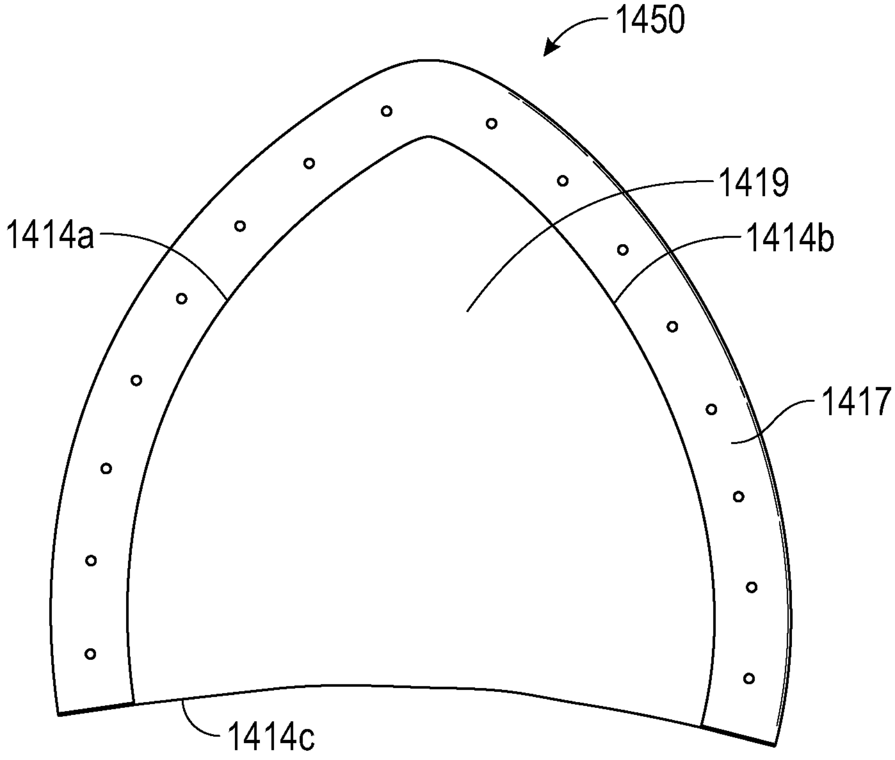
FIG. 14B shows a leaflet of the flow optimizer of FIG. 14A.

Referring to FIGS. 14A-14B, in some embodiments, the leaflets 1450 (which can be used as part of any of the flow optimizers described herein) can be composed of a single circumferential layer. Each leaflet 1450 can have a substantially triangular shape. Additionally, each leaflet 1450 can have a rim 1417 and a membrane 1419 as described above with respect to leaflets 1050. Similar to the top layer 1011, the rim 1417 can extend along first and second edges 1414*a,b* (towards apex 1415) while leaving a third edge 1414*c* (the ventricular-most edge) without a rim. The leaflets 1450 can be made with the same process as described above with respect to the dual circumferential layers of leaflets with the exception of step 5 (i.e., without manufacturing the bottom leaflets). In use, during diastole, when blood flows from the right atrium into the right ventricle, the hemodynamic pressure gradient can cause the leaflets 1450 to collapse towards the center axis of the frame 1445. Because the membrane 1419 is thinner than the rim 1417 (e.g., has a thickness than is less than 75%, such as less than 60%, such as less than 55%, such as less than or equal to 50% of the rim), the membrane 1419 can advantageously collapse quickly during diastole (and similarly expand quickly during systole).

In some embodiments, the ratio of the cross-sectional area of the device relative to the area of the tricuspid valve annulus during diastole can be less than 0.4, such as less than 0.3, such as less than or equal to 0.26. Having a low ratio of cross-sectional area relative to the tricuspid valve annulus can advantageously help ensure that the pressure gradient across the valve remains low (such as less than 3 or less than 2 mmHg).

In some embodiments, some or all of the devices described herein can be echogenic and/or radiopaque, allowing for intraprocedural visualization.

Advantageously, the devices described herein can be placed even in the presence of a pacemaker lead. Additionally, the devices described herein can allow for the crossing of ancillary devices from the right atrium to the right ventricle without interfering with the device functionality.

In some embodiments, the cross-section of an expanded flow optimizer as described herein can be substantially round or oval (or a convex triangle) while the cross-section of the unexpanded flow optimizer can be triangular (or a concave triangle).

The devices described herein can additionally or alternatively include any of the features described in PCT Publication No. WO/2018/119192, titled "Heart Valve Support Device and Methods for Making and Using the Same," the entirety of which is incorporated by reference herein.

Delivery System and Control Mechanisms for Heart Valve Support Device

Embodiments of a delivery system for delivering and positioning the heart valve support devices described herein are provided.

Figure 18A:
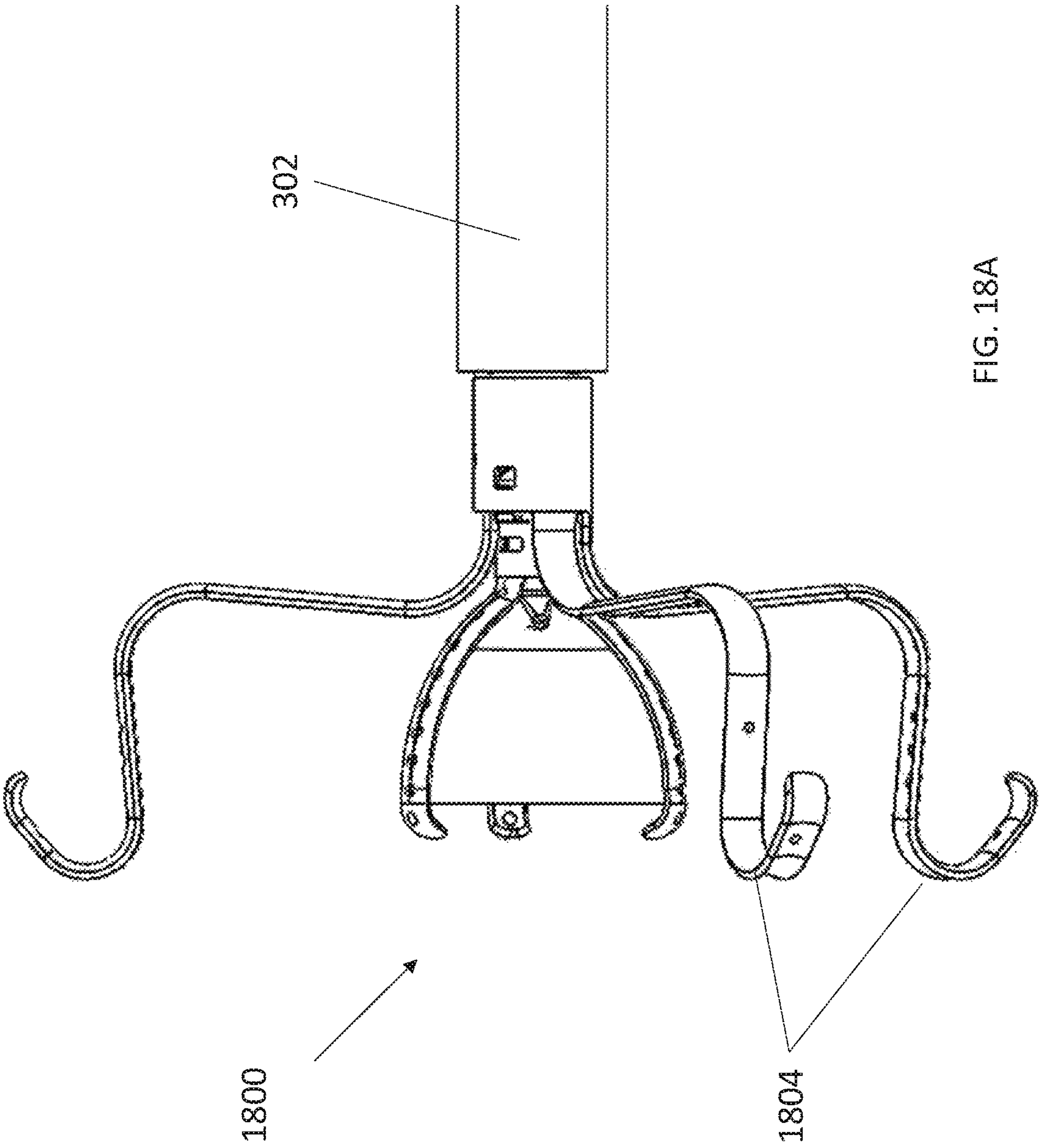
FIG. 18A shows a side view of an embodiment of a valve support device being delivered through a catheter.
Figure 18B:
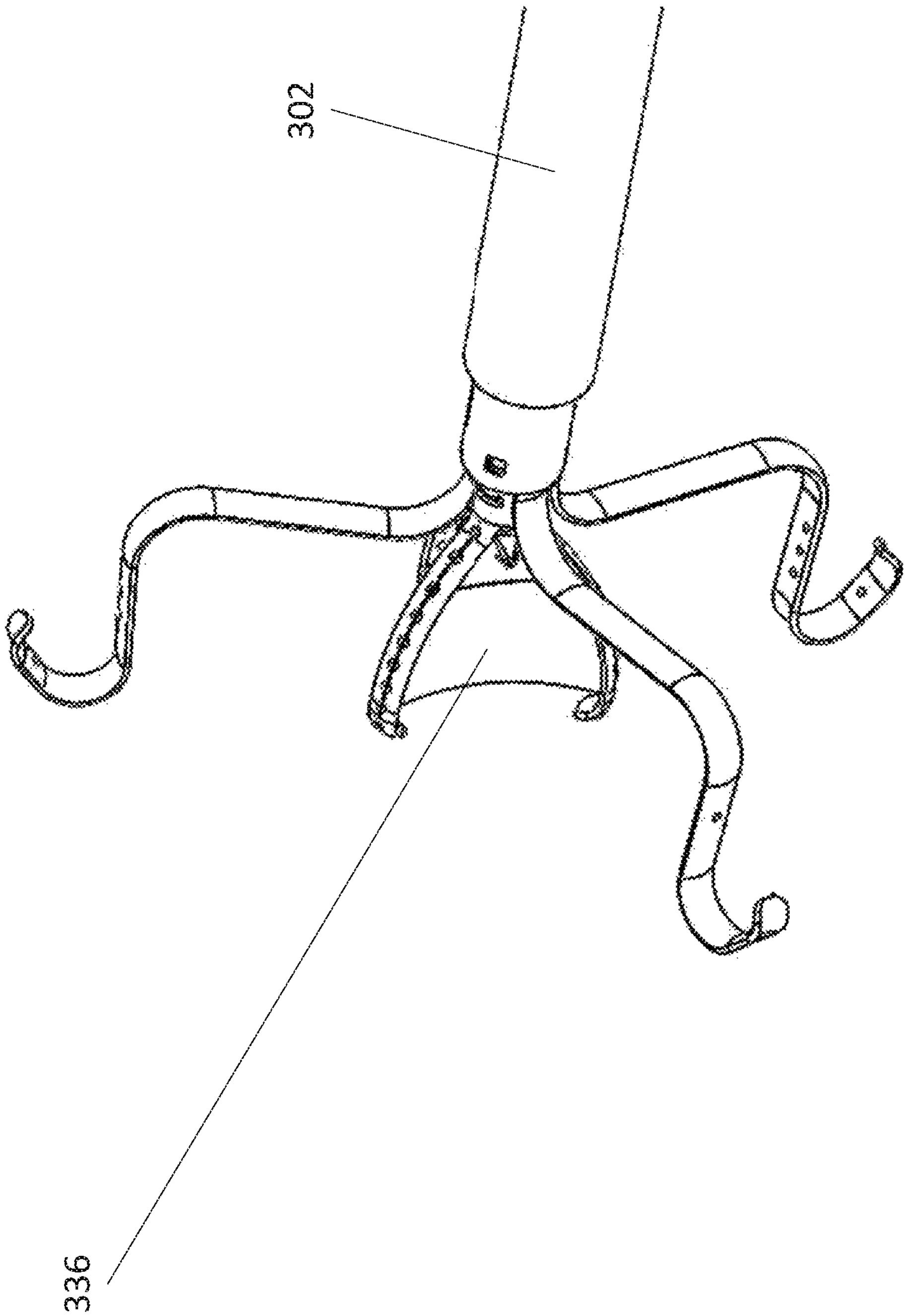
FIGS. 18B and 18C show perspective views of the valve support device being delivered through a catheter.

FIG. 18A shows an embodiment of a tricuspid valve support device 1800 like those described herein. The valve support device 1800 is shown attached to a catheter 302. Before the operative procedure on a patient, the valve support device 1800 is collapsed and positioned within the catheter 1802. As described above, the arms 1804 of the device may comprise a shape memory alloy that can allow the arms to be collapsed for placement in the catheter 1802 and delivery. The catheter is navigated through the vasculature and to the tricuspid valve. The path between the insertion site (e.g., the femoral or jugular vein) and the tricuspid valve is tortuous. As such, the catheter needs to articulate in such a way to navigate the tortuous path.

Figure 19A:
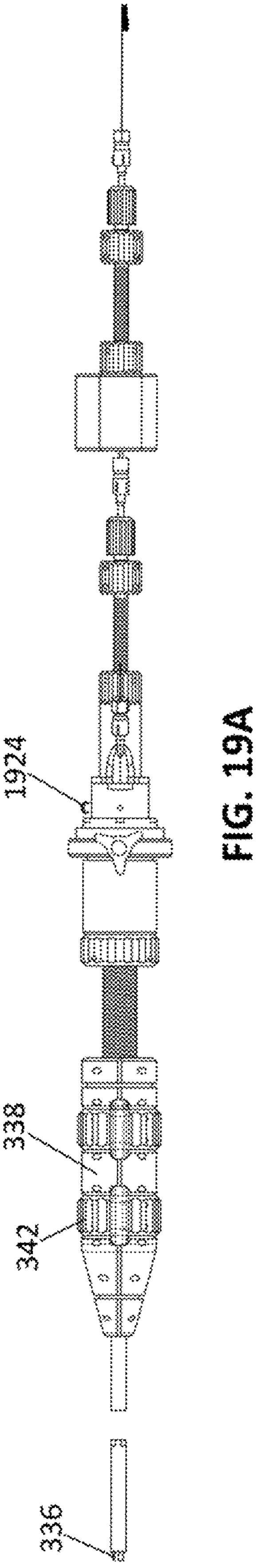
FIG. 19A shows a top view of an embodiment of a delivery system for delivering and adjusting a valve support device.
Figure 19B:
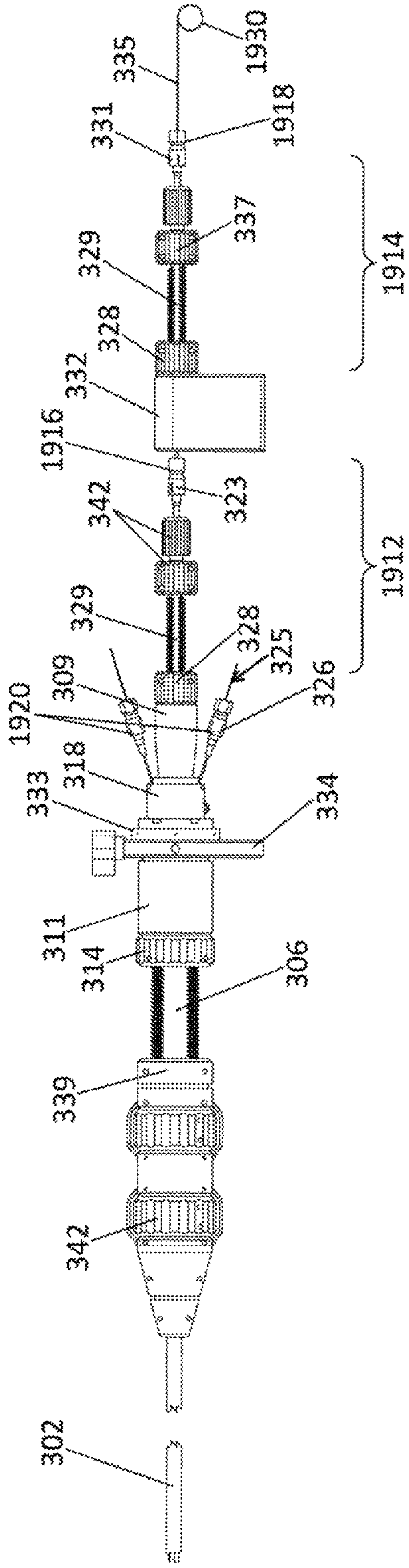
FIG. 19B shows a side view of the delivery system of FIG. 19A.
Figure 19C:
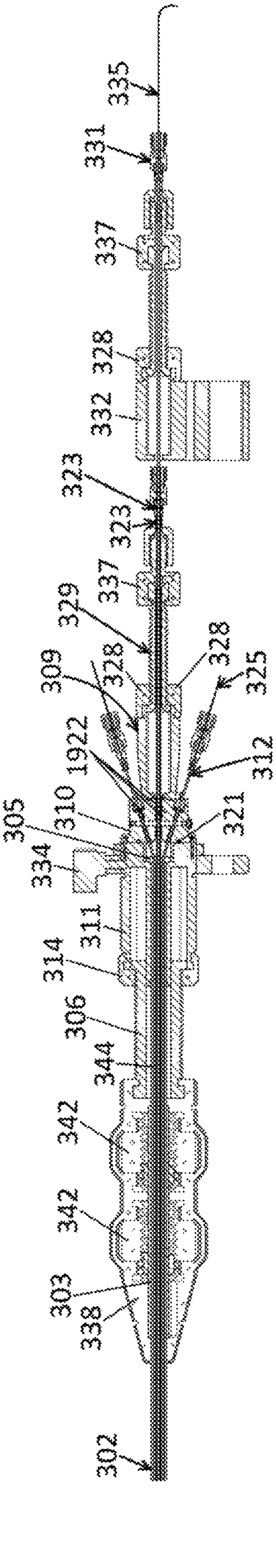
FIGS. 19C and 19D show a side cross-sectional view of the delivery system of FIGS. 19A and 19B.

FIGS. 19A-19C show top, side, and side cutaway views, respectively, of an embodiment of a delivery system 1900 that can be used for controlling the delivery and positioning of the device 1800. Knobs 342 of the delivery system can be used to deflect the catheter 1802 as it navigates the vasculature. In some embodiments, threads inside each knob can mate with exterior threads on an interior deflector element. The deflector element is configured to move forward and backward along a rail 303. The rail keeps the deflector from rotating when turning the knob and limits the deflector elements movement to forward or backward along the rail. The deflector elements are attached to pull wires that run through the catheter 302 and can be used to bend the catheter by pulling or pushing the pull wires.

In some embodiments, the catheter 302 does not include pull wires used to deflect the catheter. In such embodiments, the delivery system 1900 may not include the knobs 342.

Figure 18C:
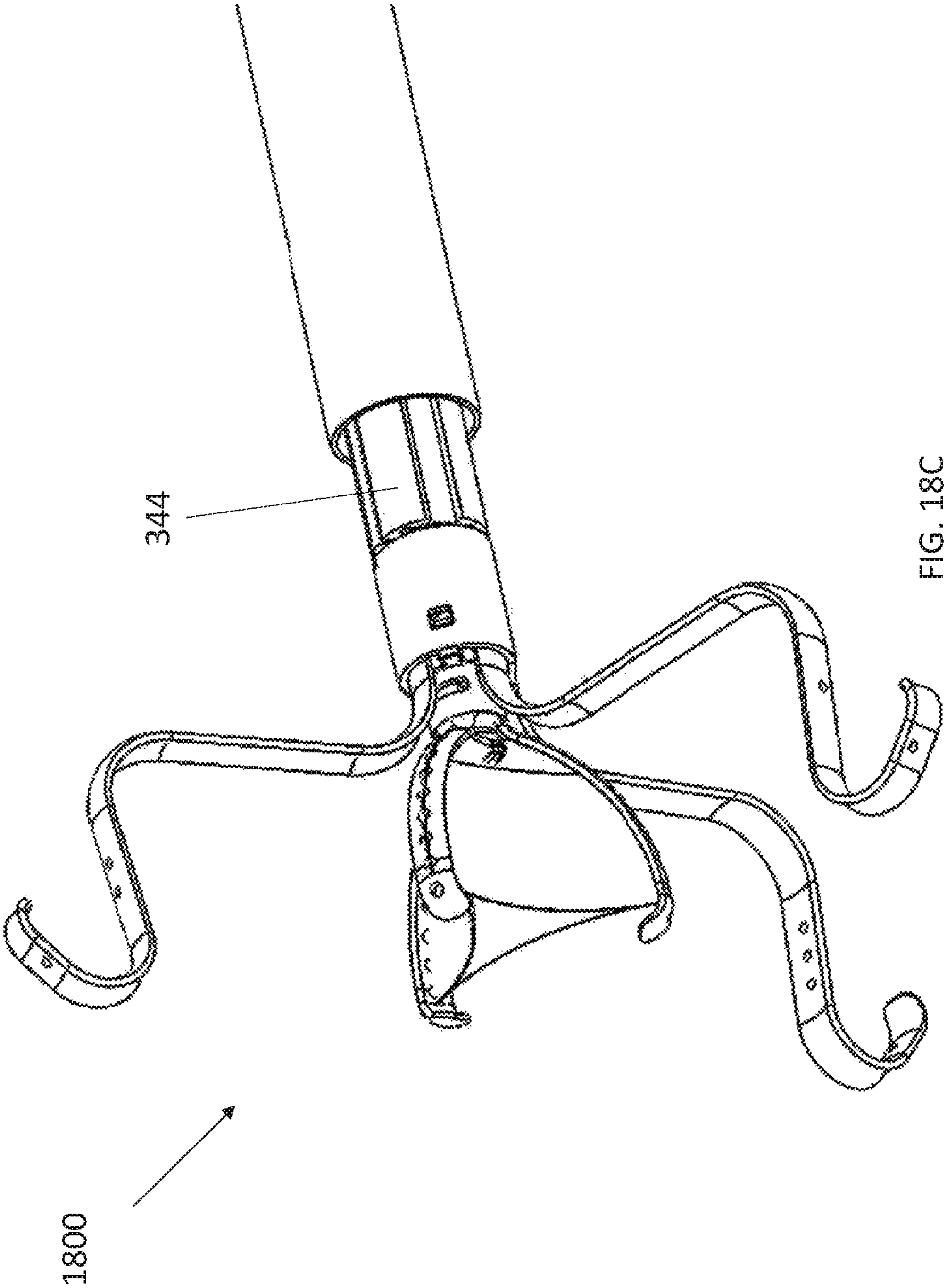

As shown in FIG. 18C, in some embodiments, positioned within the catheter is a multi-lumen shaft 344 attached to the device 1800. The shaft 344 is used to push the device 1800 out of the catheter. Turning knob 314 on the handle can cause the catheter 302 to be pulled backward relative to shaft 344 to unsheathe the implant 1800.

The knob 314 can control an unsheathing screw 306 which can be used to pull the proximal end of the handle distally. As described in further detail below, when the unsheathing screw 306 is in its distal most position, as in FIGS. 19A and 19B, the catheter is fully advanced. The multi-lumen shaft of the catheter butts up against the implant and slowly pushes it out of the catheter.

Figure 19D:
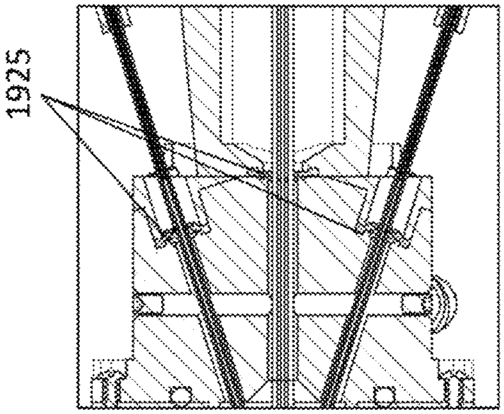
Figure 19E:
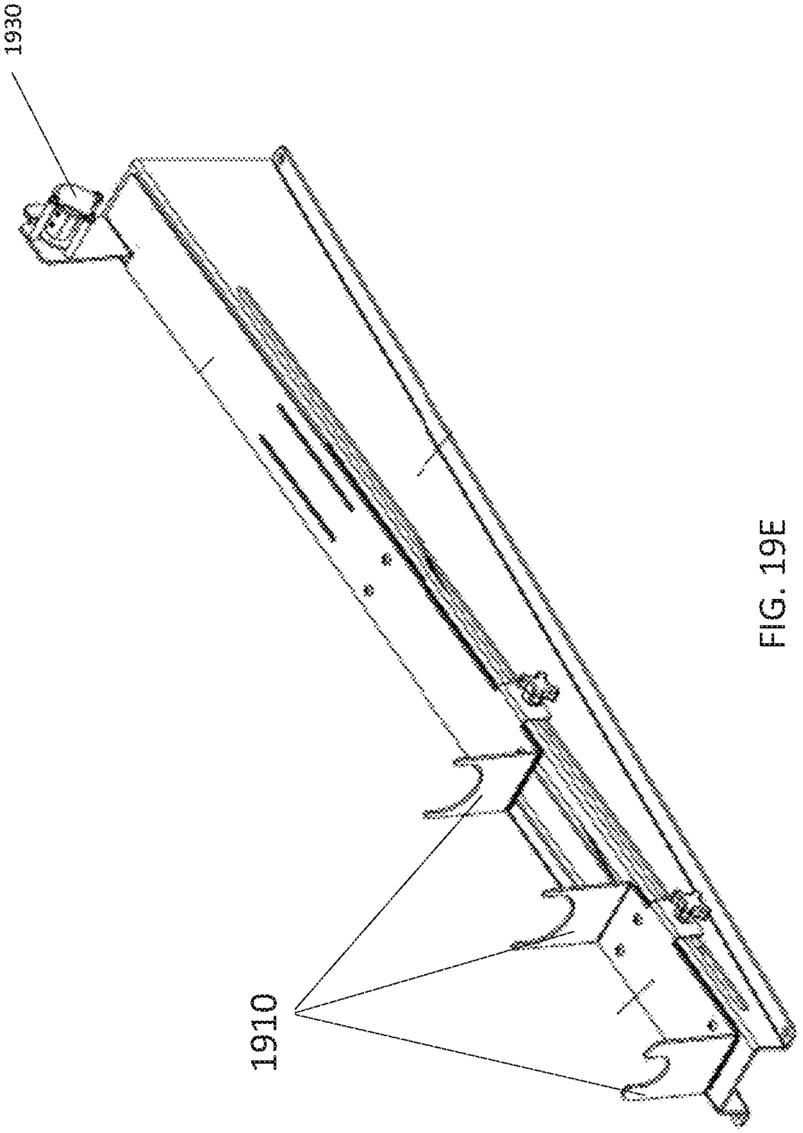
FIG. 19E shows an embodiment of sliding platforms for holding the delivery system of FIGS. 19A-19C.
Figure 19F:
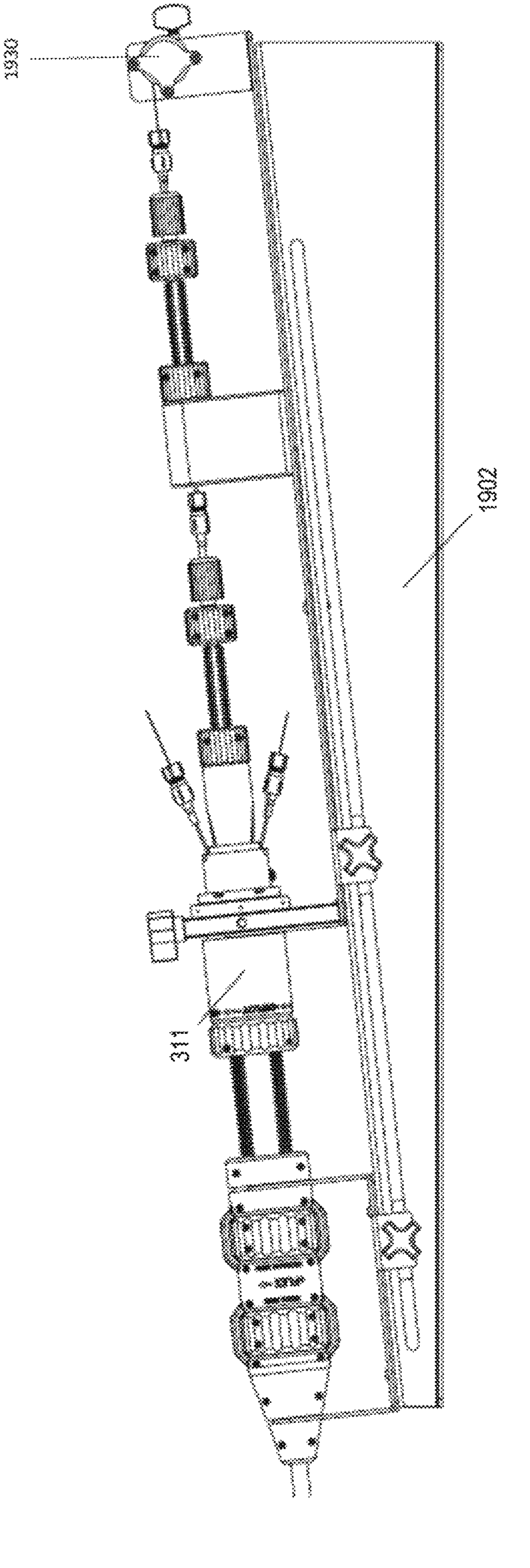
FIG. 19F shows the delivery system of FIGS. 19A-19C positioned on the sliding platforms of FIG. 19D.

To expose the device, the multi-lumen shaft may be kept stationary while the catheter is retracted. Alternatively, the catheter may be held stationary while the multi-lumen shaft is advanced. The multi-lumen shaft is fixed (e.g., attached, glued, etc.) to a portion of the delivery system near the unsheathing screw knob 314. The catheter 302 is fixed to a proximal portion of the delivery system. As shown in FIG. 19D, the delivery system rests on two sliding platforms that help control which portion of the system and device is kept stationary and which is allowed to move. If the distal sliding stage 1902 is locked into place using knob 1904, then turning unsheathing screw 306 will cause the outer catheter 302 to remain stationary and the multi-lumen shaft 344 to advance. If, instead, the proximal sliding stage 1906 is locked using knob 1908, then turning the unsheathing screw 306 will cause the multi-lumen shaft to remain stationary and the outer catheter to retract. Circular cutouts on stand-offs 1910 on the sliding stage can be configured to mate with reciprocating cutouts in the handle as shown in FIG. 19E. This interaction allows the handle to rotate within the cutouts but not translate forward or backward.

The unsheathing can be done in a controlled manner so that the arms 1804 of the device are slowly exposed. This can help avoid a faster opening of the arms and help minimize trauma to surrounding tissues and control the position of the device.

In some embodiments, the exposing of the device 1800 is performed at a general center of the valve. The arms 1804 are gradually brought into contact with the commissures of the valve. Concurrent imaging of the valve (e.g., using fluoroscopy or echocardiography) can be used to confirm proper positioning of the implant. Rotation of the catheter can be used to rotate the valve and properly position the arms within the valve. In embodiments in which the arms have been previously angled, alignment of only one arm with the valve is required to ensure proper positioning of the implant within the valve.

Referring again to FIG. 19B, in some embodiments, once the clinician is satisfied with the rotational position of the device, locking mechanism 334 that encircles the delivery system can be used to lock the rotation of the handle relative to the mounting stage. So, when a clinician is rotating the implant to make sure anchoring arms are lined up, the lock 334 can be released. Once satisfied with rotational orientation, the lock can once again be activated.

In some embodiments, the device may be deployed in such a way as to individually control the release or expansion of each arm. Each arm can be connected to a loop of material. Each loop can be individually controlled to allow it to expand radially outward (e.g., to release the arm) or to move it radially inward (e.g., to recapture the arm).

The loop material can be in line with the arms (e.g., distal end of arms) or hooks on the arms. The loop material can loop around each arm and extend back through the multi-lumen shaft to the loop control portion of the delivery system.

The arm control loops can advantageously allow full deployment of the device without expanding the arms. The arm loops can maintain the compressed form outside of the sheath until the physician is satisfied with the placement. The physician can rotate the arms while they are compressed. Additionally, because the loop allows you to control the distal end, rather than trying to control from the proximal end of the arm, the loop provides good control over the arm movement (e.g., as compared to trying to control the arm from a more proximal position on the arm or catheter).

The arm loops can allow the arms to be opened to any intermediate position between fully compressed and fully deployed (e.g., ½ open, ¾ open, etc.)

Figure 36:
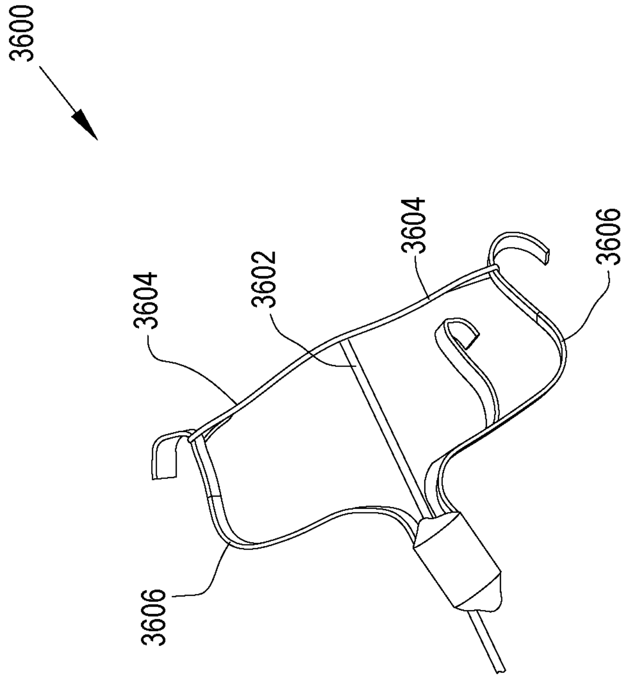
FIG. 36 shows a perspective view of an embodiment of a valve support device with loops extending from a loop shaft to the arms.

FIG. 36 shows an embodiment of a device 3600. The device 3600 is similar to device 1800, unless otherwise described. A shaft 3602 that is part of the delivery system extends through the multi lumen shaft of the device 3600. The shaft 3602 comprises at least one lumen to allow passage of the loop material (e.g., suture). The shaft 3602 can comprise one or more apertures to allow each loop 3604 to exit the shaft and be looped around each arm 3606.

The arm loops can also be used to recapture the arms during delivery. Pulling on the arm with the loops can bring the arm(s) into the compressed position. Recapturing the arms can be used for repositioning or withdrawal of the device.

FIGS. 37A-37E show embodiments of a distal end of a loop shaft that can be used to carry the loop material from the handle to the device. The distal portion of the loop shaft can be formed integrally with the shaft. In some embodiments, the distal portion of the loop shaft comprises a separate fitting that can be attached to the shaft 3602. For example, the distal portion can be press fit or bonded or welded to the shaft 3602.

Figure 37B:
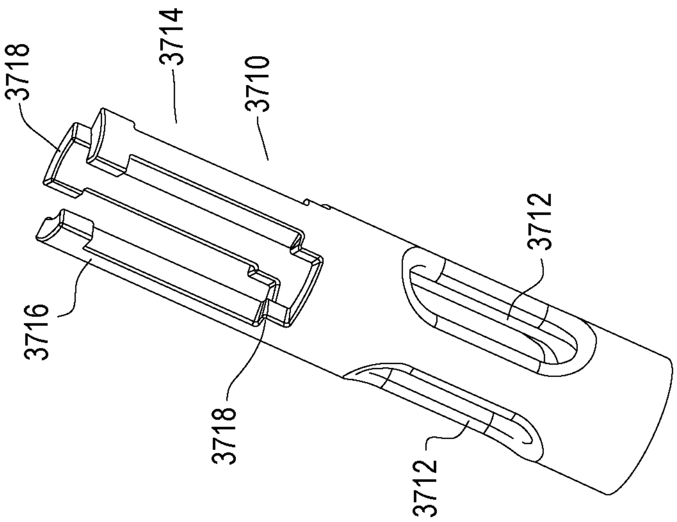
FIGS. 37A-37I show various embodiments of distal ends of loop shafts.
Figure 37A:
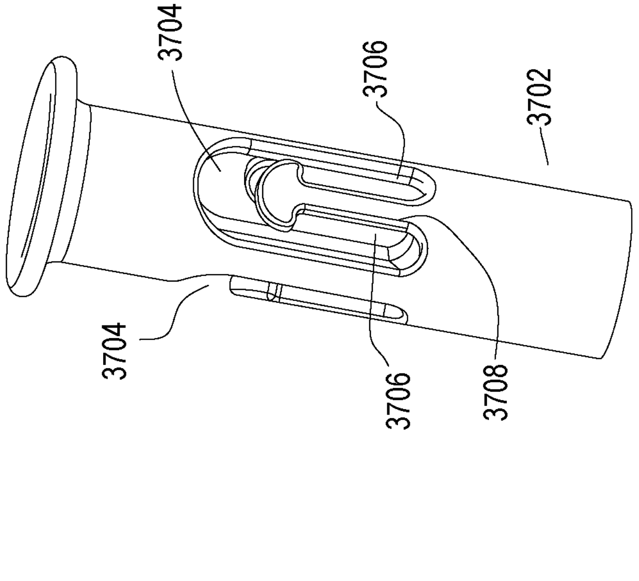

FIG. 37A shows an embodiment of a loop shaft 3702 or a distal fitting of a loop shaft. The loop shaft 3702 comprises a hollow lumen to allow passage of the loop material therethrough. The loop shaft 3702 comprises three apertures 3704 to allow egress of the loop material. The aperture comprises a width allowing for spacing three apertures allow a circumference of the loop shaft 3702. For example, each aperture 3704 may comprise a width of about 10-30% of the loop shaft circumference. Each aperture may comprise a height adequate to allow the free insertion and translation of the loops within the apertures.

Each aperture 3704 comprises a first section 3706 and a second section 3706 separated by a mid portion 3708 comprising a side of the loop shaft 3702. For each loop, the loop material may extend through the first section 3706, loop around its respective arm and return to the loop shaft 3702 through the second section 3706. In some embodiments, each strand of material may comprise its own aperture. In some embodiments, both strands of a loop may exit the shaft through the same portion of an aperture. The edges of the apertures 3704 can be rounded, which can advantageously reduce the risk of cutting the loop material.

FIG. 37B shows another embodiment of a distal end of a loop shaft 3710 or a distal fitting of a loop shaft. The shaft comprises three apertures 3712 spaced around the loop shaft 3710. The apertures 3712 are proximal to a distal portion 3714 of the shaft 3710. The apertures comprise a width allowing for spacing three apertures around a circumference of the loop shaft 3710. For example, each aperture 3704 may comprise a width of about 10-30% of the loop shaft circumference. In some embodiments, the apertures comprise a generally ovular shape extending along a longitudinal axis of the shaft. The shaft comprises an end portion wherein the sidewalls of shaft transition to three prongs 3716. The prongs 3716 may by formed by removing material from the sidewalls of the shaft at the distal portion (e.g., laser cut). In some embodiments, the prongs 3716 are added to the shaft 3710 at the distal portion. Each prong can have a wide portion 3718 at its base and at its end. In some embodiments, each loop can loop around a prong to keep the loop in place until withdrawal is desired.

Figure 37D:
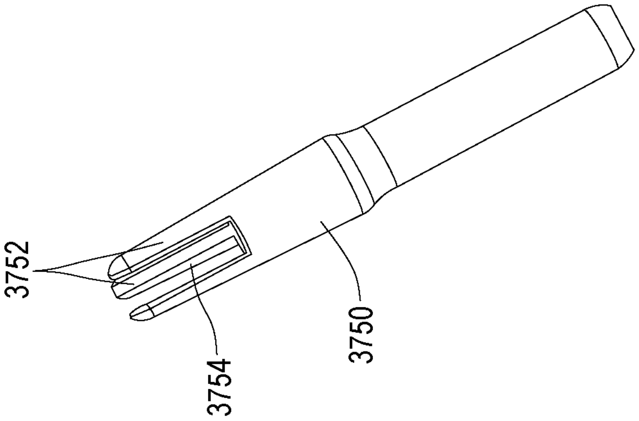
Figure 37C:
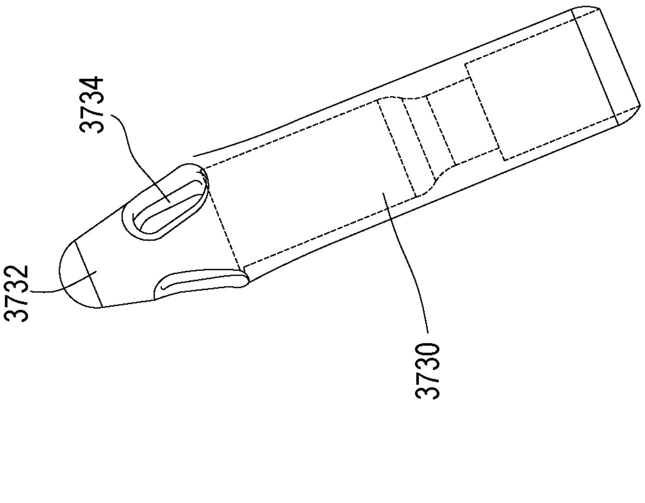

FIG. 37C shows another embodiment of a distal end of a loop shaft 3730 or a distal fitting of a loop shaft. The loop shaft 3730 comprises a tapered and rounded atraumatic tip 3732. The shaft comprises three apertures 3734 spaced around a portion of the shaft proximal to the distal tip. The apertures 3734 comprises rounded edges so as to minimize friction between the loops and the shaft 3730.

FIG. 37D shows another embodiment of a distal end of a loop shaft 3750 or a distal fitting of a loop shaft. The loop shaft 3750 comprises a distal tip comprising three prongs 3752 with rounded, atraumatic tips. The loops are configured to exit the shaft 3750 through the openings 3754 between the prongs 3752.

Figure 37F:
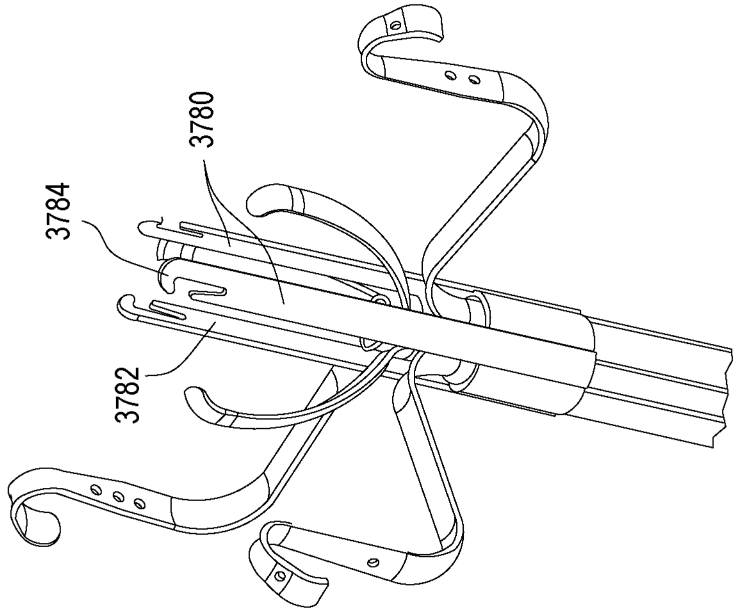
Figure 37E:
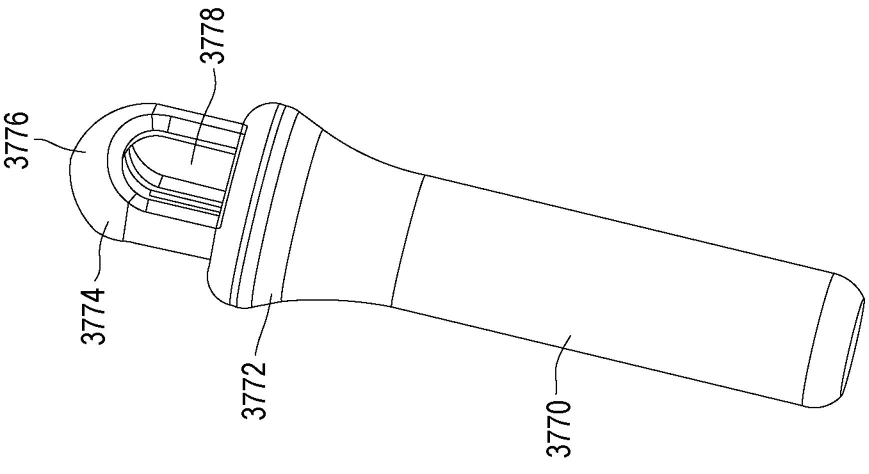

FIG. 37E shows another embodiment of a distal end of a loop shaft 3770 or a distal fitting of a loop shaft. The shaft 3770 comprises a flared portion 3772 towards its end. The flared portion 3772 extends from a smaller diameter to a larger diameter as it moves distally. The flared portion 3772 comprises rounded edges. The flared portion can help to reduce friction between the loops and the shaft 3770. A knob 3774 extends from the flared portion 3772 at a distal end of the shaft 3770. The knob comprises an atraumatic tip (e.g. rounded distal end) 3776, which can help to prevent tissue trauma. The knob comprises three apertures 3778 spaced around a circumference of the knob 3774. The apertures 3778 can comprises generally straight sidewalls extending upwards to a rounded top portion (e.g., U-shaped). The edges of the apertures 3778 can be rounded.

FIG. 37F shows an embodiment in which a separate loop shaft 3780 is used for each loop. Each shaft may comprise a groove 3782 and hook feature 3784 at the end of the shaft 3780. The groove feature 3782 can be used to guide the loop as it moves from an inner surface of the shaft 3780 towards the arm. The rounded hook feature 3784 can help provided an atraumatic tip to reduce tissue trauma.

Figure 37H:
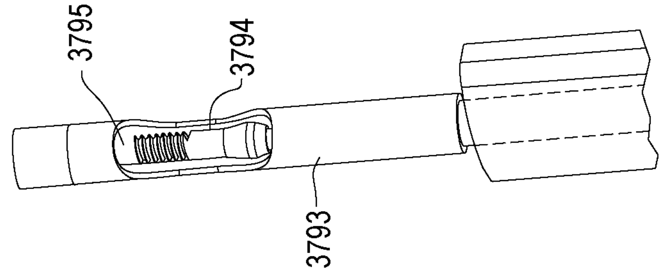
Figure 37G:
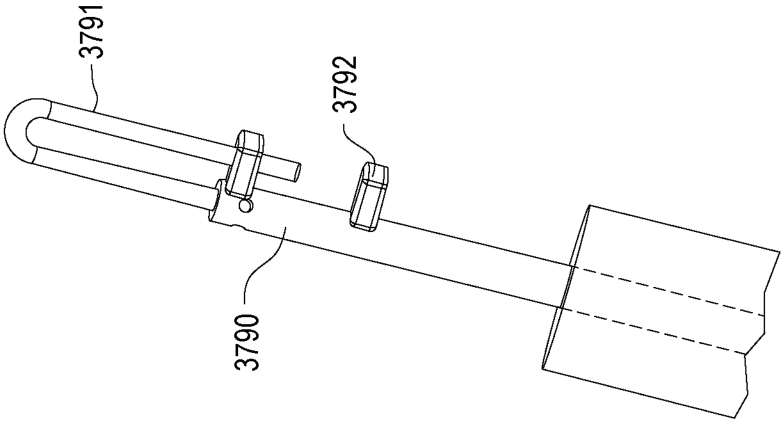
Figure 37I:
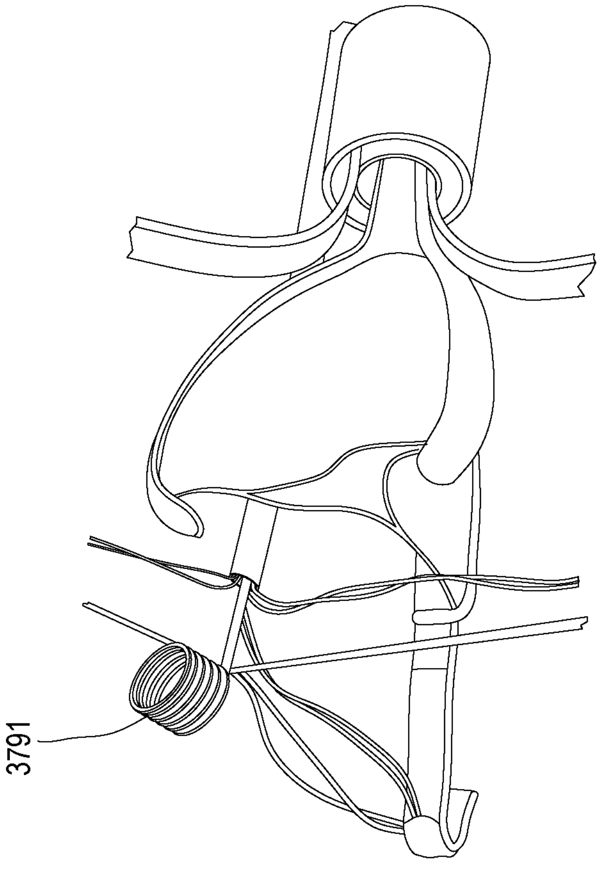

FIG. 37G shows another embodiment of a distal end of a loop shaft 3790. The loop shaft 3790 comprises a pin 3791 configured to be received by aperture 3792 and be moved distally so as to be released from aperture 3792. The pin 3791 is configured to secure the loops when the pin 3791 is positioned within the aperture 3792.

FIG. 37H shows another embodiment of a distal end of a loop shaft 3793. The shaft comprises an aperture 3794. A wire 3795 that extends within the shaft 3793 is shown within the aperture 3794. In some embodiments, the shaft 3793 can comprise more than one aperture (e.g., 2 apertures, 3 apertures, etc.).

Optionally, the wire 3795 can have threads at the distal end that can secure its position within the shaft 3793 by mating with corresponding threads on the inner surface of the shaft 3793.

The loops are configured to be looped around the wire 3795. To release the loops, the wire 3795 can be pulled proximally.

In some embodiments, as shown in FIG. 37 I the distal end 3796 of the wire is coiled or looped or bunch or otherwise manipulated to have a diameter greater than that of the opening of the shaft 3793 to prevent inadvertent release of the loops. Upon application of sufficient force, the greater diameter end of the wire can be pulled proximally into the shaft to release the loops.

Figure 38B:
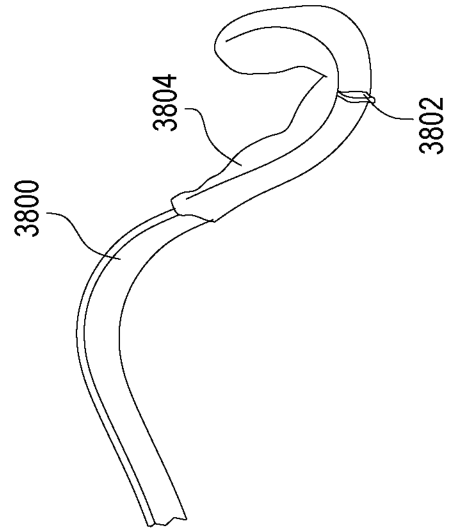
FIGS. 38A and 38B show embodiments of hoops on arms of a valve support device configured to support a loop.
Figure 38A:
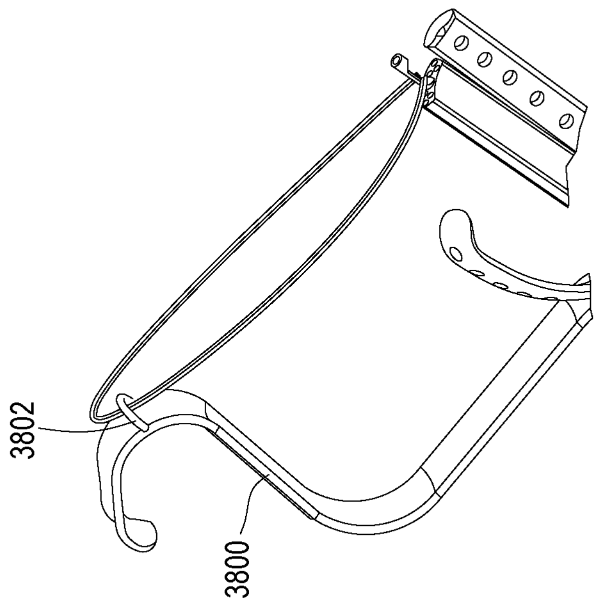

FIGS. 38A and 38B show embodiments of an arm 3800 comprising a hoop 3802 for stabilizing the loop material. FIG. 38A shows a hoop positioned on the arm 3800 at a hook like portion of the arm. FIG. 38B shows another embodiment of a hoop 3802 positioned on an arm. In this embodiment, the hoop is positioned on a covering 3804 that is on the arm in the portion surrounding the hoop. The covering may help keep the hoop in position.

The loop material can be looped around pulley rods in the loop control portion of the delivery system. The pulley rods can be controlled by knobs that allow for tightening or loosening of each loop. FIG. 39A shows an embodiment of a loop control portion 3902 comprising apertures 3904 configured to receive each pulley rod. The pulleys can be arranged somewhat vertically as shown here in order to minimize the amount of space the loop control portion 3902 takes on the handle.

Figure 39B:
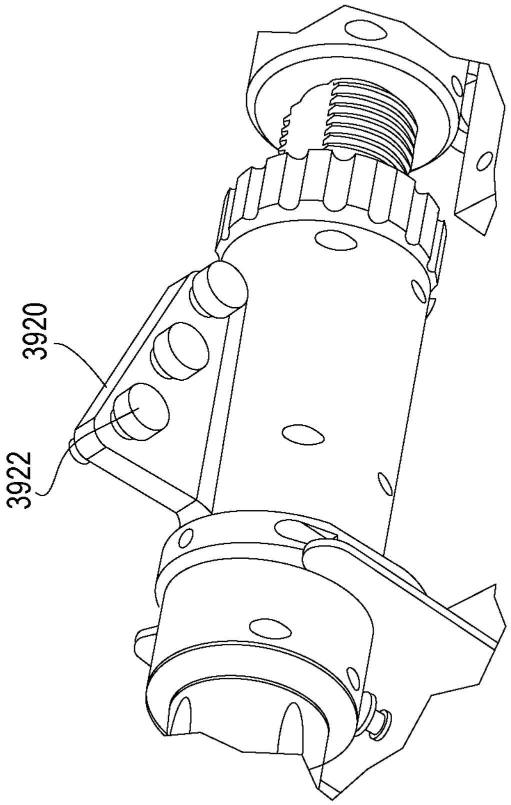
FIGS. 39A-39C show various embodiments of a control section for arm control loops.
Figure 39A:
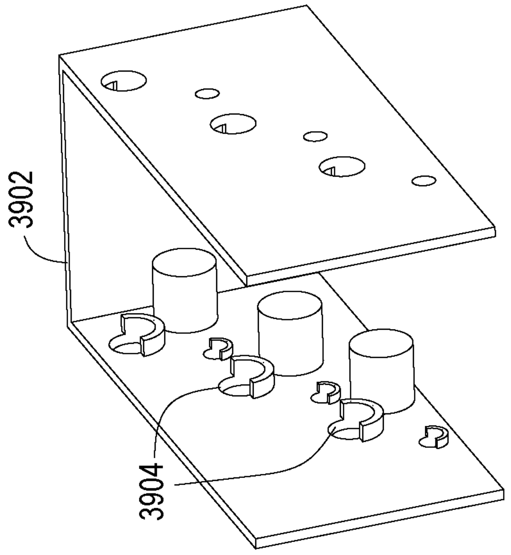

FIG. 39B shows another embodiment of a loop control portion 3920 of a delivery system. The loop control portion 3920 is configure as a fin with an increasing height as it moves proximally. Each knob 3922 and corresponding pulley is arranged at a different height from the handle, thereby minimizing the amount of space the loop control portion 3920 takes.

Figure 39C:
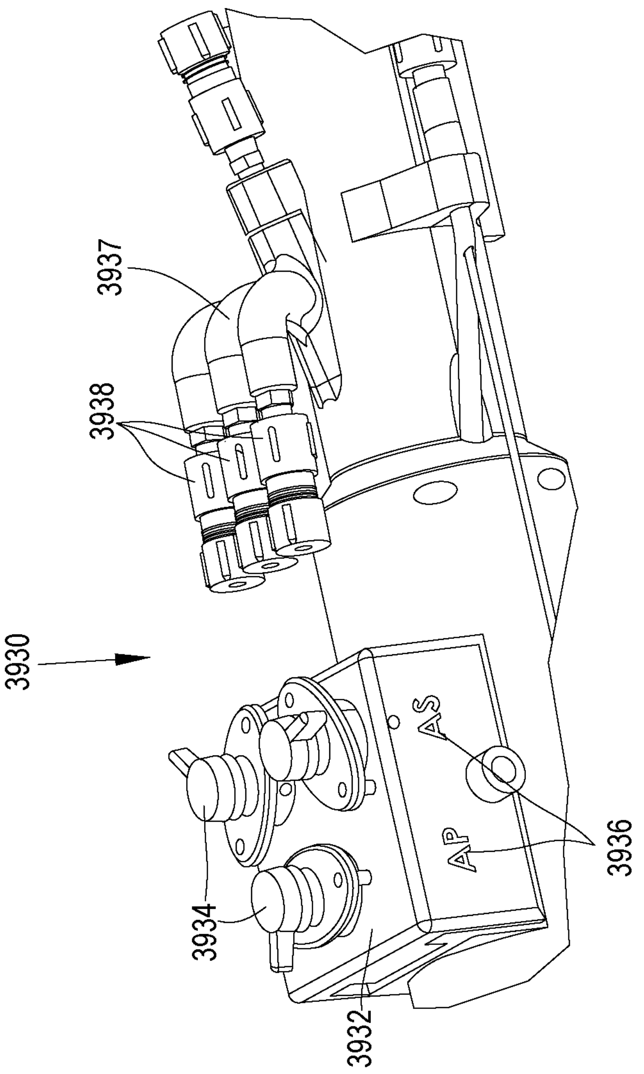

FIG. 39C shows another embodiment of a loop control portion 3930 of a delivery system. The loop control portion 3930 comprises a frame 3932 comprising 3 control knobs 3934, one corresponding to each loop. The knobs 3934 are positioned generally concentrically, in a configuration intended to represent the position of the arms each knob controls. The loop control frame 3932 can also comprise labels 3936 to specify which knob controls the opening/closing of the correspondent arm of the device (e.g., device 700, 1600, 1700, etc). This configuration provides an intuitive system for a clinician to use.

The loop control portion 3930 comprises of a manifold 3937 and three ports 3938 configured to separate the loops as they exit the loop shaft and align them with their respective knobs 3934.

In some embodiments, the loop control portion can comprise gears to provide more precise control over the loops. For example, a desired number of turns of the knob can result in a desired movement of the arms.

In some embodiments, the knobs can be removeable from the delivery system.

Figure 20A:
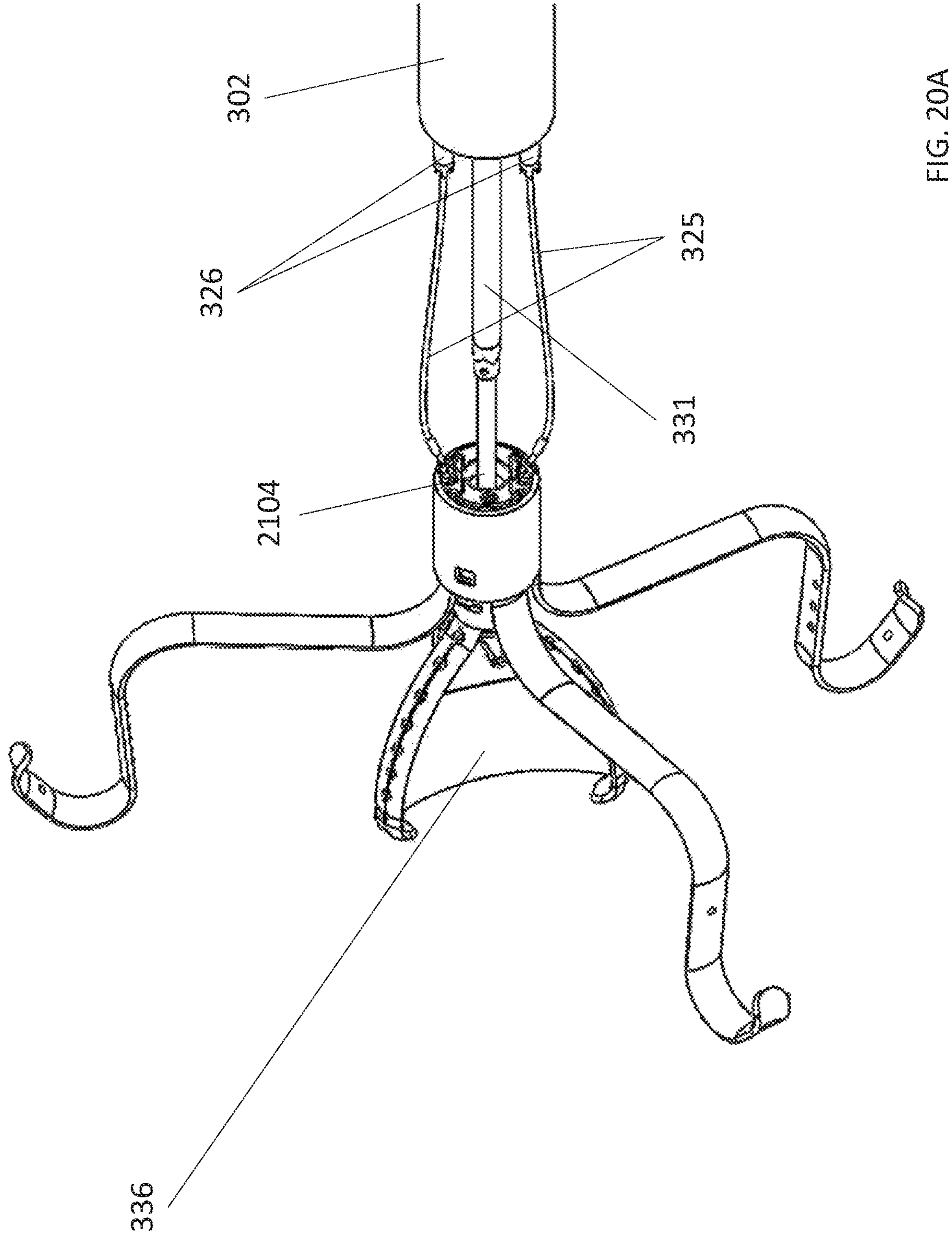
FIG. 20A shows a perspective view of an embodiment of an adjustment member extending from the catheter towards the device of FIG. 18A-18B.
Figure 20B:
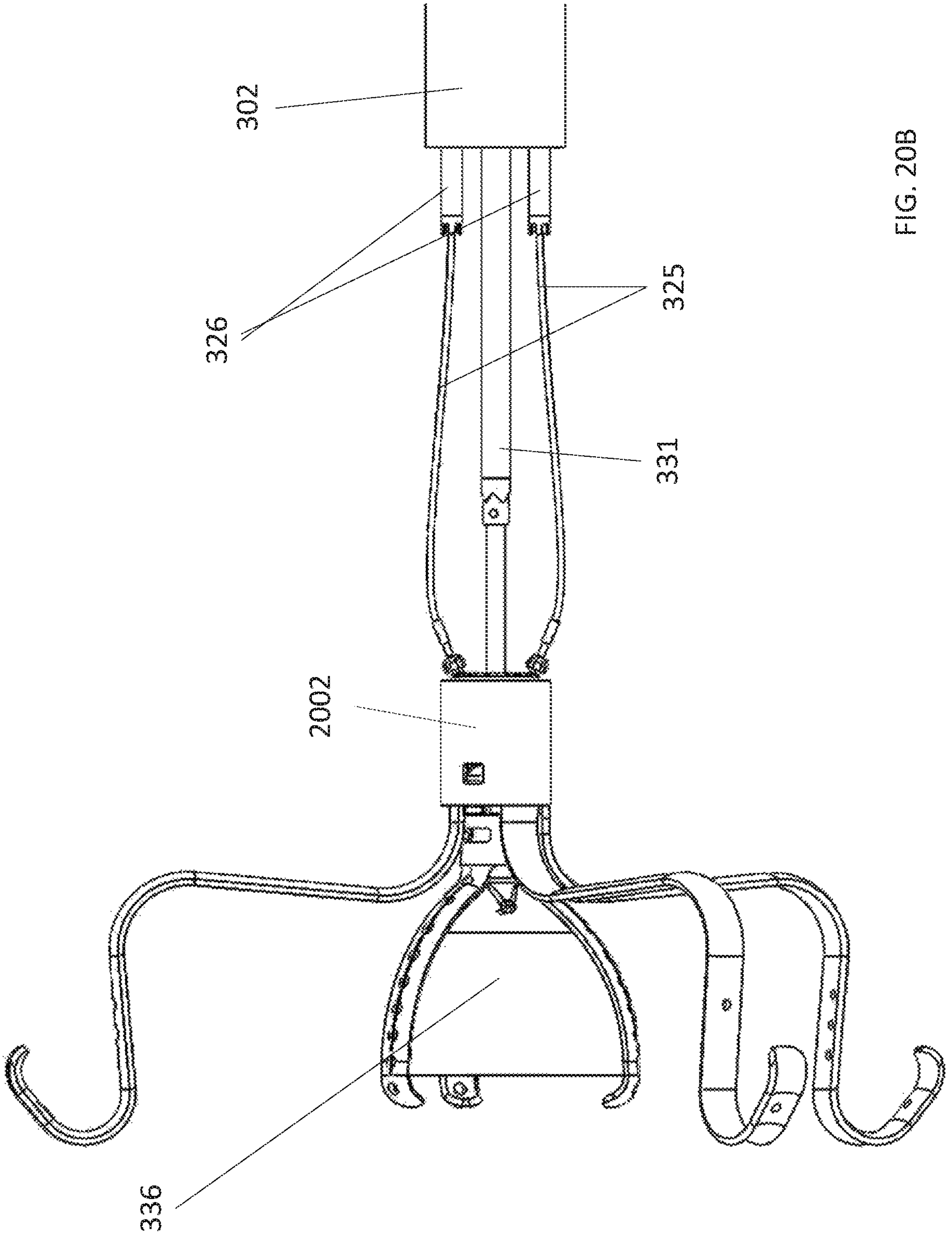
FIG. 20B shows a side view of the adjustment member extending from the catheter towards the device.
Figure 20C:
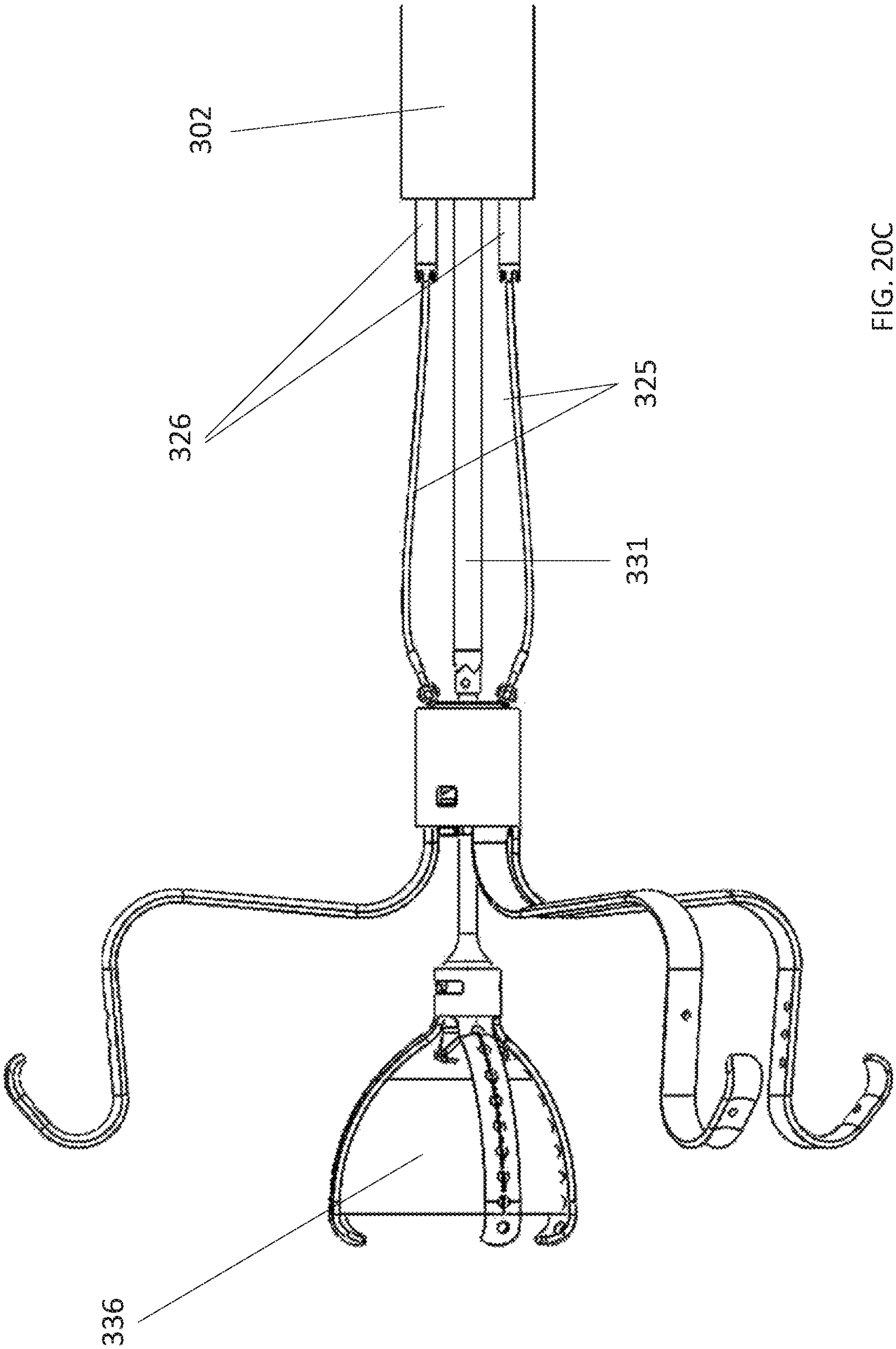
FIG. 20C shows a side view of the adjustment member translated distally so that it is positioned against the device.

Referring now to FIGS. 20A-20C, once the device is locked into the valve commissures, the catheter 302 is retracted slightly to allow for adjustment of the flow optimizer shaft 2104, as shown in FIG. 20A. Retracting the catheter 302 exposes a flexible adjustment member 331 (e.g., tube) that extends from the catheter. The adjustment member 331 can be responsible for adjusting a height and rotation of the flow optimizer.

Figure 22A:
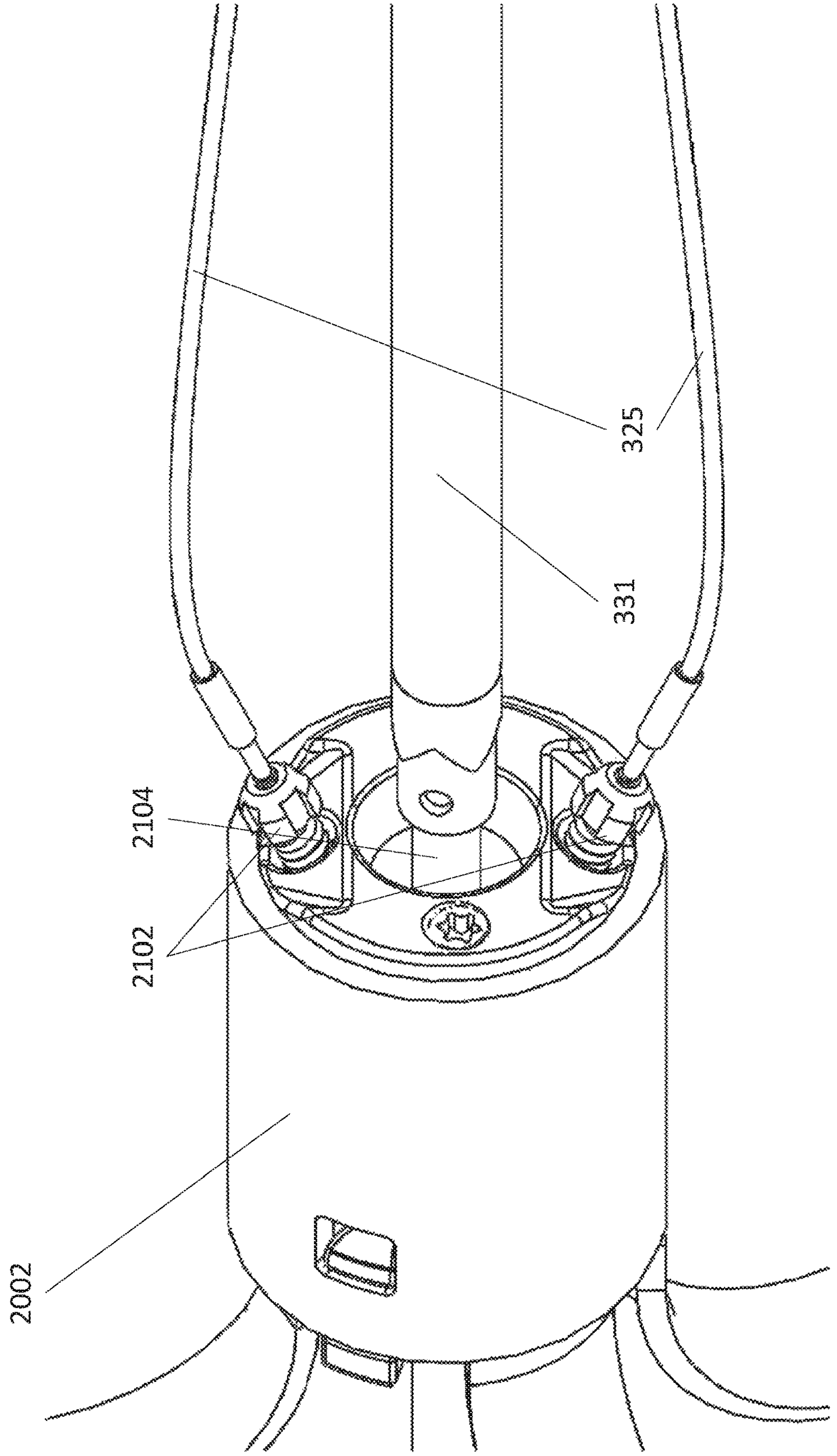
FIG. 22A shows a detailed view of an embodiment of screw guidewires extending to the device of FIGS. 18A and 18B.
Figure 22B:
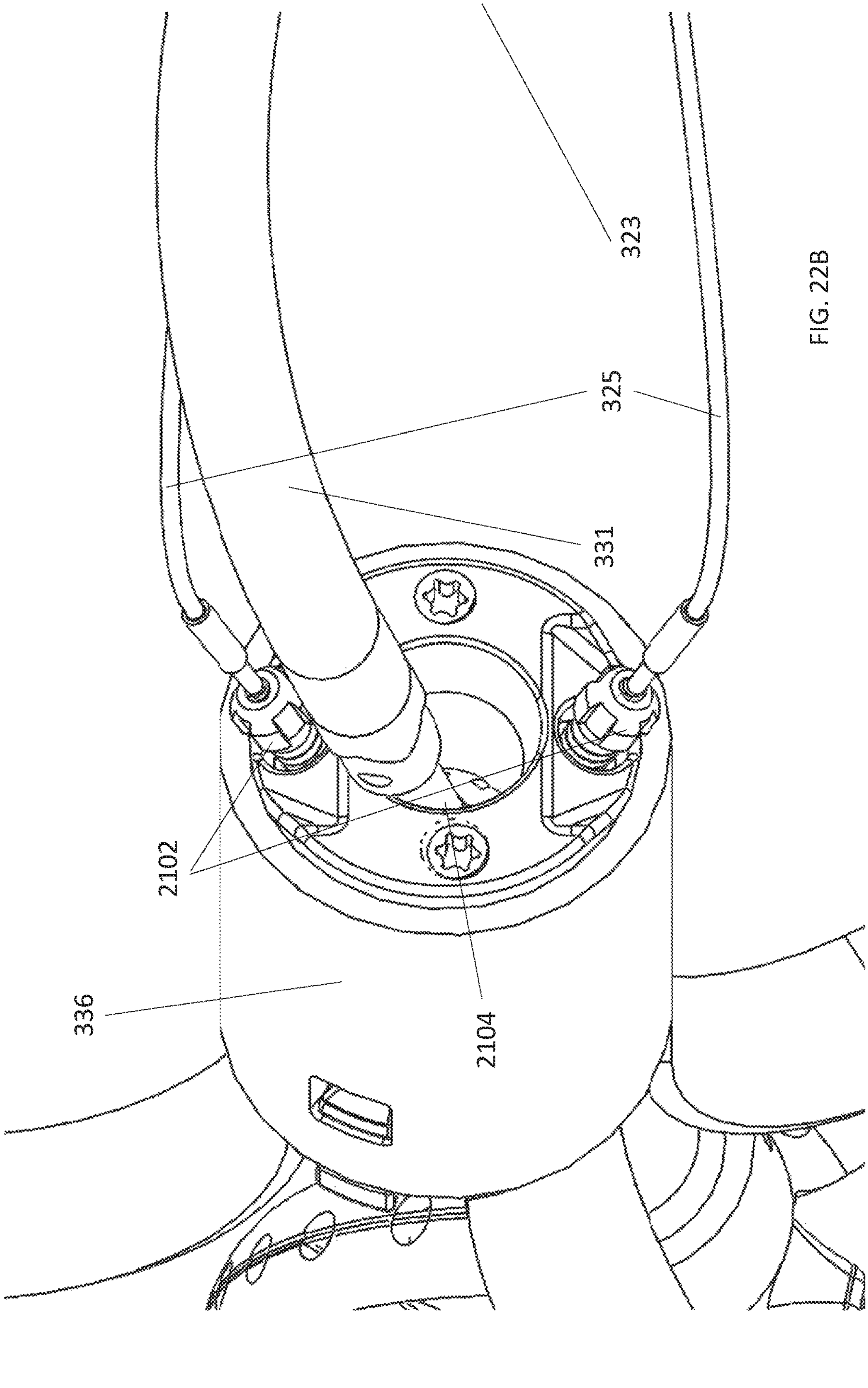
FIG. 22B also shows a detailed view of screw guidewires extending to the device when an adjustment member is in a bent configuration.
Figure 22C:
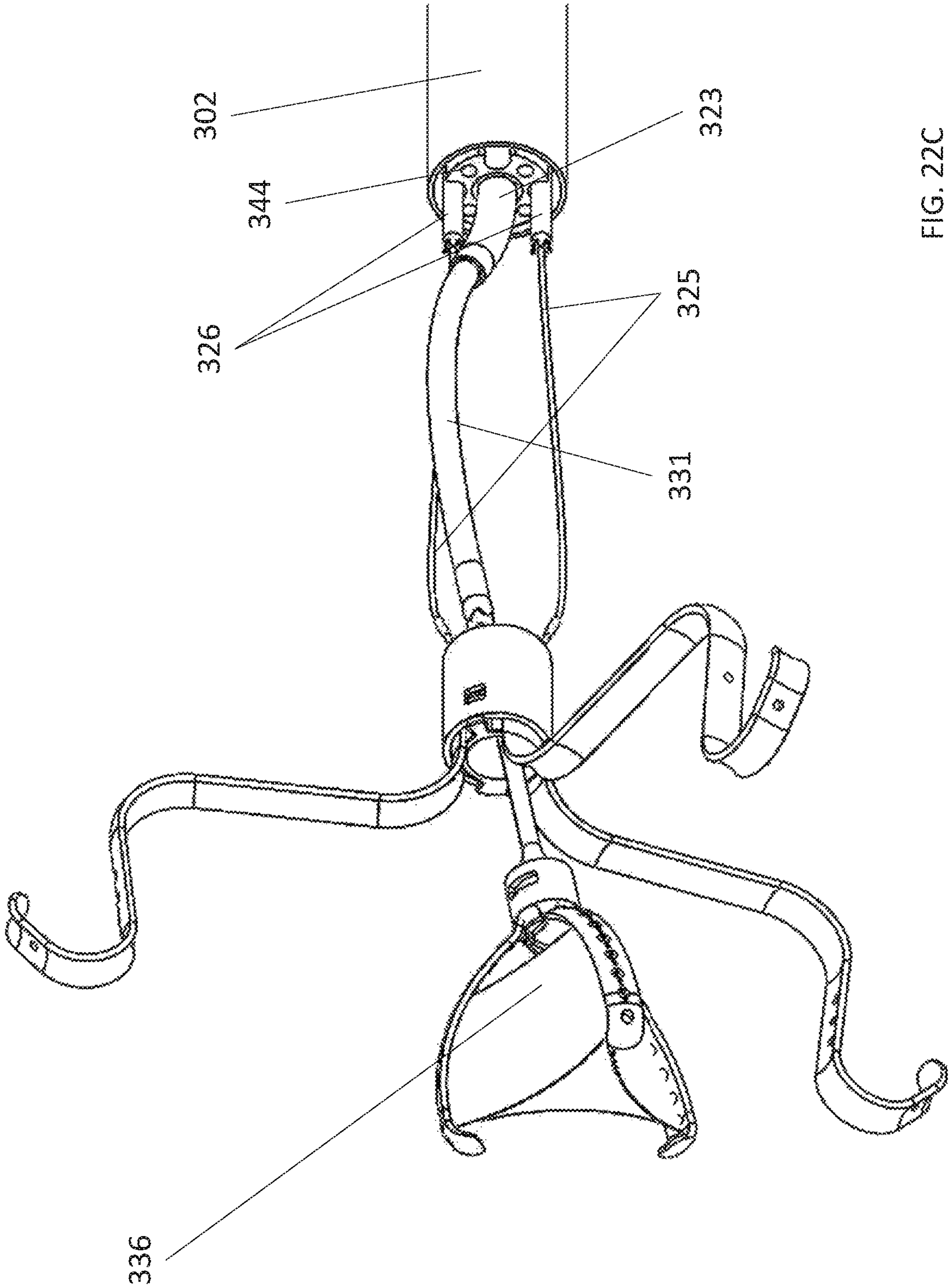
FIG. 22C shows a perspective view of screw guidewires extending from the catheter towards the device of FIGS. 18A and 18B.
Figure 22D:
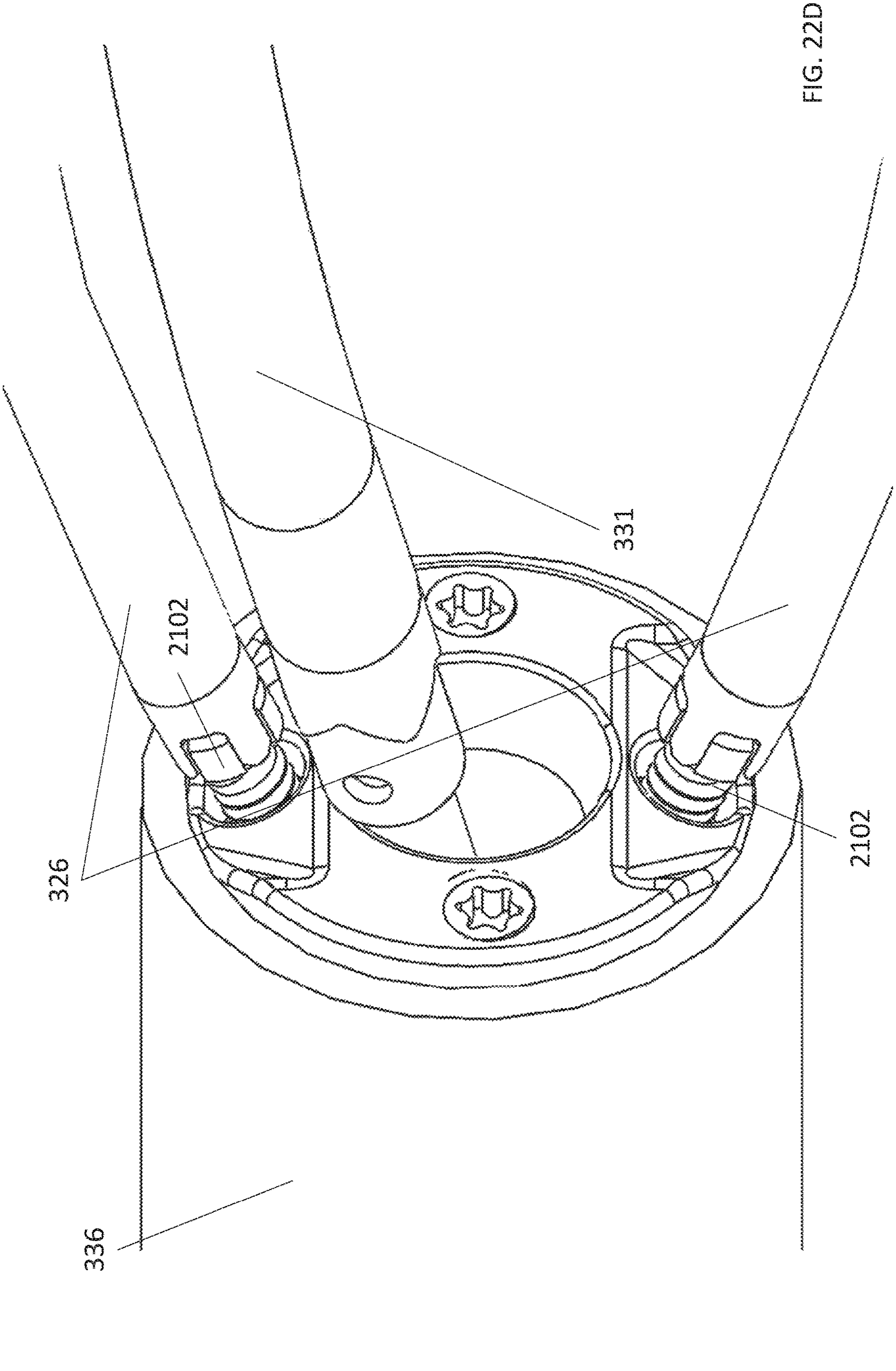
FIG. 22D shows a detailed view of exemplary torqueing tubes extending over the screw guidewires of FIGS. 22B and 22C.
Figure 22E:
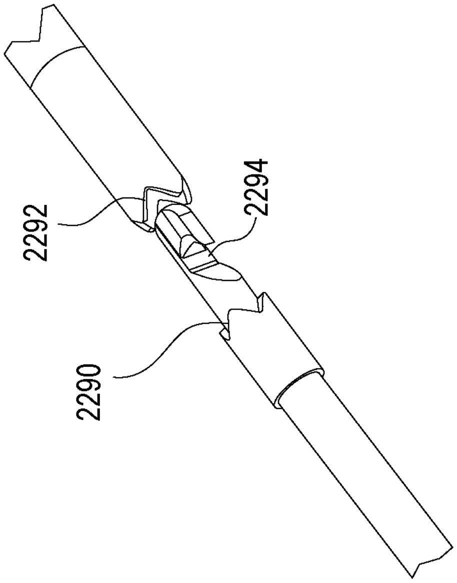
FIG. 22E shows a detailed view of an embodiment of interaction of a device shaft with the adjustment member.

As shown in FIG. 22E, a distal end of the shaft 2104 has features 2290 configured to interact with features 2292 on a distal end of the adjustment member 331.

A wire (e.g., braided wire) can extend through the flexible member and can help keep the adjustment member 331 in tension, helping to keep the flexible member 331 and the flow optimizer butted up against one another. The wire hooks onto hook 2294 of the shaft 2104. The shaft 2104 and the adjustment member 331 can be advanced and retracted with respect to the anchoring assembly 2002, as shown in FIGS. 20B and 20C. This adjustment can adjust the height of the flow optimizer 336 with respect to the anchoring assembly 2002. Rotating the flexible member can control the rotational position of the flow optimizer with respect to the anchoring assembly 2002.

Figure 21:
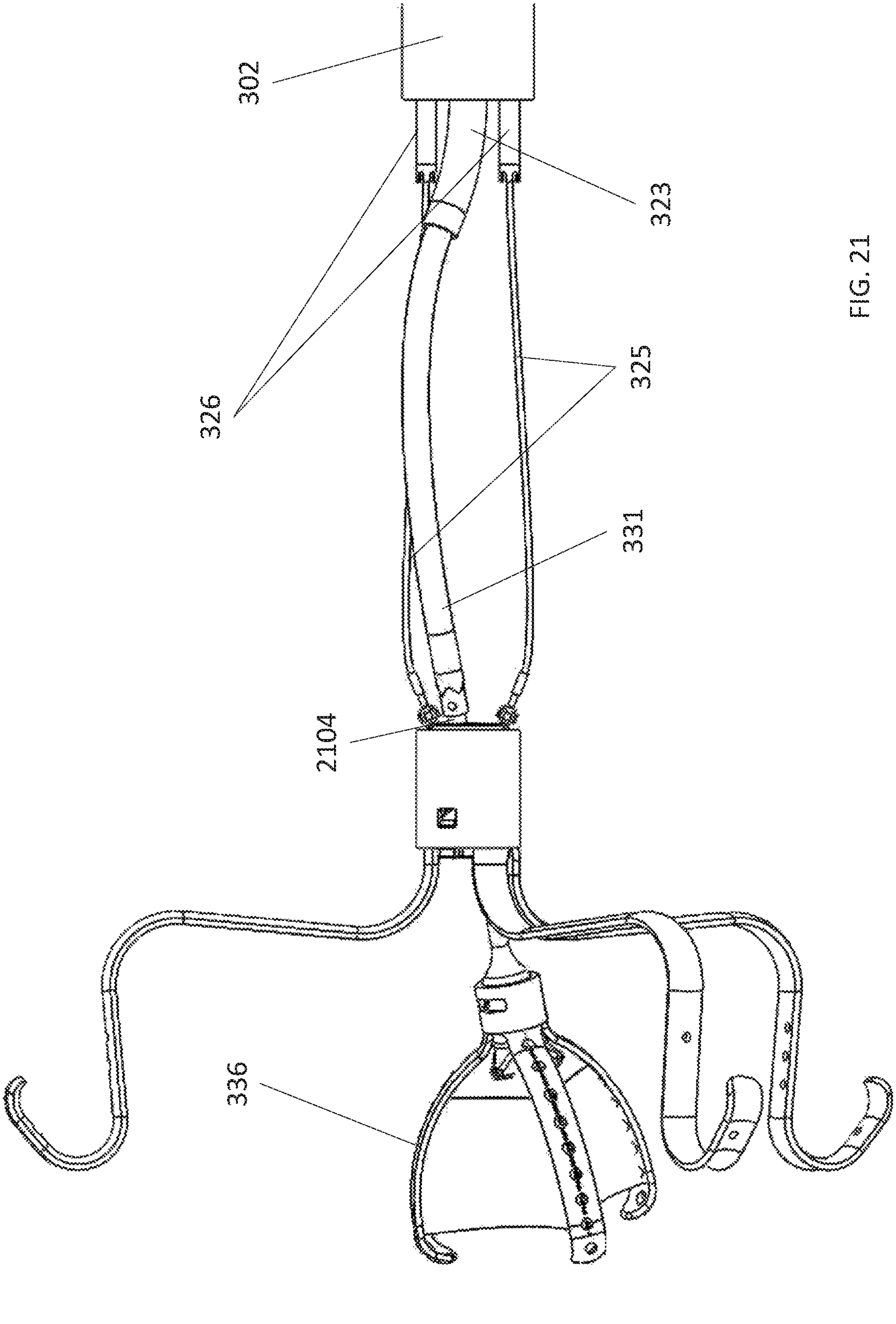
FIG. 21 shows a perspective view of an embodiment of a tilt adjustment member extending from a catheter towards the device of FIGS. 18A-18B.

Referring now to FIG. 21, the tilt of the flow optimizer with respect to the anchoring assembly 2002 is also adjusted. A tilt adjustment member 323 (e.g., tube) overlaps and is concentric with adjustment member 331. The tube 323 has a bend towards its distal end. When the tilt adjustment member 323 is fully retracted and contained within the catheter 302, it is generally straight. When it is exposed, the tilt adjustment member 323 biases towards its bent shape, shown in FIG. 21. The tilt adjustment member 323 bending causes adjustment member 331 to bend, tilting the flow optimizer with respect to the anchoring assembly 2002. Rotating the bent adjustment member 331 can adjust the orientation of the flow optimizer tilt. In other words, rotating the bent flexible member can adjust the portion of the anchoring assembly towards which the flow optimizer tilts. Adjusting the length of the exposed portion of tilt adjustment member 323 can adjust the degree of bend in the flexible member 331. Adjusting the degree of bend in the flexible member can adjust the degree of tilt of the flow optimizer.

It will be appreciated that other mechanisms for bending flexible member 331 to control the tilt of the flow optimizer are also contemplated (e.g., those described below with respect to FIGS. 48A-48C). For example, a wire can additionally or alternatively run within or outside adjustment member 331. Pulling on the wire can cause the flexible member to bend.

Thus, using just flexible member 331 and adjustment tube 323 allows for adjustment of four degrees of freedom, the rotational angle, height, tilt, and degree of tilt.

Referring again to FIGS. 19A-C, specifically at tilt adjustment member control section 1912, knob 328 controls the tilt adjustment member 323. In some embodiments, turning the knob 328 clockwise causes the member 323 to retract, and turning the knob 328 counter-clockwise causes the member to advance. The knob 337 situated on path 329 (e.g., screw 329) controls rotational placement of the adjustment member 323. The knob 337 comprises a collet on its end that locks down on the adjustment member 323 allowing rotation of the knob 337 to result in rotation of adjustment member 323. The delivery system can comprise a hemostasis valve 1916 at an end of the tilt adjustment member 323 that allows for injection of saline to flush out crevices between tilt adjustment member 323 and adjustment member 331.

Now referring to the adjustment member 331 control section 1914, knob 328 controls the axial translation of the adjustment member 331. In some embodiments, turning the knob 328 clockwise causes the member 331 to retract, and turning the knob 328 counterclockwise causes the member to advance. The knob 337 situated on path 329 (e.g., screw 329) controls rotational placement of the adjustment member 331. The knob 337 comprises a collet on is end that locks down on the adjustment member 331 allowing rotation of the knob 337 to result in rotation of the adjustment member 331. The delivery system can comprise a hemostasis valve 1918 at an end of the adjustment member 331 that allows for flushing of the volume inside the adjustment member 323.

Figure 23A:
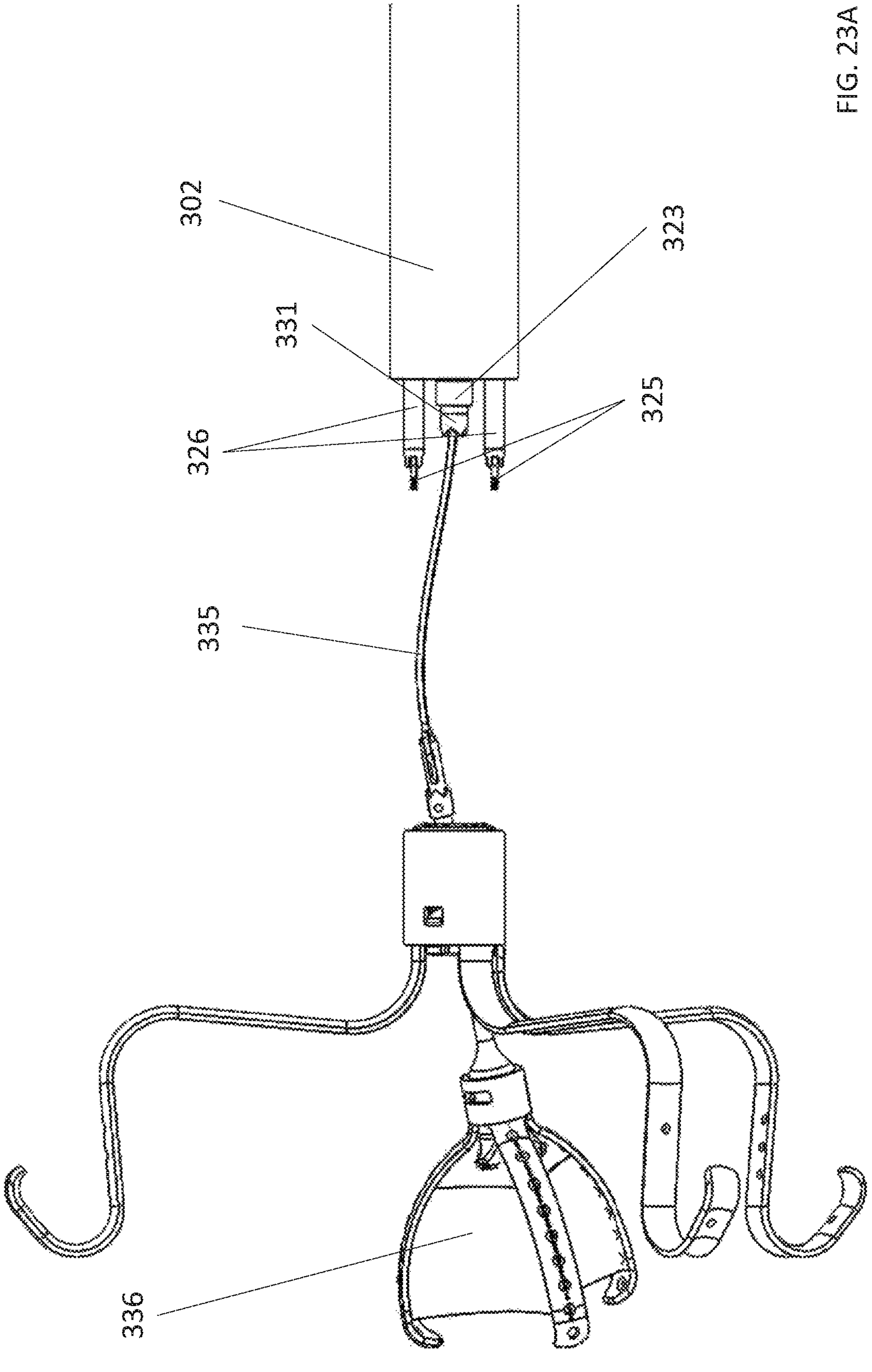
FIG. 23A shows top view of the device of FIGS. 18A and 18B with the screw guidewires and torqueing tubes retracted.
Figure 23B:
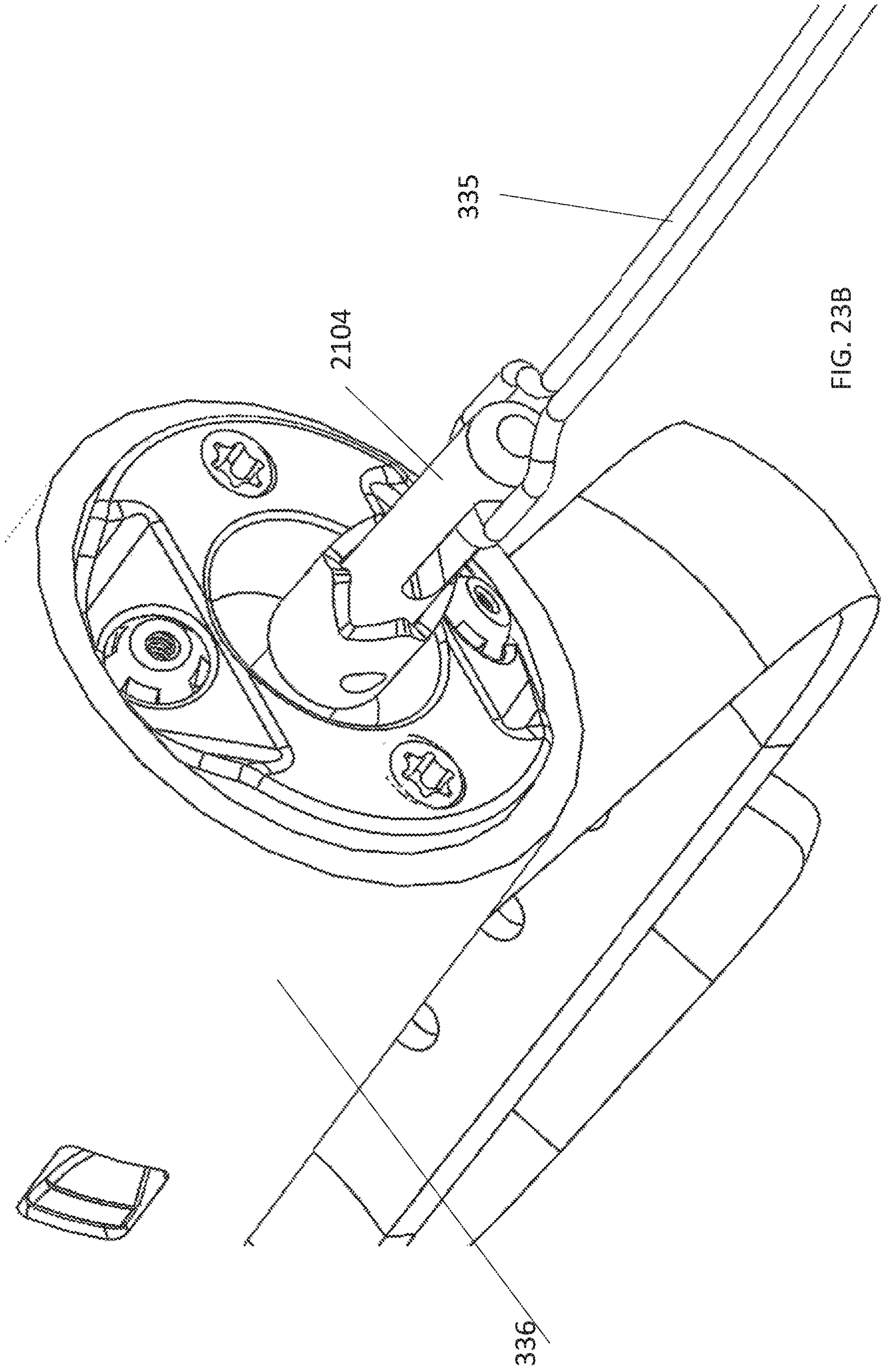
FIG. 23B shows a detailed view of a shaft and attached wire of the device of FIGS. 18A and 18B.

Once the clinician is satisfied with the positioning and orientation of the flow optimizer, it can be locked with respect to the anchoring assembly. In some embodiments, a ball joint is used to lock the flow optimizer into place (e.g., as described above with respect to device 700). Referring to FIG. 22A, a detailed perspective view of a proximal end of the anchoring assembly 2002 and device shaft 2104 is shown. Two (or more) screws 2012, similar to screws 777, 779 described with respect to device 700, are screwed into a ball (not shown) within the ball joint. Advancing the screws 2102 compresses the ball around the shaft 2104 preventing movement of the shaft relative to the anchoring assembly. FIG. 22B shows a detailed perspective view of the proximal end of the anchoring assembly 2002 including the screws 2102 when the adjustment member 331 is bent. As shown in FIGS. 22A and 22B, guidewires 325 extend from the screws 2102 to the catheter 302. Referring now to FIG. 22C, screw torqueing members 326 can extend from the multi-lumen shaft 344 over the guidewires 325. When the clinician is ready to lock the flow optimizer, the screw torqueing members 326 can be advanced along the guidewires as shown in FIG. 22D. FIG. 22E shows how a distal end of the screw torqueing members 326 mate with the head of the screws 2102 in such a way as to allow the torqueing members 326 to exert a rotational force upon the screws 2102. The guidewires 325 are attached to the screws 2102 using screws as well. Once the screws 2102 have been tightened to lock the flow optimizer in place, the screw torqueing members may be retracted and the guidewires 325 unscrewed and retracted, as shown in and described with respect to FIG. 23A.

Figure 40:
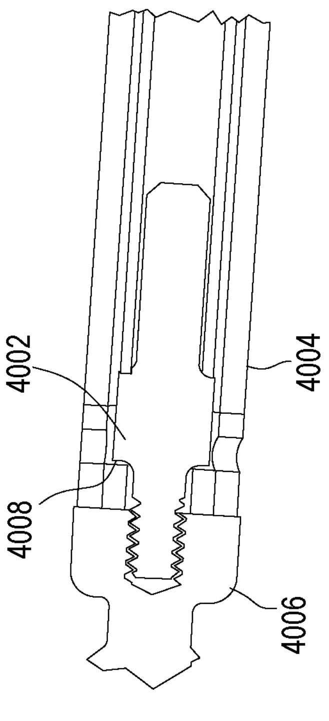
FIG. 40 shows a cutaway view of an embodiment of a screw torqueing member.

In some embodiments, the screw torqueing member comprises additional features configured to keep the screw torqueing member from separating from the screws. Referring to FIG. 40, an inner screw 4002 can be used to screw the screw torqueing member 4004 to the screw 4006. The smaller inner screw 4002 can be tightened down against inner shoulder 4008 on the screw torqueing member 4004 such that the screw torqueing member 4004 and screw 4002 will no longer be separable during the procedure. When the screw tightness is confirmed and the clinician is ready to release, the inner screw can be unscrewed (e.g., by rotating the guidewire screw hypotubes in the handle), detaching screw torqueing member. This feature advantageously allows a lot more confidence that the screw torqueing member is engaged with the screw.

Figure 41B:
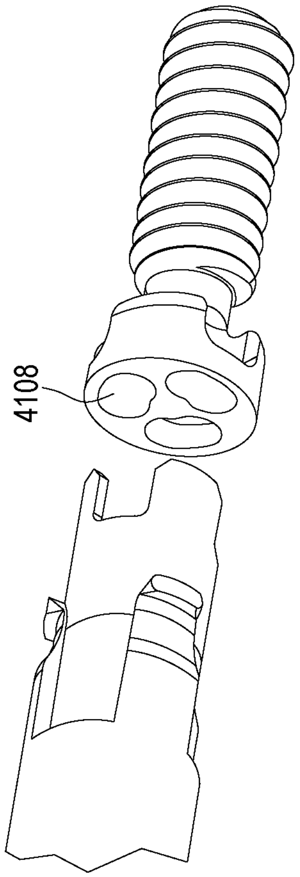
FIGS. 41A-41C show embodiments of interaction between a screw torqueing member and a screw.
Figure 41A:
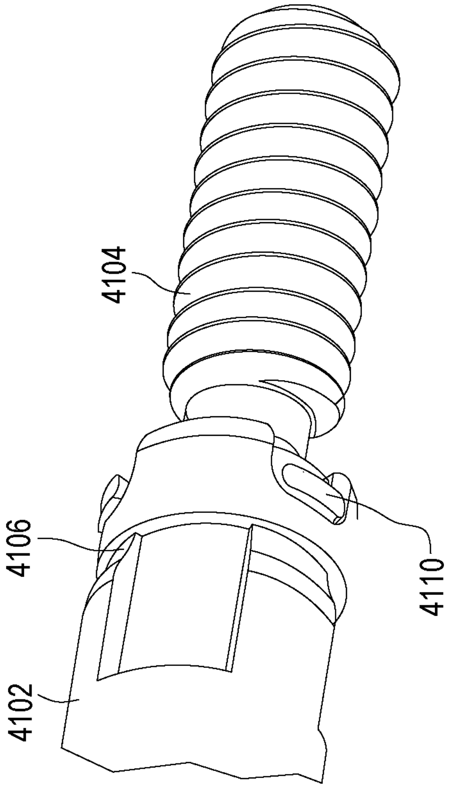
Figure 41C:
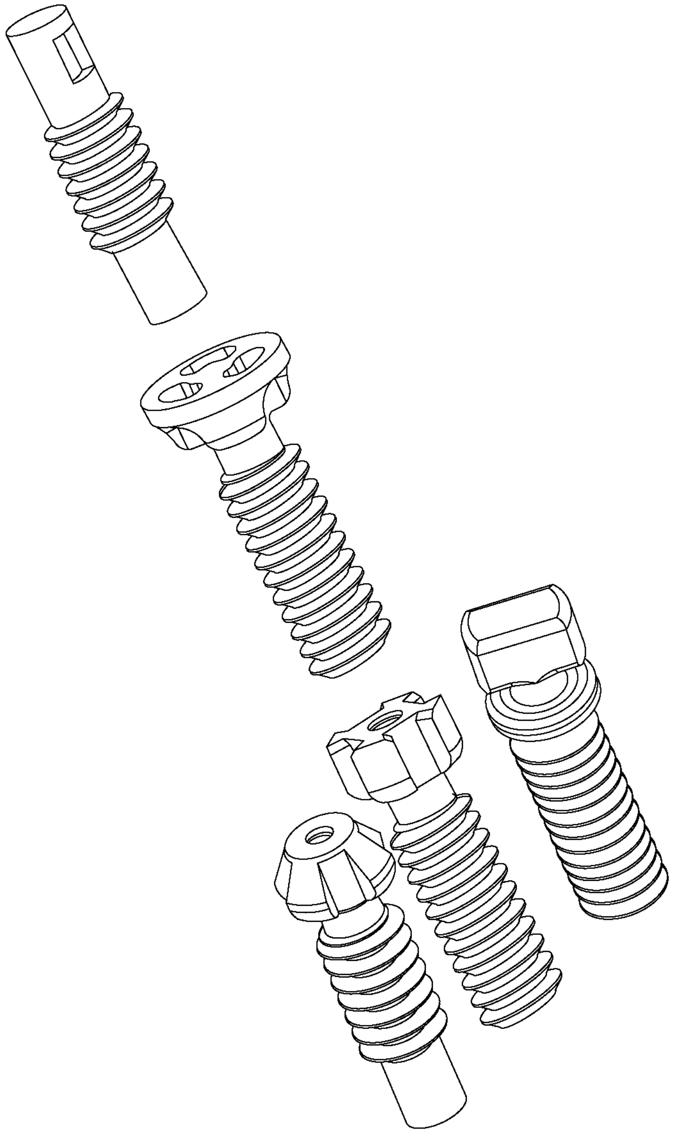

Referring to FIGS. 41A-41C, in some embodiments, an interference fit is used to lock the screw torqueing member 4102 to the screw 4104. As shown in FIG. 41A, the screw torqueing member 4102 may comprise features 4106 (e.g., projections, apertures, etc.). configured to mate with features 4108 (e.g., apertures, projections, etc.) on the screw 4104. The screw torqueing member may comprise features 4110 (e.g., tabs, hooks, etc.) that can engage the screw 4104 when an interference member (e.g., sleeve, outer hyptoube, etc.) is positioned between the engaged screw torqueing member and the screw. As long as the outer member is positioned between the engaged screw torqueing member and the screw, the locking features 4110 are engaged with the screw 4104 and two torqueing member 4102 and the screw 4104 are locked together. To disengage the screw torqueing member from the screw, the outer member can be withdrawn (e.g., retracted) and the two components can be disengaged, as shown in FIG. 41B.

FIG. 41C show various embodiments of screws that can be used to connect to the screw torqueing member using an interference fit lock, as described with respect to FIGS. 41A and 41B.

Control of guidewires 326 and torqueing tubes 325 is done manually from outside of the handle. A clinician can grip hemostasis valves 1920, best shown in FIG. 19B, attached to a proximal end of the torqueing tubes 326 and advance or retract the tubes 326. The guidewires are also manually controlled at their proximal end. The guidewires 326 can be unscrewed from the screw 2102.

Figure 42A:
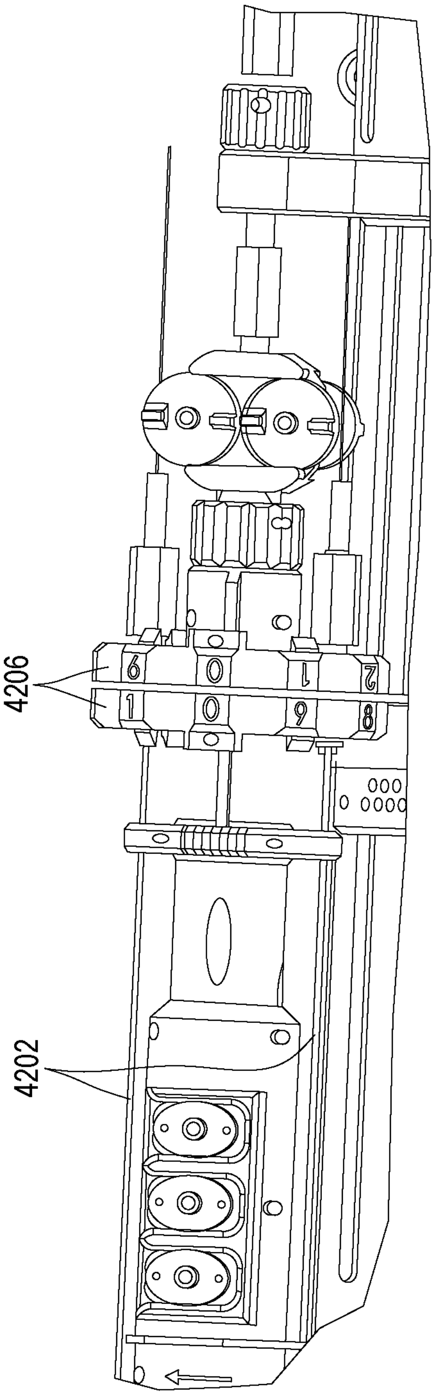
FIGS. 42A-42C show various views of an embodiment of a torqueing control section.
Figure 42B:
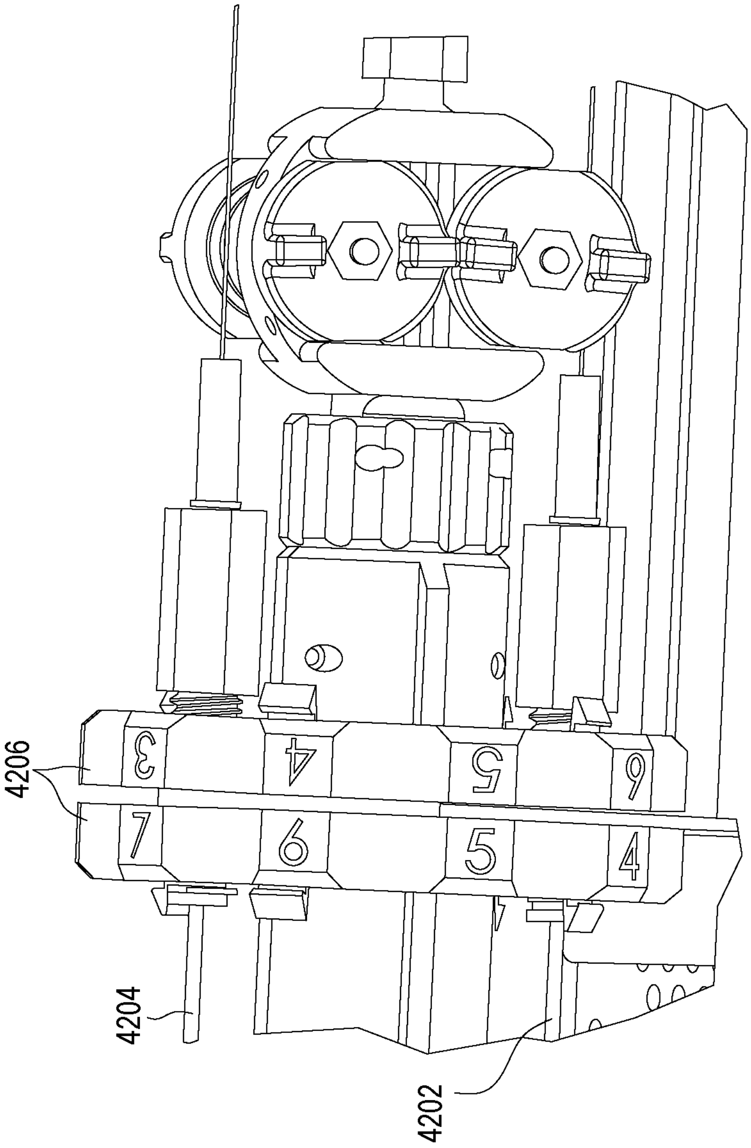

In some embodiments, the torqueing tubes can comprise one or more rigid tubes at their proximal ends. As shown in FIG. 42A, a rigid tube 4202 can be positioned at the proximal end of the torqueing tube. The rigid tube 4202 can be fixed to the torqueing tube so that torque is translated easily between the two. The rigid tube 4202 can be fixed to a control knob 4206.

Figure 42C:
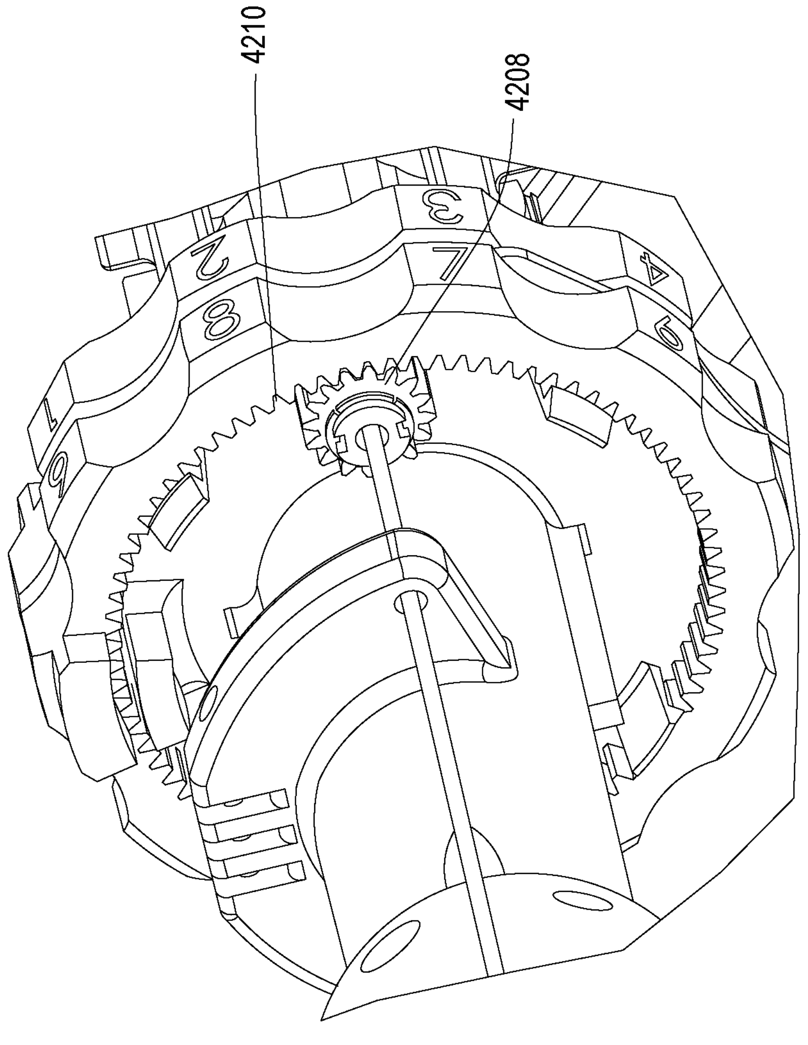
Figure 43:
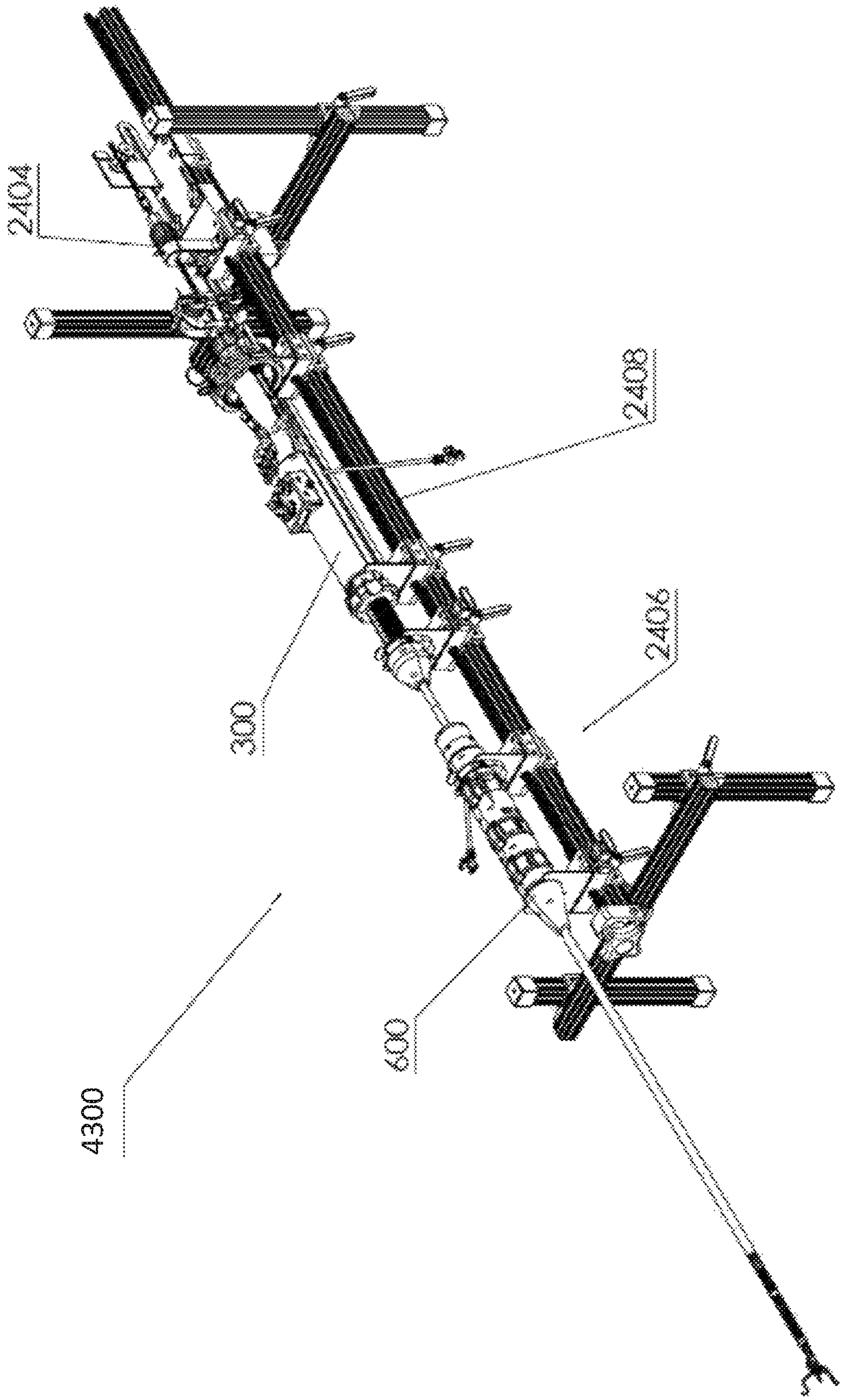
FIG. 43 shows a perspective view of an embodiment of a delivery system and platform for a valve support device.

In some embodiments, gears may be positioned between the tube and the knob. As shown in FIG. 42C, a smaller tube gear 4208 can be configured to engage with a larger knob gear 4210 on the knob 4206. There can be a knob for each of the torqueing tubes. In some embodiments, the knobs can be positioned to be adjacent, with one more proximal to the other. In some embodiments, the knobs are configured to be turned in one direction (e.g., to tighten the screws). Turning the knob in the opposite the direction can be more difficult, requiring The multi-lumen shaft 344 terminates in the handle, where the various tubes and devices contained in the lumens separate, as best shown in FIG. 19C. The screw torqueing tube 326 and guidewire 325 exit the multi-lumen shaft 344 there and enter block 310, which has three separate lumens 1922 for separating the various hypotubes. More or fewer lumens are also contemplated. The block 310 comprises an injection port and a series of seals 1925 (shown in detailed view of FIG. 19D) including a seal overlapping the adjustment member 323, seals overlapping the torqueing tubes 326 and seal 321, which can be an O-Ring seal. The crevices within the catheter, between the various tubes, wires, and other devices need to be flushed with saline to prevent air from getting expelled from the catheter and to prevent blood from collecting and coagulating within the catheter and getting expelled. Saline can be injected through injection port 1924 (FIG. 19A) and can flush the crevices inside the multi-lumen shaft and the outside of the tubes.

Once the clinician has retracted the guidewires 325 and the torqueing tubes 326, the wire 335 attached to the shaft 2104 is removed. Referring to FIG. 19B, the wire 335 extends back proximally through the handle and loops around spool 1930 positioned at a proximal end of the handle. The spool 1930 can be used to adjust tension in the wire 335. When pushing the device out of the catheter 302, the force with which the arms 1804 push against the end of the catheter can be counteracted to prevent the arms from springing outwards. The wire 335 can be kept in fairly high tension to keep the proximal end of the implant butted securely against the multi-lumen shaft. Once the device is deployed and during adjustment of its position, the tension of the wire can be adjusted so that the shaft 2104 is butted up against the adjustment member 331. To release the wire 335 at the end of the procedure, a clinician unwinds it from the spool 1930 and pulls one end until the wire 335 is completely removed from the patient.

Figure 24A:
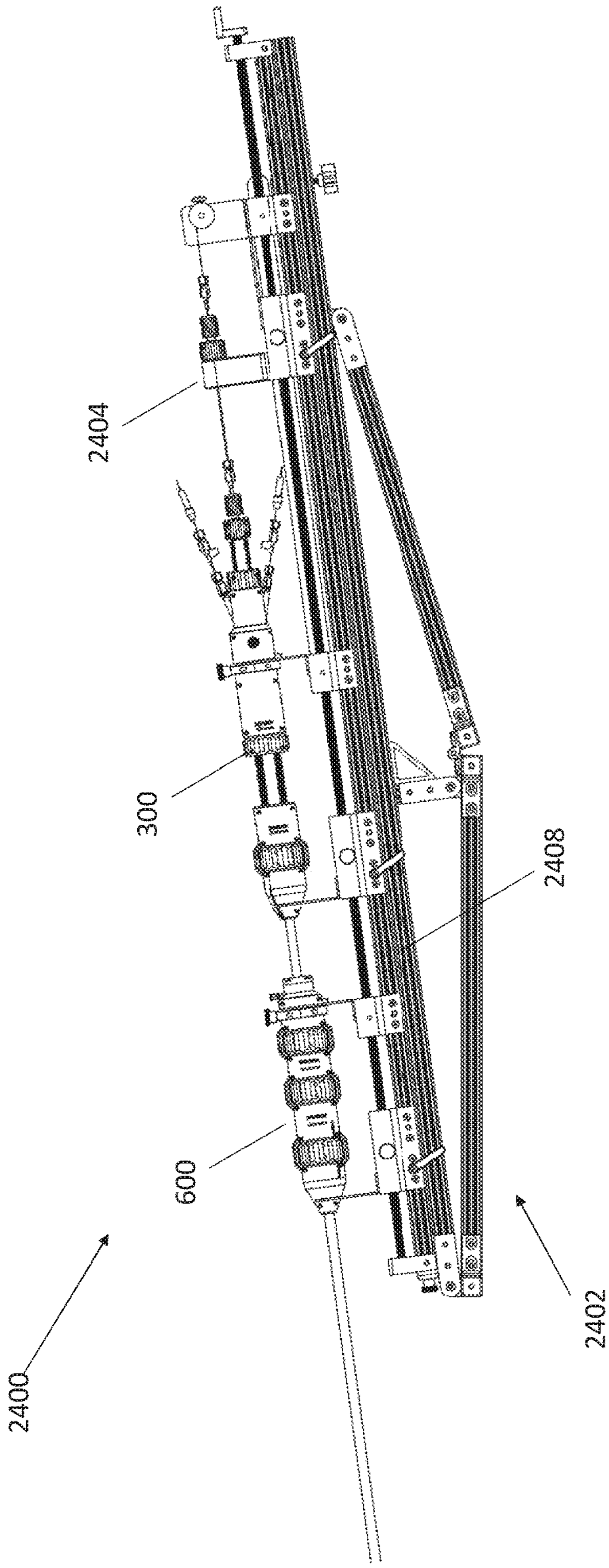
FIG. 24A shows a side view of another embodiment of a delivery system and platform.
Figure 24B:
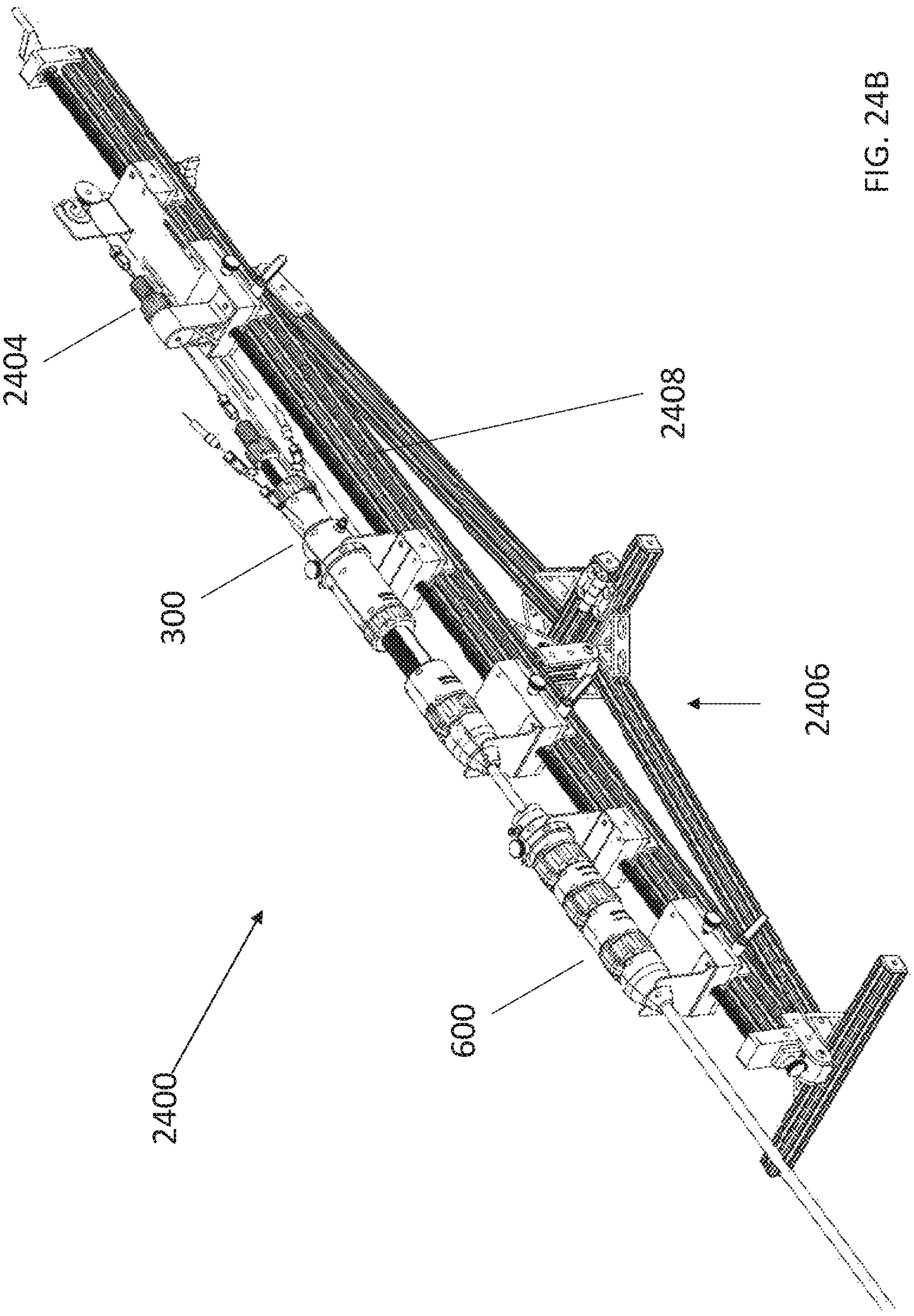
FIG. 24B shows a perspective view of the delivery system and platform of FIG. 24A.

Referring to FIGS. 24A and 24B, additional embodiments of a delivery system 2400 for delivering and positioning the heart valve support devices described herein are provided. The embodiment shown herein comprises a sheath through which the catheter extends. In some embodiments, the sheath, instead of the catheter, can perform most of all of the bending and deflecting functionality. Offloading this functionality onto the sheath can allow for the catheter to rotate within the sheath without affecting the deflection angles of the sheath.

FIGS. 24A and 24B show a side view and an isometric view, respectively, of an embodiment of a delivery system 2400 and a platform 2402. Unless otherwise described, the delivery system 2400 can comprise similar structure and functionality as delivery system 1900. The delivery system 1900 can comprise a sheath control section 600, a catheter and tilt adjustment member control section 300 and an adjustment member control section 2404. The platform 2406 can comprise a rail 2408 along which the various control section may be translated.

Figure 25A:
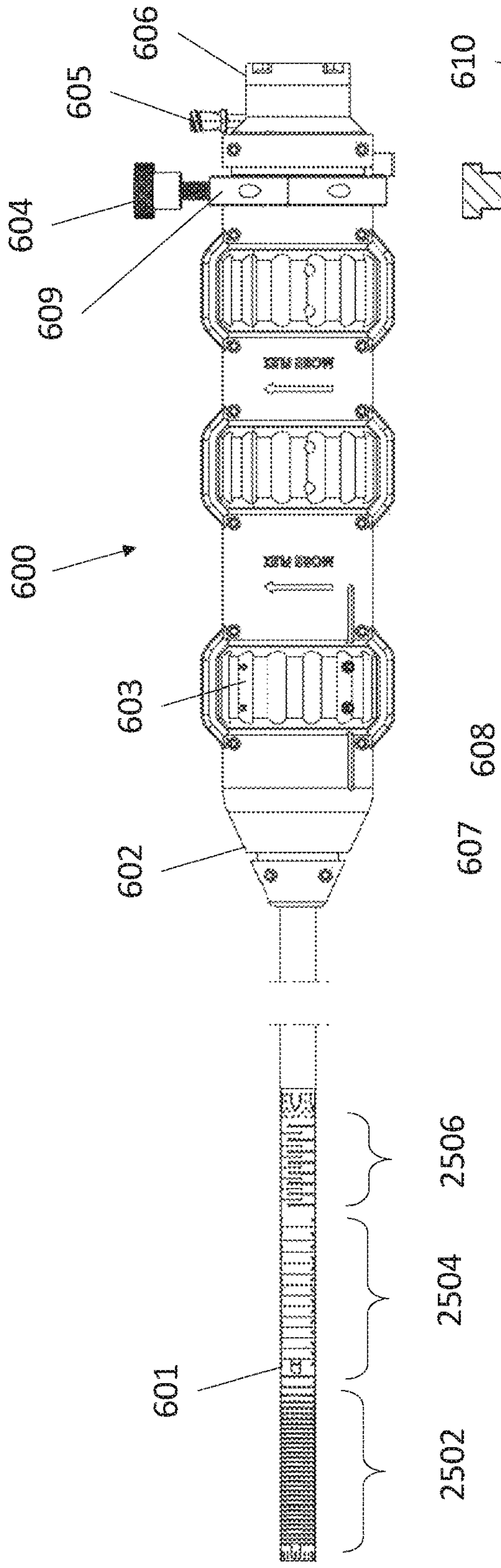
FIG. 25A shows a side view of an embodiment of a sheath control section of the delivery system of FIGS. 24A and 24B.
Figure 25B:
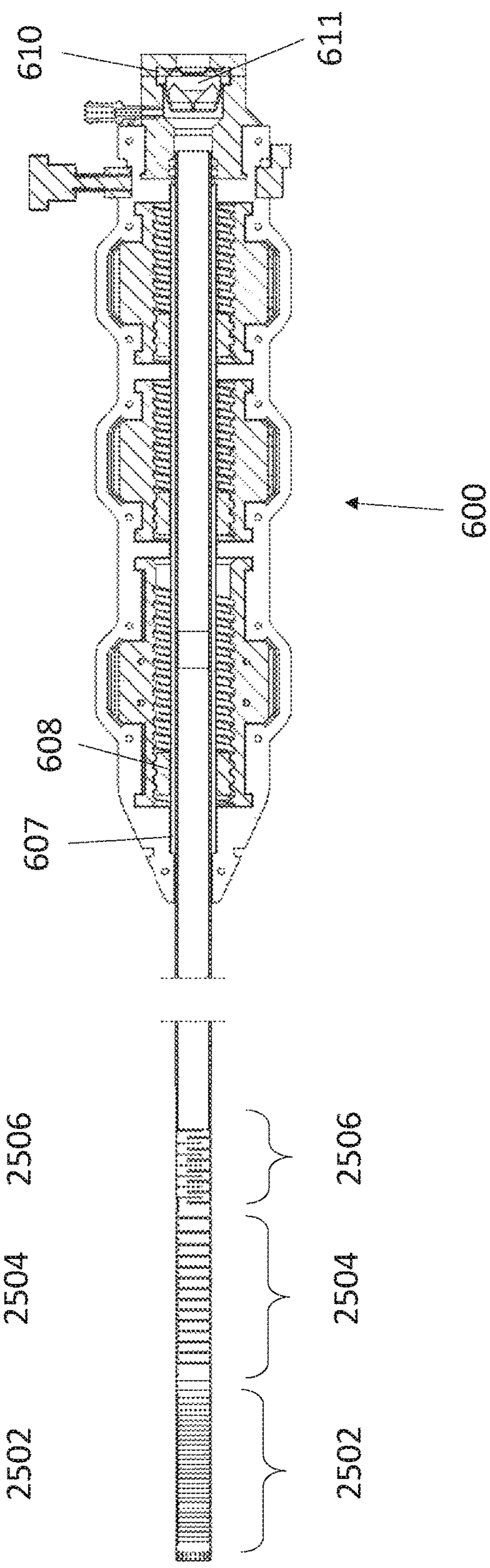
FIG. 25B shows a side cutaway view of the sheath control section of FIG. 25A.
Figures 26A, 26B:
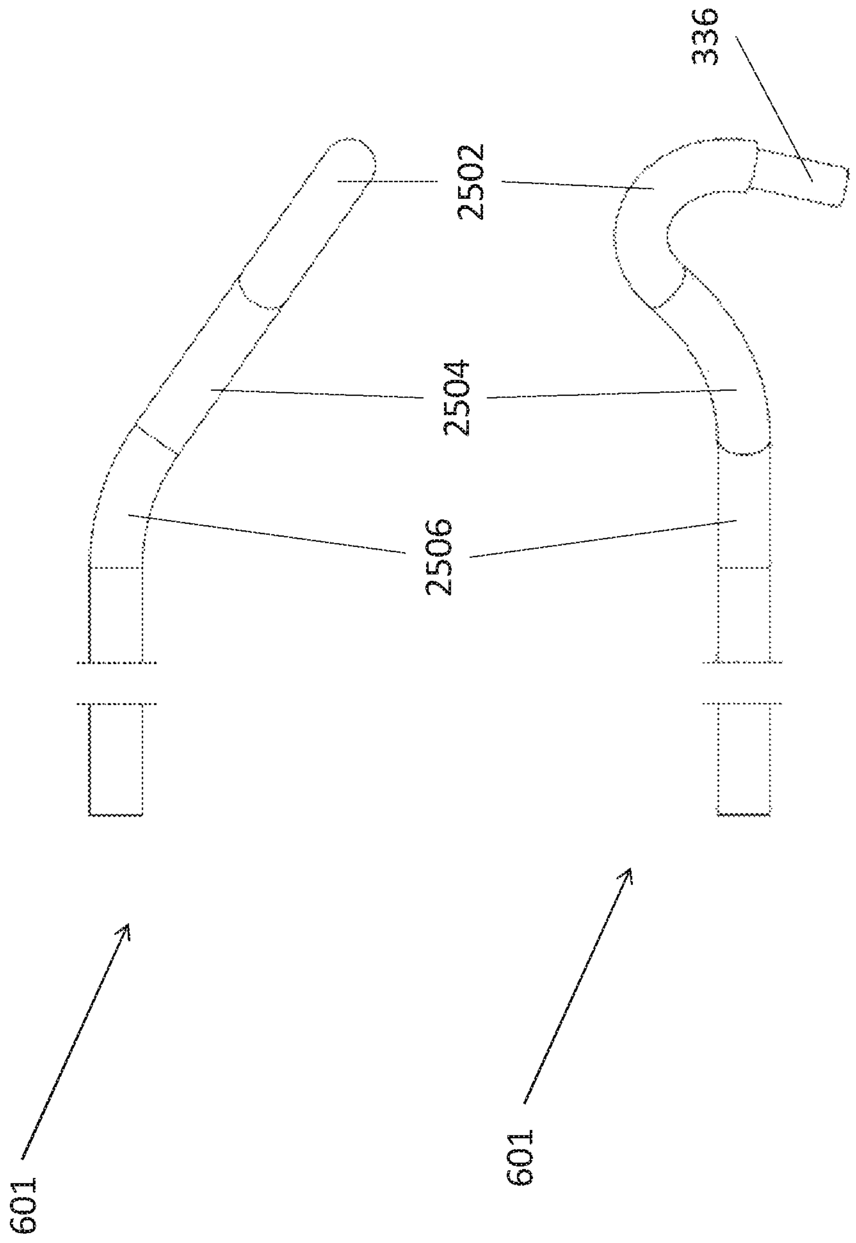
FIGS. 26A and 26B show bending planes of a distal end of the sheath, in some embodiments.

Referring now to FIGS. 25A and 25B, a side view and side cutaway view, respectively, of the sheath control section 600 and a distal end of the sheath 601 are shown. The sheath control section 600 comprises a rotation locking collar 609 configured be positioned within a groove around the control section 600. The collar 609 can rotate with respect to the handle, but cannot rotate with respect to the corresponding slot on the platform. Rotation control knob 604 can be used to lock collar 609 in rotational position with respect to sheath control section 600. For example, knob 604 can be used to tighten the collar 604 against the sheath control section 600. Injection port 605 can be used to flush out the space between the sheath 601 and the catheter. The distal end of the sheath can comprise one or more bending portions configured to effectuate a desired bending radius and/or bend length. The different bending capabilities can be effected by, for example, number of slots/openings/scores, frequency of slots/opening scores, position of slots/opening/scores, etc. For example, as shown in FIGS. 25A and 25B, the distal end of the sheath comprises a first bending portion 2502, a second bending portion 2504, and a third bending portion 2506. These bending sections can allow for the bending or deflection required to advance the sheath to the right atrium. Two positions involved in navigating the sheath 601 to the right atrium are shown in FIGS. 26A and 26B. First bending portions 2502, second bending portions, and third bending portion can allow the sheath 601 to assume the configurations shown in FIGS. 26A and 26B.

Figures 27A, 27B:
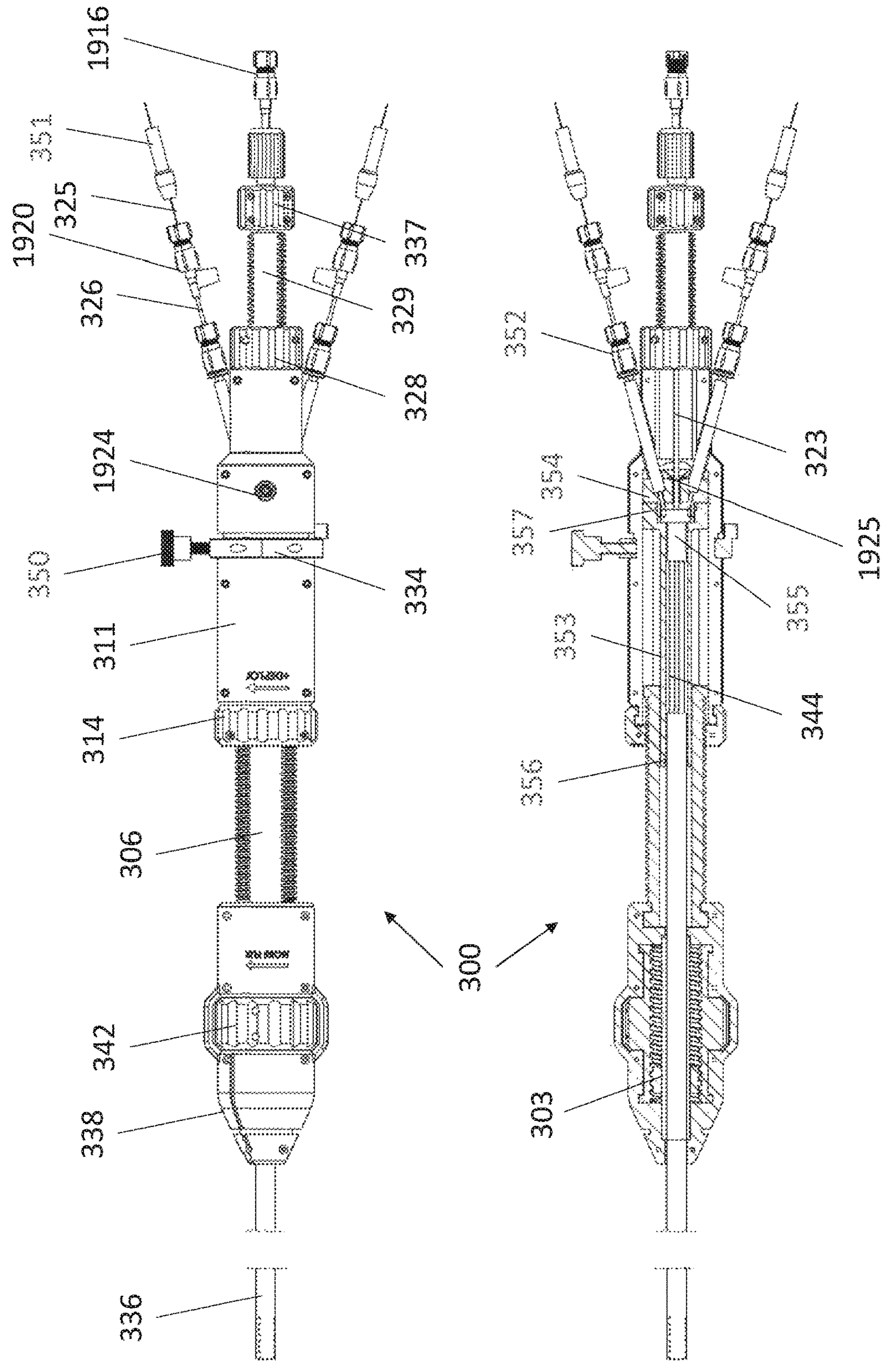
FIG. 27A shows a side view of an embodiment of a catheter and tilt adjustment member control section of the delivery system of FIGS. 24A and 24B.
FIG. 27B shows a side cutaway view of the catheter and tilt adjustment member control section of FIG. 27A.

Referring now to FIGS. 27A and 27B, a side view and side cutaway view of the catheter and tilt adjustment member control section 300 are shown.

Knob 342 of the handle can be used to deflect the catheter 1802 as it navigates the vasculature. In some embodiments. deflection of the catheter can be used to allow fine adjustments of the of the implant after the catheter exits the sheath and is positioned coaxially with the native valve annulus. In some embodiments, threads inside each knob can mate with exterior threads on an interior deflector element. The deflector element is configured to move forward and backward along a rail 303. The rail keeps the deflector from rotating when turning the knob and limits the deflector elements movement to forward or backward along the rail. The deflector elements are attached to pull wires that run through the catheter 302 and can be used to bend the catheter by pulling or pushing the pull wires.

Multi-lumen shaft 344 is positioned within the catheter. Turning knob 314 on the handle can cause the catheter 302 to be pulled backward relative to shaft 344 to unsheathe the implant 1800.

The knob 314 can control an unsheathing screw 306 which can be used to pull the proximal end of the handle distally. When the unsheathing screw 306 is in its distal most position, as in FIGS. 27A and 27B, the catheter is fully retracted. The multi-lumen shaft of the catheter butts up against the implant and slowly pushes it out of the catheter. A rod 353 can help to stabilize the unsheathing screw 306 as it moves back and forth. The rod can comprise a seal 356 (e.g., O-ring) to allow sealing against the flow optimizer 336.

Figures 28A, 28B:
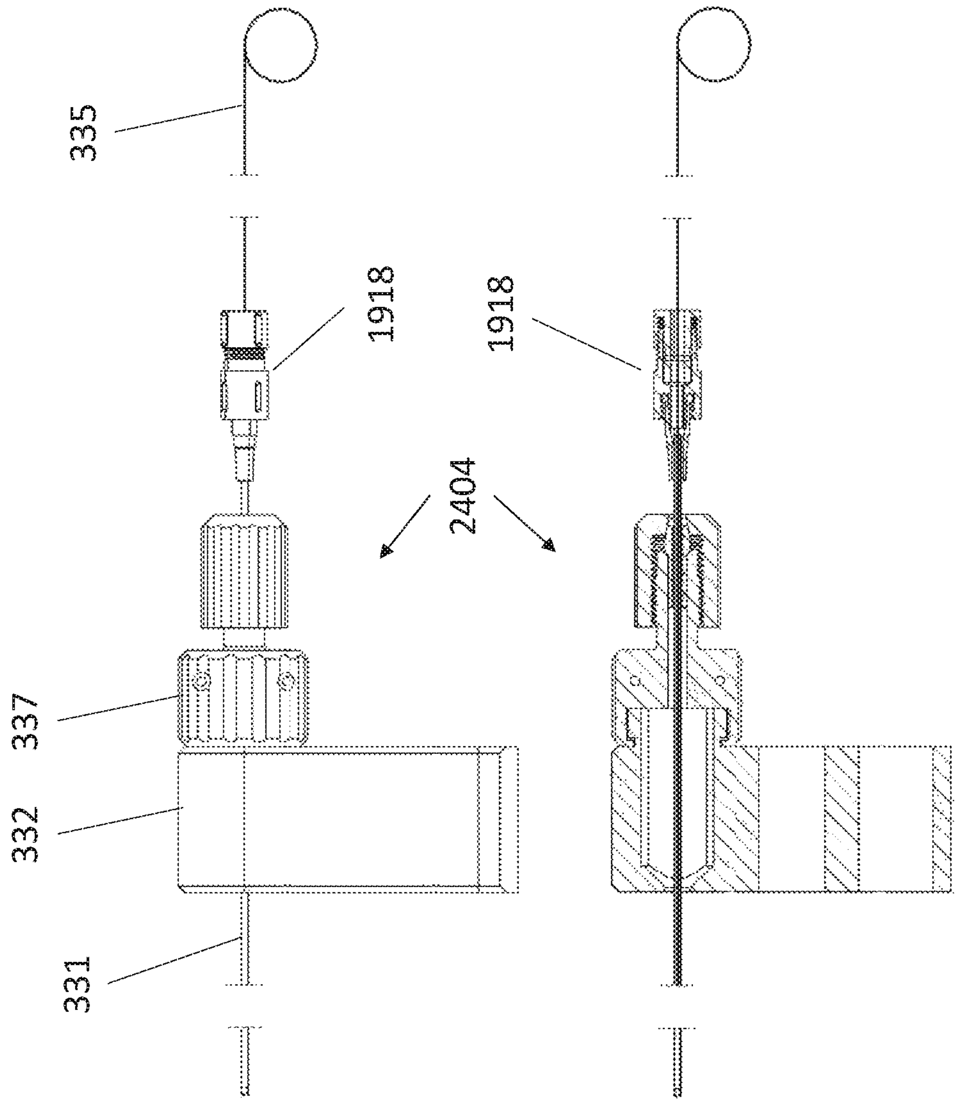
FIG. 28A shows a side view of an embodiment of an adjustment control section of the delivery system of FIGS. 24A and 24B.
FIG. 28B shows a side cutaway view of the adjustment control section of the delivery system of FIG. 28A.

A tilt adjustment member 323 (e.g., tube) overlaps and is concentric with an adjustment member 331 (FIGS. 28A and 28B). The tube 323 has a bend towards its distal end. When the tilt adjustment member 323 is fully retracted and contained within the catheter 302, it is generally straight. When it is exposed, the tilt adjustment member 323 biases towards its bent shape (e.g., like shown in FIG. 21). The tilt adjustment member 323 bending causes adjustment member 331 to bend, tilting the flow optimizer with respect to the anchoring assembly. Rotating the bent adjustment member 331 can adjust the orientation of the flow optimizer tilt. In other words, rotating the bent flexible member can adjust the portion of the anchoring assembly towards which the flow optimizer tilts. Adjusting the length of the exposed portion of tilt adjustment member 323 can adjust the degree of bend in the flexible member 331. Adjusting the degree of bend in the flexible member can adjust the degree of tilt of the flow optimizer. It will be appreciated that other mechanisms for bending flexible member 331 to control the tilt of the flow optimizer are also contemplated. For example, a wire can additionally or alternatively run within or outside adjustment member 331. Pulling on the wire can cause the flexible member to bend.

Knob 328 controls the tilt adjustment member 323. In some embodiments, turning the knob 328 clockwise causes the member 323 to retract, and turning the knob 328 counter-clockwise causes the member to advance. The knob 337 situated on path 329 (e.g., screw 329) controls rotational placement of the adjustment member 323. The knob 337 comprises a collet on its end that locks down on the adjustment member 323 allowing rotation of the knob 337 to result in rotation of adjustment member 323. The delivery system can comprise a hemostasis valve 1916 at an end of the tilt adjustment member 323 that allows for injection of saline to flush out crevices between tilt adjustment member 323 and adjustment member 331.

As described with respect to FIGS. 19A and 19B, control of guidewires 325 and torqueing tubes 326 is done manually from outside of the handle. For example, a clinician can grip hemostasis valves 1920 attached to a proximal end of the torqueing tubes 326 and advance or retract the tubes 326. The guidewires are also manually controlled at their proximal end. Torqueing member (e.g., chuck) can be tightened onto the guide wires 325 and can be used to provide a user more surface area to grab onto to manipulate the guide wires.

As described with respect to the delivery system 1900, the multi-lumen shaft 344 terminates in the handle, where the various tubes and devices contained in the lumens separate. The screw torqueing tube 326 and guidewire 325 exit the multi-lumen shaft 344 there and enter flushing block 354. Flushing block 354 can comprise an injection port 1924. Saline can be injected through the injection port 1924 for flushing of the catheter. Flushing block comprises three separate lumens for separating the various hypotubes. More or fewer lumens are also contemplated.

The block 354 comprises a series of seals 1925, 356 (e.g., O-ring), 357 (e.g., O-ring), 352 (e.g., hemostasis valve). These seals include a seal overlapping the adjustment member 323, seals overlapping the torqueing tubes 326 and seal 321, which can be an O-Ring seal. The crevices within the catheter, between the various tubes, wires, and other devices need to be flushed with saline to prevent air from getting expelled from the catheter and to prevent blood from collecting and coagulating within the catheter and getting expelled. Saline can be injected through injection port 1924 and can flush the crevices inside the multi-lumen shaft and the outside of the tubes.

The delivery system can comprise a multi-lumen shaft attachment 355. The attachment 355 can be fixed (e.g., glued) onto a proximal end of multi-lumen shaft 344 to fix the multi-lumen shaft 344 with respect to the handle. The attachment 355 can also help to more easily guide the screw torqueing tubes 326 into the lumen of the multi-lumen shaft.

Cutouts on standoffs on the platforms (e.g., on platform 2903, 2904, FIG. 29A) can be configured to mate with rotation collar 334. This interaction allows the handle to rotate within the cutouts but not translate forward or backward. Rotation locking knob 350 positioned on the collar 334 can be tightened to lock the catheter and tilt adjustment control section with respect to the sliding stage or loosened to allow rotation between the catheter and tilt adjustment control section.

Moving to FIGS. 28A and 28B, side view and side cutaway views, respectively of an adjustment member control section 2404 are shown. The knob 337 comprises a collet on its end that locks down on the adjustment member 331 allowing rotation of the knob 337 to result in rotation of the adjustment member 331. The delivery system can comprise a hemostasis valve 1918 at an end of the adjustment member 331 that allows for flushing of the volume inside the adjustment member 331. Unlike the adjustment member control section 1914, the translation of the adjustment member control section 2404 is controlled by the lead screw, described in more detail with respect to FIGS. 29A and 29B.

The delivery system 2400 has been shown with having a control section for the catheter and tilt adjustment member and a separate control section for the adjustment member; however, in some embodiments, the controls for the adjustment member are incorporated into the control section for the catheter and the tilt adjustment member. Other combinations of control are also contemplated.

Figure 29A:
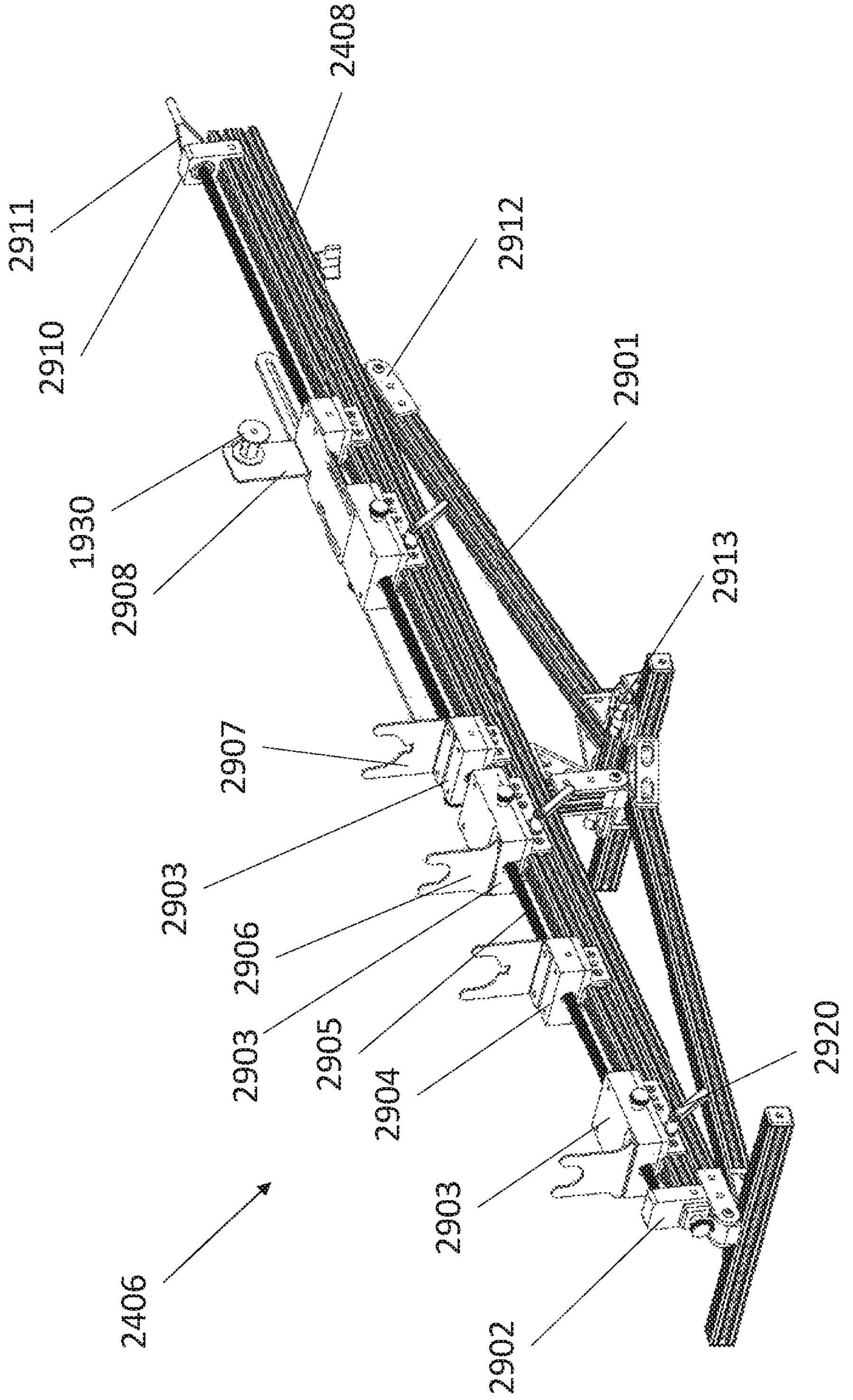
FIG. 29A shows an isometric view of the platform of FIGS. 24A and 24B.
Figure 29B:
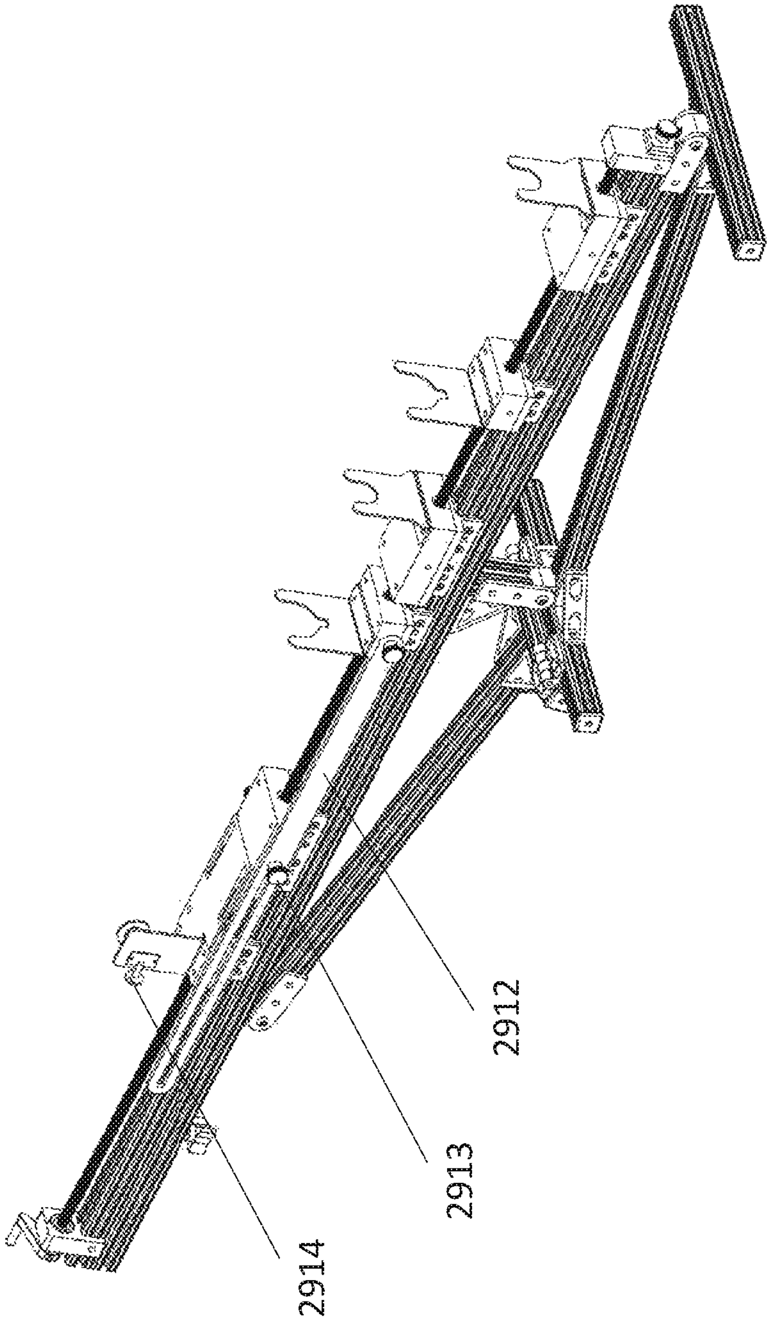
FIG. 29B shows a back isometric view of the platform of FIG. 29A.

FIGS. 29A and 29B show front and back isometric views, respectively of a platform for holding and manipulating the position of various components of the delivery system 2400. The platform comprises a rail 2408 along which various components may be translated. In some embodiments, the rail 2408 comprises a T-slot type rail (e.g., T-slot aluminum extrusion). Positioned on the rail are a distal lead screw block 2902 and a proximal lead screw block 2910. The lead screw blocks 2902 can be configured to support the lead screw at or near each end of the lead screw. Positioned on the proximal lead screw block 2910 can be a lead screw crank 2911 configured to allow translation manipulation of the lead screw. Other control mechanisms are also contemplated (e.g., knob). Shown in FIG. 28A are two types of platforms for riding along the rail and holding various components of the delivery system. Control platform 2903 comprises a mechanism configured to engage or disengage from the lead screw. The mechanism can comprise a threaded portion configured to engage with the threads of the lead screw (e.g., a portion of a nut). The control platform may also comprise a locking mechanism configured to lock or unlock the platform 2903 to the rail 2408. Crank 2920 can be used to control the locking mechanism. A support platform 2904 can be configured to lock and unlock from the rail 2408 (e.g., as shown with respect to platform 2903).

A control platform can comprise a standoff 2906 comprising a circular cutout shaped to mate with a reciprocal cutout on the delivery system (e.g., on collar 334). The support platform can also comprise a standoff 2907 comprising a circular cutout shaped to mate with a reciprocal cutout on the delivery system. The standoff 2907 may also comprise a cutout (e.g., square cutout) for preventing rotation relative to the collar 334. The collar can comprise a corresponding tab configured to (e.g., shaped to) mate with the cutout. Each component of the handle (e.g., sheath control section, catheter and tilt adjustment member control section, adjustment member control section) can be supported and controlled by a control type platform and a support type platform. It will be appreciated that the various components of each type of platforms may be combined and rearranged into different configurations achieving the same functionality.

Spool support 2908 is shown positioned on a proximal platform. Spool 1930 is positioned on the spool support. As shown in FIG. 29B, peg 2914 is operatively connected to the spool 1930. The peg 2914 is configured to turn the spool 1930. In some embodiments, the spool can use a worm gear so that it cannot be driven back. In other words, the spool will not spin under the force of the wire pulling on it.

As shown in FIG. 29B, connector 2912 extends between the shaft control section 2404 and the catheter and tilt adjustment member control section 300. This connector 2912 can be used to control the location of the two control sections with respect to one another. Knob 2913 can be used for fixing the location of one or both control sections.

The lead screw 2905 extends between distal screw block 2902 and proximal screw block 2910 and runs through the platforms positioned along the rail 2408. At least some of the various platforms through which the lead screw runs can be configured to engage or disengage from the lead screw, allowing their axial position to be manipulated by the lead screw. Axial adjustment using the lead screw can allow for precise manipulation of these components. Additionally, axial translation and control using a lead screw allows a single operator to control the position of multiple components simultaneously.

In some embodiments, a user may unlock one or more of the platforms from the rail in order to advance a component of the delivery system. For example, when advancing the sheath or the catheter from the insertion site to the heart, the corresponding components may be slid along the rail. Once the delivery tools are in the vicinity of the valve, the lead screw can be used for more precise translational positioning and/or adjustment.

The rail 2408 is at least partially supported by an angled rail 2901. A first hinge 2913 is connected to a first end of the angled rail 2901 where it meets the platform base. A second hinge 2912 is connected to a second end of the angled rail 2901 where it meets the rail 2408.

Figure 30A:
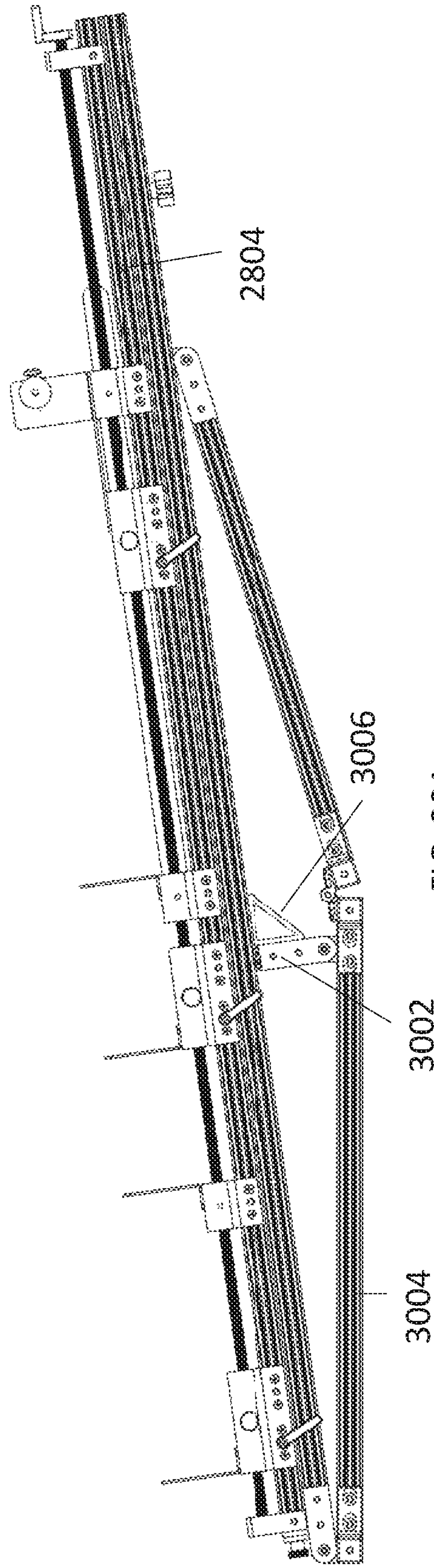
FIGS. 30A and 30B show side views of the platform of FIGS. 29A and 29B set at various angles.
Figure 30B:
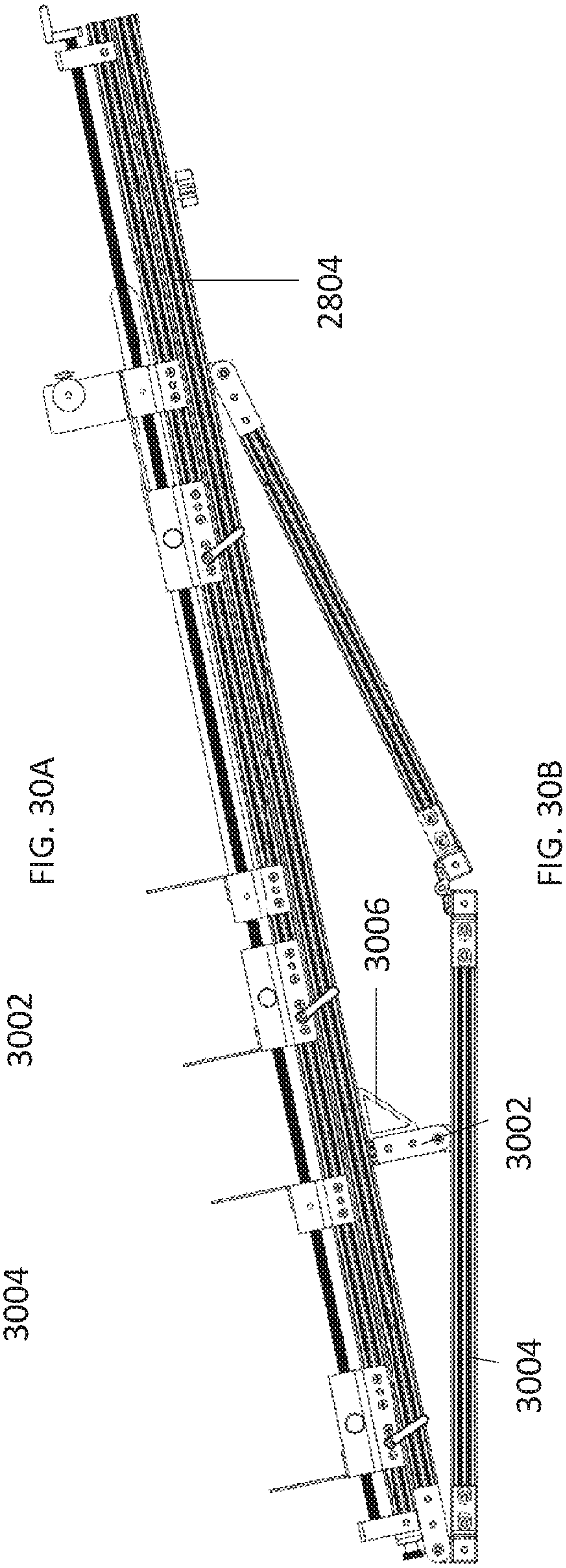

Referring now to FIGS. 30A and 30B, a connector 3002 supports the rail 2408 and connects it to the base rail 3004. Translating the connector 3002 can adjust the angle of the rail 2408 relative to the base rail 3004 (e.g., relative to horizontal). The connector 3002 is attached to or integral with support 3006. In some embodiments, support 3006 can be fixed (e.g., using screws) into inserts that can slide along the rail 2408. To adjust the position of the connector 3002, the insert can be released from its fixed position (e.g., by loosening screws on inserts) and the connector 3002 can be slid along rail 2408 and base rail 3004 to the desired position, as shown in FIG. 30B, in which the connector 3002 has been slid distally, relative to the position of FIG. 30A. The position of the connector 3002 in FIG. 30B creates a greater angle for the rail 2804 than that of FIG. 30A. Sliding the connector distally increases the angle, and sliding the connector proximally decreases the angle. Once in the desired position, the support 3006 can be fixed to the rail 2408. Other mechanisms for fixing the connector 3002 to the rail 2408 (e.g., spring-loaded connection, clamp, etc.) are also contemplated.

Adjusting the angle of the delivery system can be advantageous to achieve an optimal entry angle regardless of patient and operator size. For example, a patient may have a larger or smaller thigh relative to the average patient. Being able to adjust the angle of entry can make it easier to perform the procedure in such situations. Being able to adjust the entry angle can help to line everything up as close to straight as possible to make advancement of the delivery and treatment devices to the valve easier.

Figure 31B:
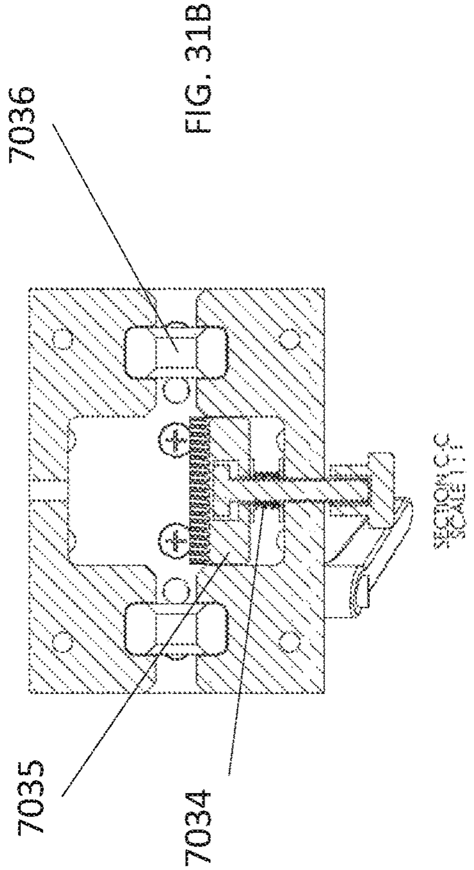
FIG. 31B shows a cutaway view of the sliding platform of FIG. 31A.
Figure 31C:
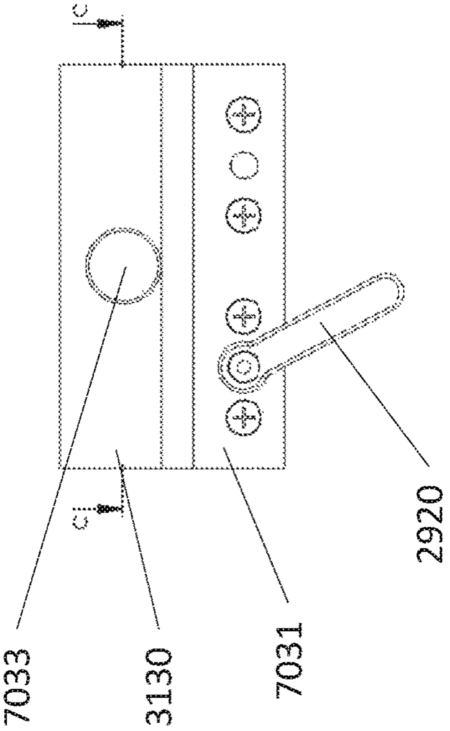
FIG. 31C shows a front view of the sliding platform of FIG. 31A.
Figure 31A:
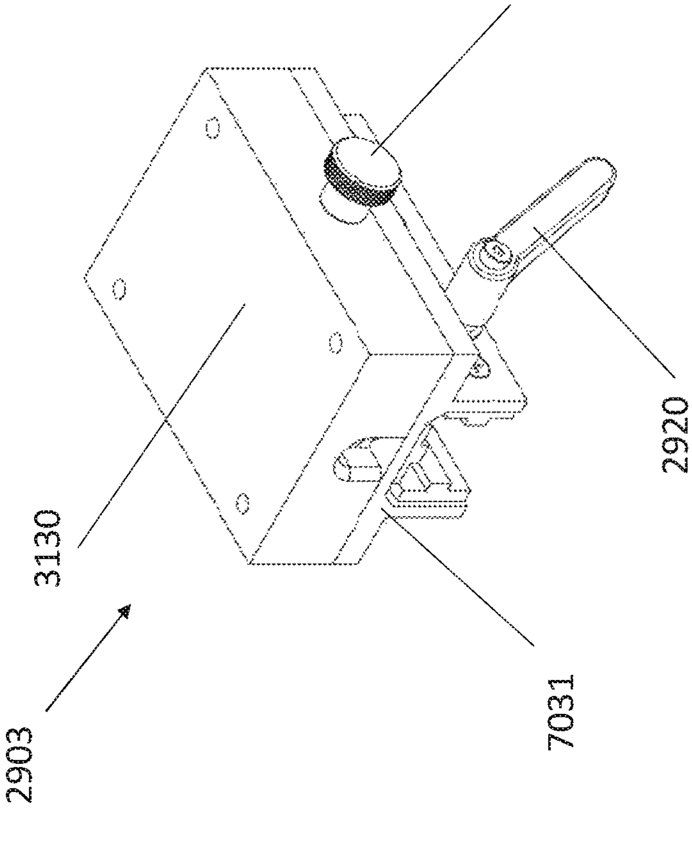
FIG. 31A shows an isometric view of a sliding platform on the platform of FIGS. 29A and 29B.

Referring now to the isometric view, section view, and side view, respectively, of FIGS. 31A-31C, a detailed view of platform type 3902 is shown. The platform comprises a mounting block 3130. The mounting block 3130 is positioned on a linear slider 3131 configured to slide along rail 2804. Crank 2920 is positioned on the slider and is configured to lock the slider 3131 to the rail, via a bolt which tightens 7031 to rail 2804. Knob 7033 can be used to engage or disengage the platform 2903 to the lead screw. As shown in the top section view of FIG. 31B, the platform comprises a lead screw connector 7035 resembling a half-nut. The knob 7033 can cause the connector 7035 to engage or disengage from the lead screw threads.

Figure 32:
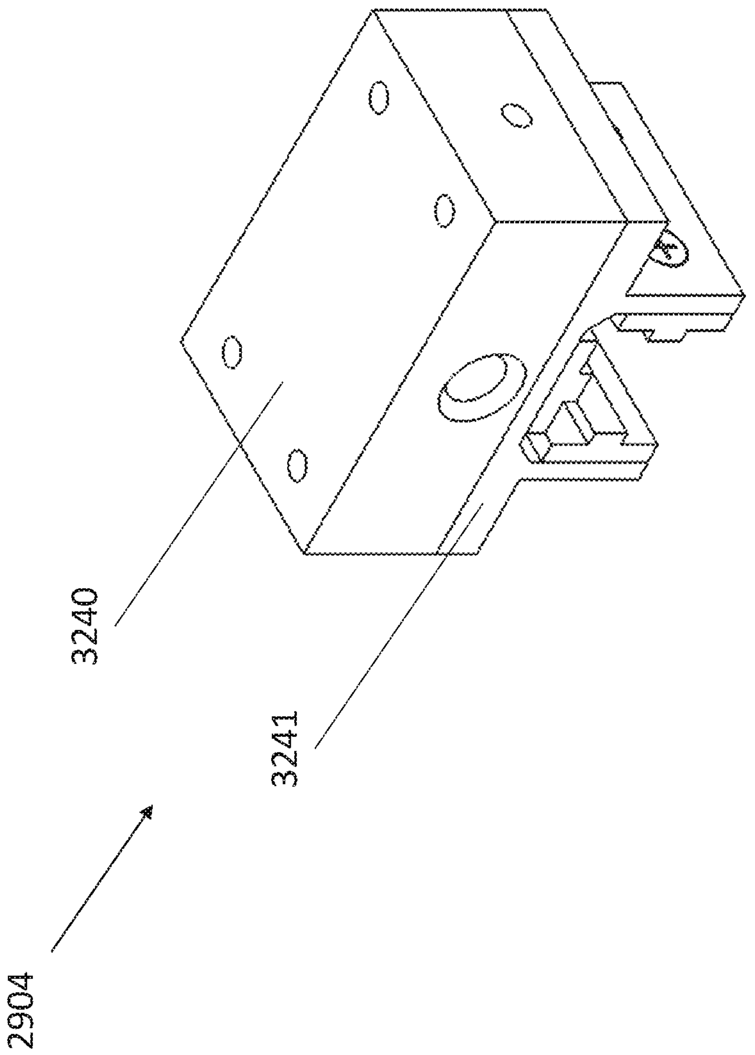
FIG. 32 shows a isometric view of a sliding platform on the platform of FIGS. 29A and 29B.

Referring now to the isometric view of FIG. 32, a detailed view of platform type 2904 is shown. The platform 2904 comprises a mounted block 3240 positioned on a linear slider 3241.

Alternative Catheter Embodiment

Figures 33A, 33B, 33C:
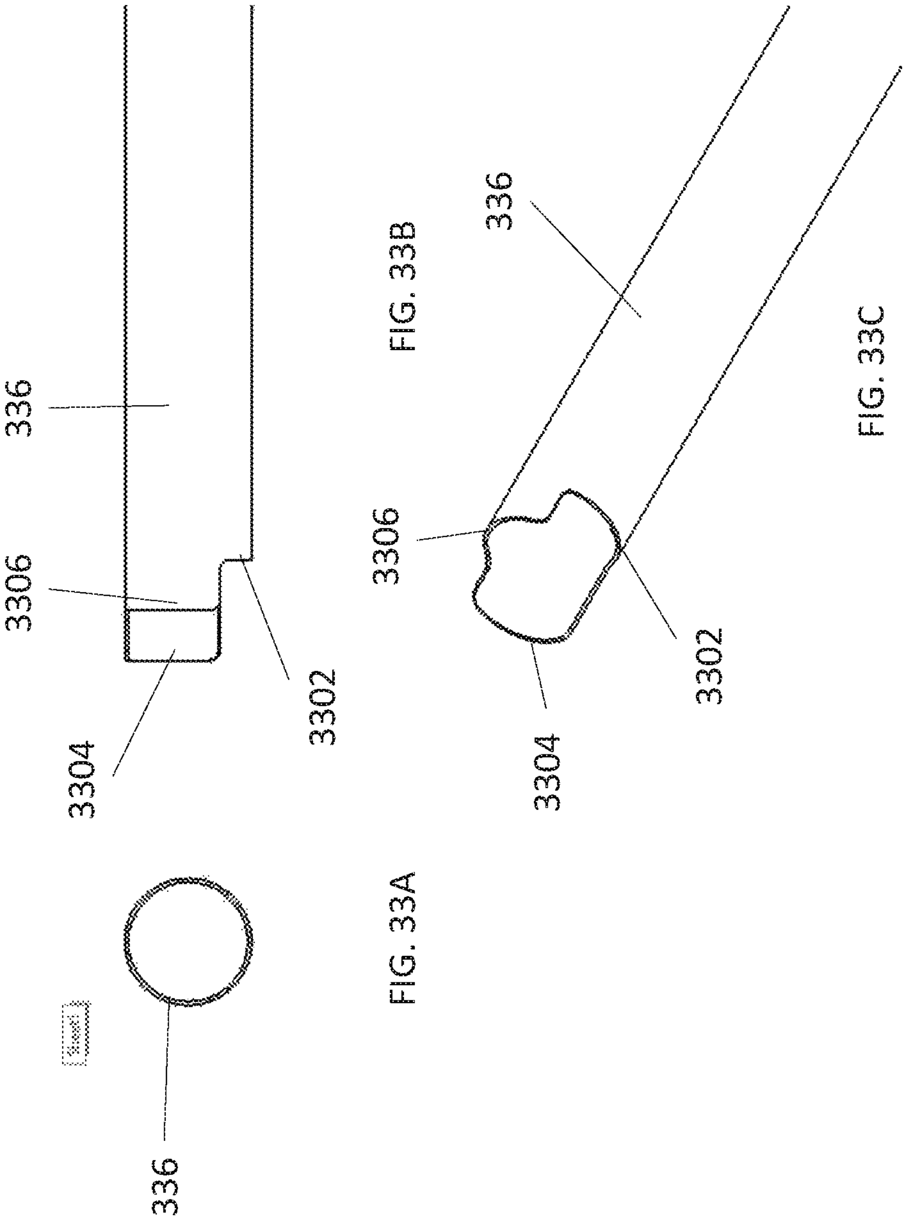
FIG. 33A shows an end view of an embodiment of a catheter with a stepped distal end.
FIG. 33B shows a side view of the catheter of FIG. 33A.
FIG. 33C shows a perspective view of the catheter of FIG. 33A.

In some embodiments, a distal end of the catheter can be configured to deploy the arms of a valve support device (e.g., device 500, 700, 1800) one at a time. FIGS. 33A-33C show front, side, and isometric views, respectively of a catheter configured to deploy the arms in such a manner. The distal end of the catheter 336 comprises three end surfaces. Surface 3302 is the proximal most surface at the distal end. Surface 3304 is the distal most surface at the distal end. Surface 3306 is positioned between surface 3304 and 3302.

Figure 34B:
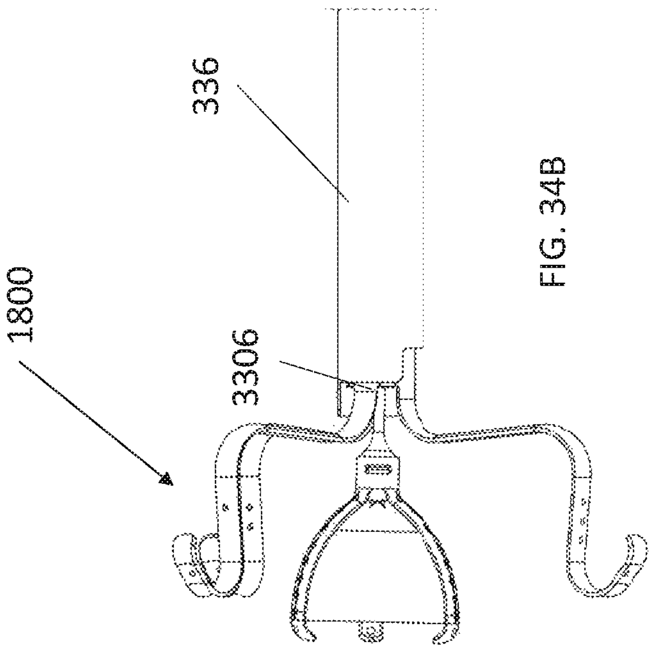
FIGS. 34A-34C show an exemplary device being deployed from the catheter of FIGS. 33A-33C.
Figure 34A:
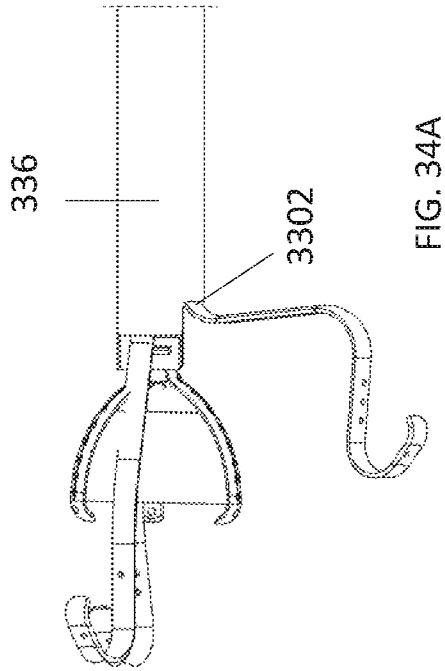
Figure 34C:
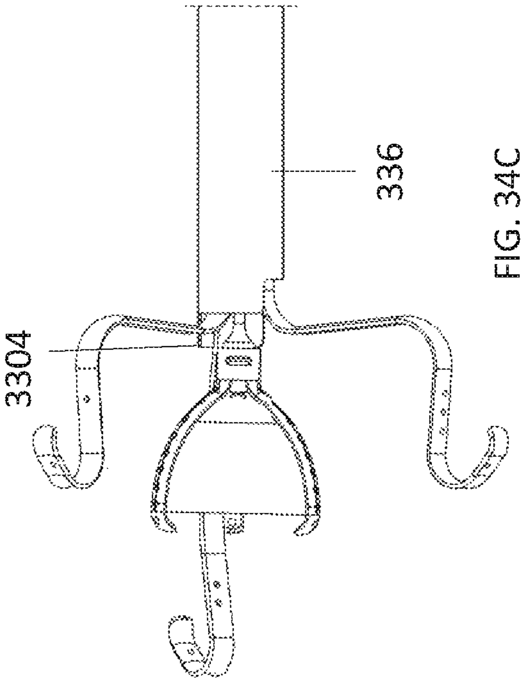

FIGS. 34A-34C show a device 1800 being deployed using the catheter of FIGS. 33A-33C. The device arm positioned against a portion of the catheter near the proximal most surface 3302 will be the first arm to be exposed and begin to expand as the catheter is retracted during device delivery, as shown in FIG. 34A. Referring to FIG. 34B, the device arm positioned against a portion of the catheter near surface 3306 will be the next arm to be exposed and begin to expand as the catheter is retracted during device delivery. Finally, as shown in FIG. 34C, the device arm positioned against a portion of the catheter near distal most surface 3304 will be the last arm to be exposed and begin to expand as the catheter is retracted during device delivery.

The configuration of the distal end of the catheter can be selected so that it is appropriate for the desired delivery. For example, in some embodiments, the configuration of the distal end can be adjusted to allow two arms to be deployed at the same time. The distal end can be adjusted so that there is a longer or shorter distance between the various distal surfaces, resulting in a longer or shorter time between deployment of the corresponding arms. The position of the varying surfaces can be configured to correspond to the annular placement of the arms.

Device for Pre-Operative Alignment of Arms

Figures 35A, 35B, 35C:
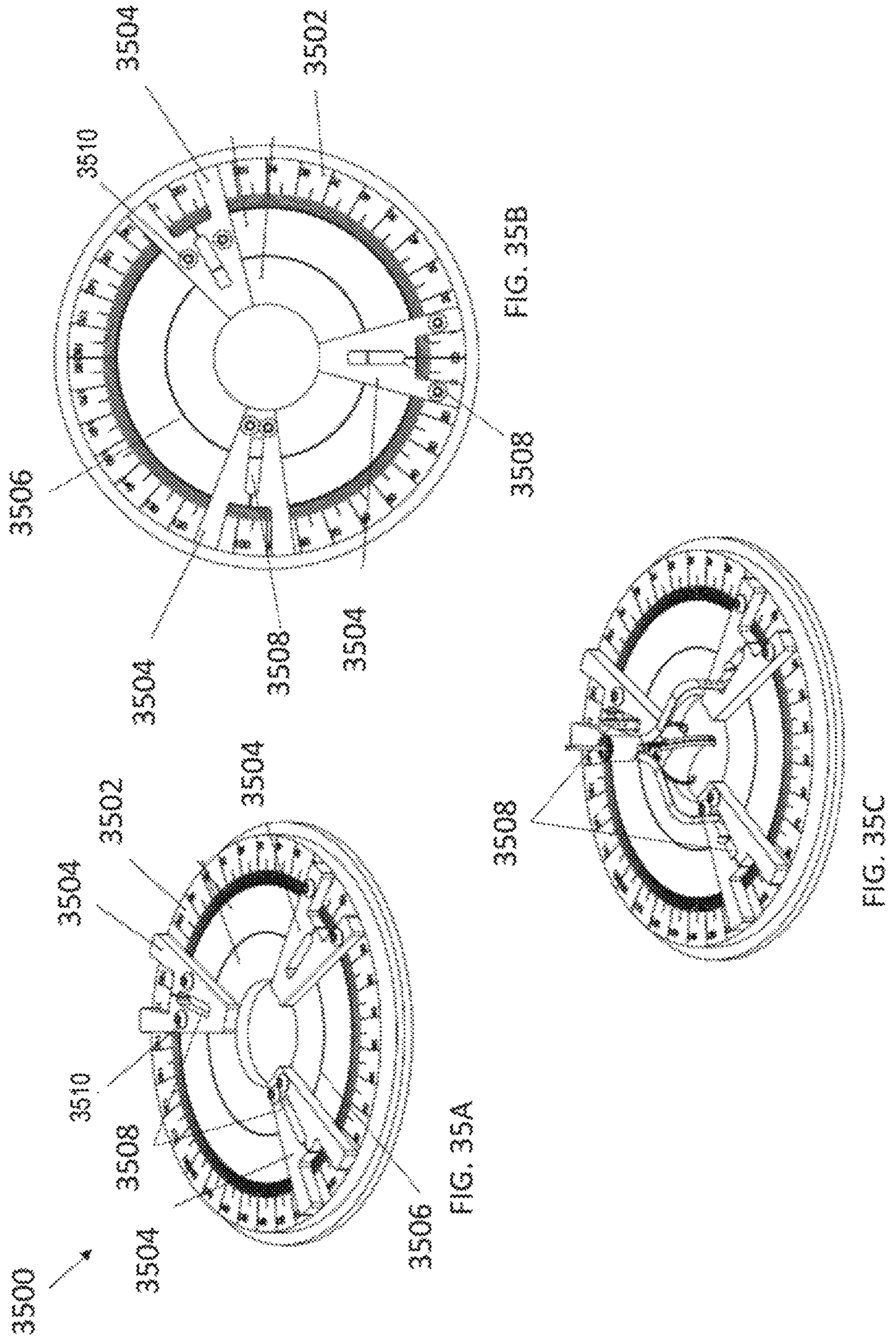
FIG. 35A shows a perspective view of an embodiment of an alignment device.
FIG. 35B shows a top view of the device of FIG. 35A
FIG. 35C shows a perspective view of an embodiment of a valve support device with its arms positioned within the device of FIGS. 35A and 35B.

In some embodiments, the anchoring arms of a valve support device (e.g., device 500, 700, 1800), can be pre-operatively placed in the proper rotational orientation. Pre-operative imaging (e.g., CT scan) can be used to determine how the arms should be placed. Referring to FIGS. 35A and 35B a top perspective and top view of an embodiment of an orienting device 3500 are shown. The device comprises a base 3502. The device 3500 comprises three sliders 3504 configured to slide around a circular track 3506 on base 3502. Angle markings are provided around the circular track, similar to a protractor. Each slider 3504 comprises a slot 3508. As shown in FIG. 35C, each slot 3508 can receive an arm of a valve support device. The sliders can be adjusted to place the arms in the desired configuration.

Referring to FIGS. 43 and 44A-C another embodiment of a delivery system 4300 is shown. Unless otherwise described, the system may comprise components, features, and functionality like that described with respect to other systems described herein (e.g., delivery system 1900, 2400). The delivery system comprises a sheath control section 600 positioned at a distal portion of the delivery system. The handle comprises an implant delivery control section 300 and a height and rotation adjustment member control section 2404.

The delivery system is positioned on a platform 4700 comprising a rail 2408 along which the various control sections of the handle may be translated. The platform 4700 is described in greater detail below.

Figure 44A:
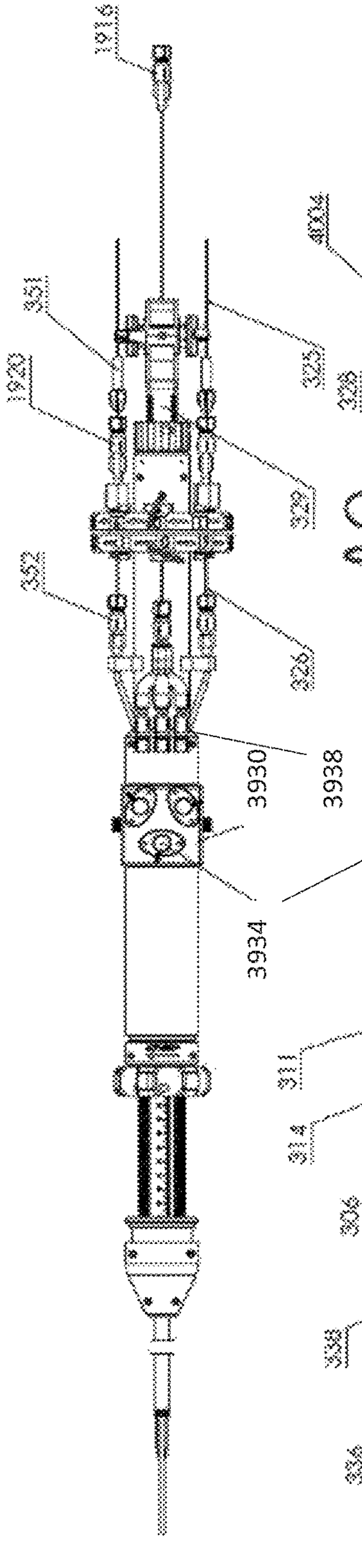
FIGS. 44A-44C show various views of the delivery system of FIG. 43.
Figure 44B:
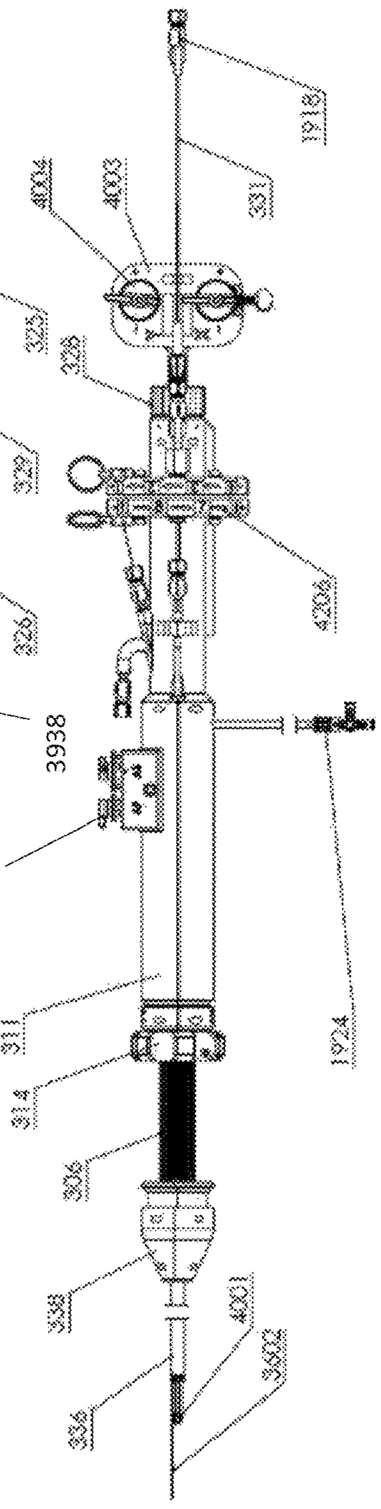
Figure 44C:
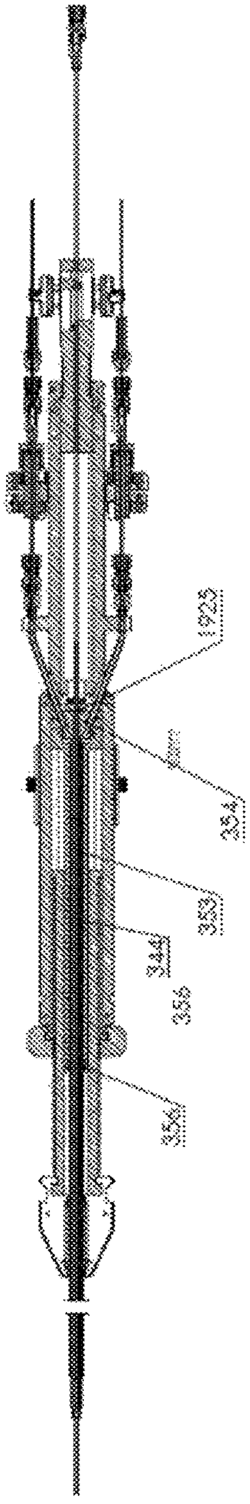

Referring now to FIGS. 44A-44C, a top view, side view, and top cutaway view, respectively of the delivery system 4300 are shown. The loop delivery shaft 3602 is shown extending from a distal portion of the handle. A distal section 336 of the catheter is also shown.

A knob 314 is shown at a proximal end of an unsheathing screw 306. The knob 314 can be used to control the screw 306 to pull the proximal end of the handle distally. When the unsheathing screw 306 is in its distal most position, the catheter is fully retracted. The multi-lumen shaft of the catheter butts up against the implant and slowly pushes it out of the catheter. A rod 353 can help to stabilize the unsheathing screw 306 as it moves back and forth. The rod can comprise a seal 356 (e.g., O-ring) to allow sealing against the flow optimizer 336.

The handle comprises a proximal handle shell 311 and a distal handle shell 338.

Loop control system 3930 comprising knobs 3934 is positioned at a mid-portion of the handle. Loop ports 3938 are positioned proximally to the knobs 3934.

The flushing block 354 is positioned near the ports 3934. Flushing block 354 can comprise an injection port 1924. As described above, the block 354 comprises a series of seals 1925, 352 (e.g., hemostasis valve). These seals include a seal overlapping the adjustment member 323, seals overlapping the torqueing tubes 326 and seal 321, which can be an O-Ring seal. The crevices within the catheter, between the various tubes, wires, and other devices need to be flushed with saline to prevent air from getting expelled from the catheter and to prevent blood from collecting and coagulating within the catheter and getting expelled. Saline can be injected through injection port 1924 and can flush the crevices inside the multi-lumen shaft and the outside of the tubes.

The torqueing tube control knob 4206 is shown positioned proximally to the flushing block 354.

Torqueing tube guidewires 325 and torqueing tubes 326 extend proximally to the hemostasis valves 352. A rigid tube 351 is positioned at a proximal end of the torqueing tube 326 to allow manipulation thereof.

The tilt adjustment control section 4003 is positioned toward a proximal end of the system. Knobs 4004 allow for manipulation of the tilt ball of the implant, as described in greater detail below.

The delivery system comprises a hemostasis valve at an end of the adjustment member 331 that allows for flushing of the volume inside the adjustment member 331.

Figures 45A, 45B, 45C:
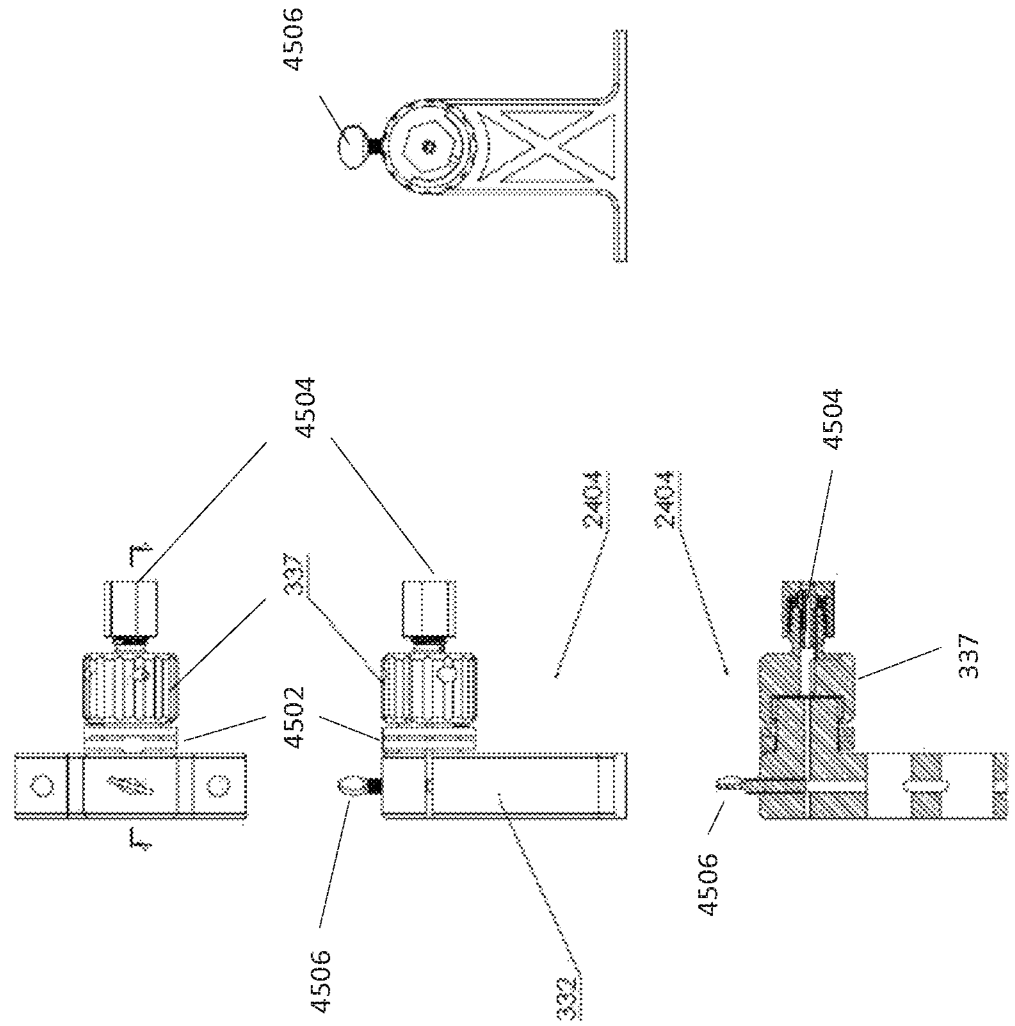

FIGS. 45A-45D show top, side, side cutaway, and back views of another embodiment of an adjustment member control section 2404. Unless otherwise described, the adjustment member control section comprises features similar to those described with respect to FIGS. 28A and 28B. The knob 337 comprises a collet 4504 on its end that locks down on the adjustment member 331 allowing rotation of the knob 337 to result in rotation of the adjustment member 331. The adjustment member control section can comprise a stop 4502 configured to limit the amount of rotation allowed by the knob 337. In some embodiments, a washer 4506 can be used to limit the rotation in a clockwise direction, and another washer can be used to limit the rotation in a counter-clockwise direction. FIG. 45D is a back view of the adjustment member control section 2404.

Figure 46A:
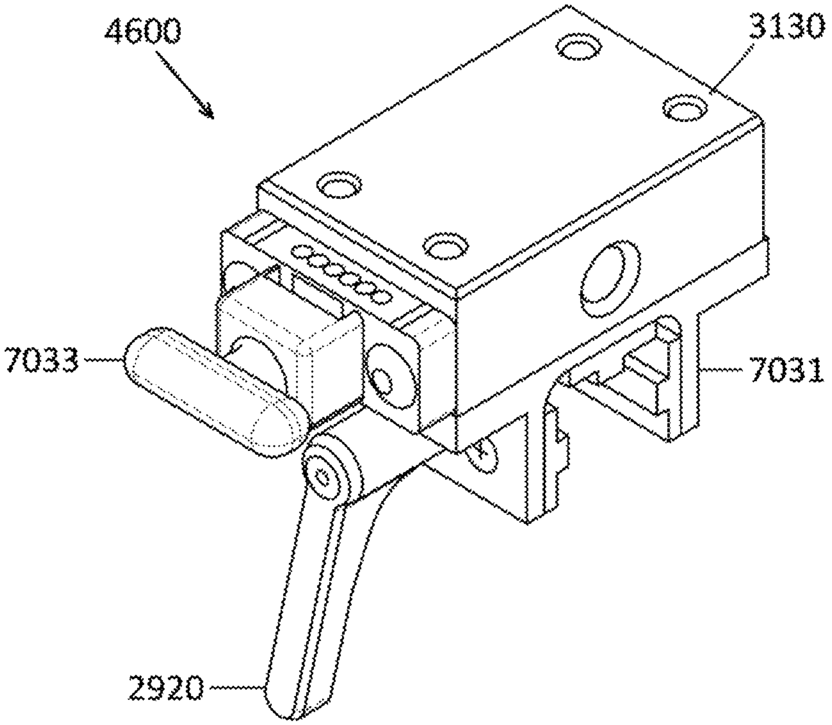
FIGS. 46A-46C show various views of an embodiment of a platform slider.
Figure 46B:
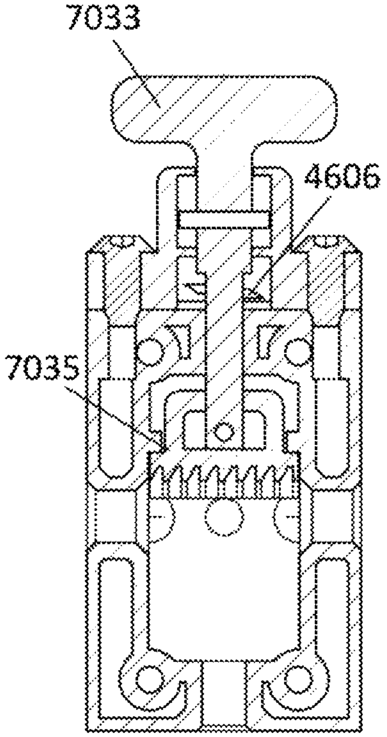
Figure 46C:
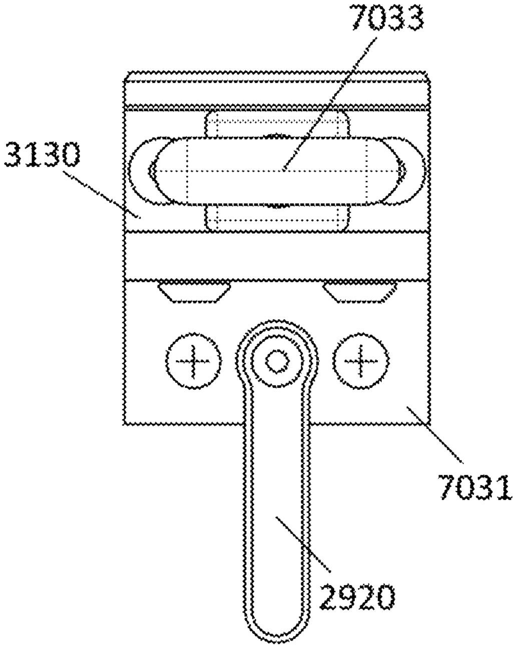

Referring to FIGS. 46A-46C, perspective, top cutaway and side views of another embodiment of a platform slider 4600 are shown. The platform comprises a mounting block 3130. The mounting block 3130 is positioned on a linear slider 7031 configured to slide along the platform rail. Crank 2920 is positioned on the slider and is configured to lock the slider 3131 to the rail, via a bolt which tightens 7031 to the platform rail. Knob 7033 can be used to engage or disengage the platform 4600 to the lead screw. As shown in the top section view of FIG. 46B, the platform comprises a lead screw connector 7035 resembling a half-nut. The knob 7033 can cause the connector 7035 to engage or disengage from the lead screw threads. A spring 4606 is below the knob 7033 and biases the knob 7033 to a disengaged position. The clinician must overcome this spring force to engage the connector with the lead screw. This helps to minimize the risk that the slider would inadvertently stay engaged from the lead screw and helps to ensure that the slider is truly disengaged when the knob is in the disengaged (e.g., vertical) position.

Figure 47A:
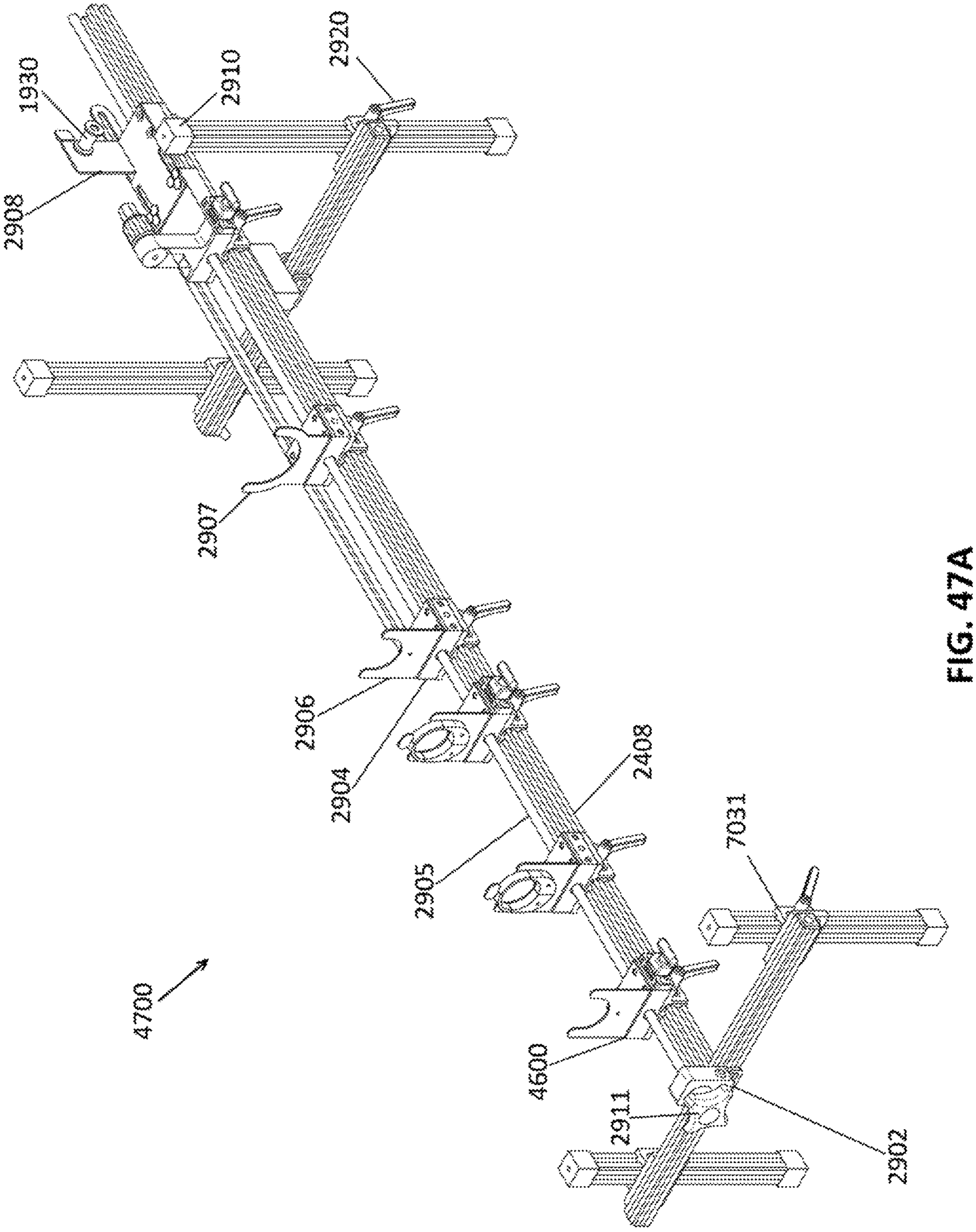
FIGS. 47A and 47B show various views of the platform of FIG. 43.
Figure 47B:
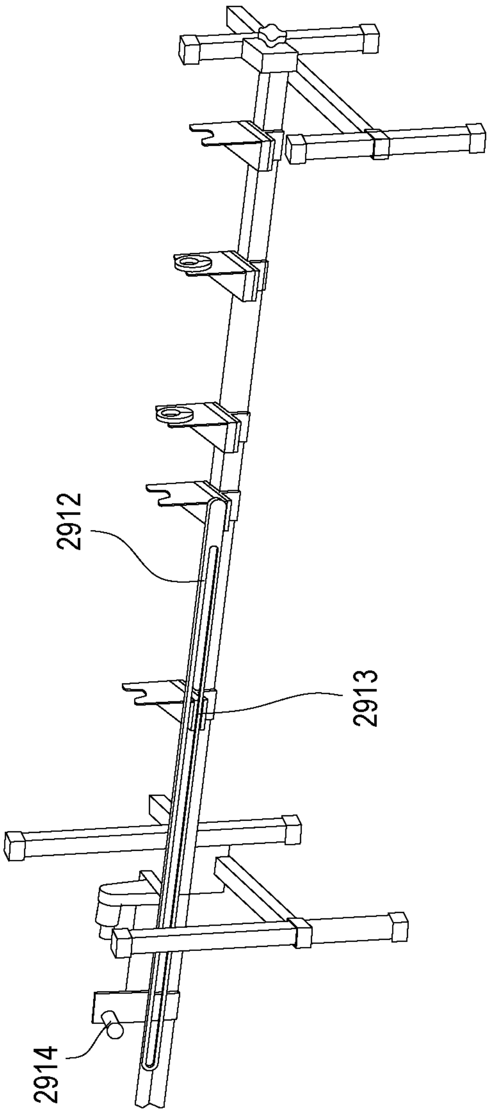

Referring now to FIGS. 47A and 47B, front and back perspective views of another embodiment of a platform 4700 are shown. Unless described otherwise, platform 4700 can comprise features, components, and functionalities similar to that of platform 2402 shown in FIGS. 29A and 29B. Platform 4700 comprises a rail 2408 along which sliders 4600 are configured to translate. In some embodiments, the rail 2408 comprises a T-slot type rail (e.g., T-slot aluminum extrusion). Positioned on the rail are a distal lead screw block 2902 and a proximal lead screw block 2910. The lead screw blocks 2902 can be configured to support the lead screw at or near each end of the lead screw. Positioned on the proximal lead screw block 2910 can be a lead screw crank 2911 configured to allow translation manipulation of the lead screw. Other control mechanisms are also contemplated (e.g., knob).

FIGS. 47A and 47B show two types of platforms for riding along the rail and holding various components of the handle. Control platform 4600 comprises a mechanism configured to engage or disengage from the lead screw, as described above with respect to FIGS. 46A-46C, allowing precise control over its translation along the rail 2408. The control platform may also comprise a locking mechanism configured to lock or unlock the platform 4600 to the rail 2408. Crank 2920 can be used to control the locking mechanism. A support platform 2904 can be configured to lock and unlock from the rail 2408 (e.g., as shown with respect to platform 4600).

The control platform(s) can comprise a standoff 2906 comprising a circular cutout shaped to mate with a reciprocal cutout on the handle (e.g., on collar 334). The support platform can also comprise a standoff 2907 comprising a circular cutout shaped to mate with a reciprocal cutout on the handle. The standoff 2907 may also comprise a cutout (e.g., square cutout) for preventing rotation relative to the collar 334. The collar can comprise a corresponding tab configured to (e.g., shaped to) mate with the cutout. Each component of the handle (e.g., sheath control section, catheter and tilt adjustment member control section, adjustment member control section) can be supported and controlled by a control type platform and a support type platform. It will be appreciated that the various components of each type of platforms may be combined and rearranged into different configurations achieving the same functionality.

Spool support 2908 is shown positioned on a proximal platform. Spool 1930 is positioned on the spool support. As shown in FIG. 47B, peg 2914 is operatively connected to the spool 1930. The peg 2914 is configured to turn the spool 1930. In some embodiments, the spool can use a worm gear so that it cannot be driven back. In other words, the spool will not spin under the force of the wire pulling on it.

As shown in FIG. 47B, connector 2912 extends between the shaft control section 2404 and the catheter and tilt adjustment member control section 300. This connector 2912 can be used to control the location of the two control sections with respect to one another. Knob 2913 can be used for fixing the location of one or both control sections.

The rail 2408 is supported by distal beam 4710 and proximal beam 4712. The beams are supported by legs 4714. A connector 4716 configured to slide or translate along the legs 4714 connects the beams 4710, 4712 to the legs 4714. The crank 2920 can be used to unlock the beam from the leg and allow translation. Once the clinician is satisfied with the position, the crank 2920 can be used to lock the beam onto the leg.

While the beams may generally be maneuvered evenly up and down the leg, each connector may be individually controllable, allowing precise control over the position of the delivery system.

Figure 48C:
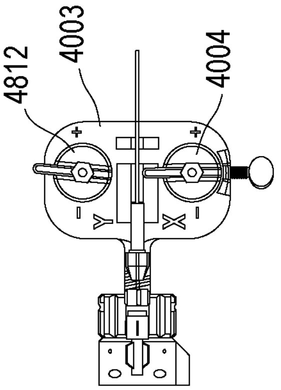
FIG. 48C shows an embodiment of a control for the tilt ball mechanism of FIGS. 48A and 48B.
Figure 48B:
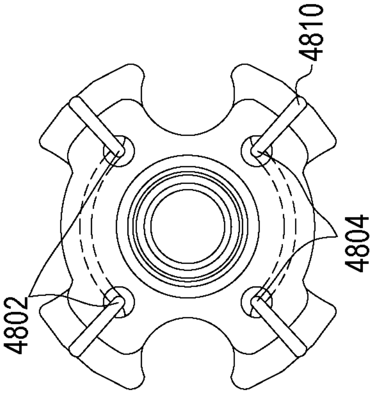
FIGS. 48A-48B show various views of an embodiment of a tilt ball mechanism.
Figure 48A:
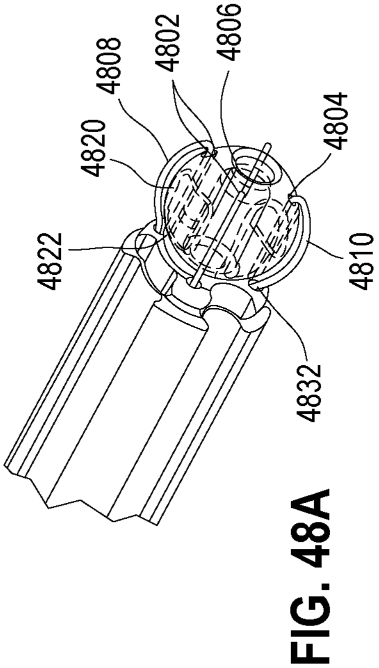

FIGS. 48A-48C show a distal end perspective view, distal end front view, and proximal control section, respectively, of another embodiment of a tilt mechanism for tilting the flow optimizer. As shown in FIGS. 48A and 48B, the ball of the device (e.g., similar to ball 771, 1671) comprises a plurality of apertures. One or more wires can be looped through the apertures in such a manner as to allow the ball to be tilted, thereby tilting the device.

The ball can be positioned towards a distal end of the multi-lumen shaft. The ball comprises a lumen through which the flexible member (e.g., flexible member 331) extends. Thus, tilting of the ball results in tilting of the flexible member, which can result in tilting of the device shaft.

It will be appreciated that the ball need not be an actual sphere, but can be any rotation member capable of being tilted using the tilt loops described herein.

FIGS. 48A and 48B shows a first and a second top aperture 4802 and a first and a second bottom aperture 4804. The apertures are positioned generally equidistant on a surface of the ball 4806 around a longitudinal axis of the delivery catheter. The apertures can be so positioned within a distal half or portion of the ball.

Top and bottom exit apertures 4822, 4832 can also be positioned generally equidistant on the ball around a longitudinal axis of the catheter. The apertures can be so positioned within a proximal half or portion of the ball.

A top wire loop 4808 extends distally along the delivery system towards the ball 4806, runs along an exterior portion of the ball, and enters a first top aperture 4802. From there the loop 4808 extends proximally along a top ball channel 4820 to a proximal portion of the ball and exits the ball through a top exit aperture 4822. The wire loop 4808 extends across to a second top exit aperture 4822 and is again inserted into the ball. The loop 4808 extends along a second top ball channel 4820 and exits the ball at a second top aperture 4802. From there the loop 4808 extends proximally towards a tilt control portion of the handle.

A bottom wire loop 4810 extends distally from the tilt control portion of the handle towards the ball 4806, runs along an exterior portion of the ball, and enters a first bottom aperture 4804. From there the loop 4808 extends proximally along a bottom ball channel 4830 to a proximal portion of the ball and exits the ball through a bottom exit aperture 4832. The wire loop 4810 extends across to a second bottom exit aperture 4832 and is again inserted into the ball. The loop 4810 extends along a second bottom ball channel 4830 and exits the ball at a second bottom aperture 4804. From there the loop 4808 extends proximally towards the tilt control portion of the handle.

Each end of the wire loop runs back to the knobs 4812, 4814 shown on tilt control manifold 4003. The top wire loop 4808 extends proximally with one end connecting to the top knob 4812 and the other end connecting to a corresponding top knob on the other side of the handle (not shown). The bottom wire loop 4810 extends proximally with one end connecting to the bottom knob 4004 and the other end connecting to a corresponding bottom knob on the other side of the handle (not shown). Controlling the tension on each end of the wire loops 4808, 4810 allows for tilting the ball, and thereby the device shaft, 0 to 90° in all directions.

Figure 49A:
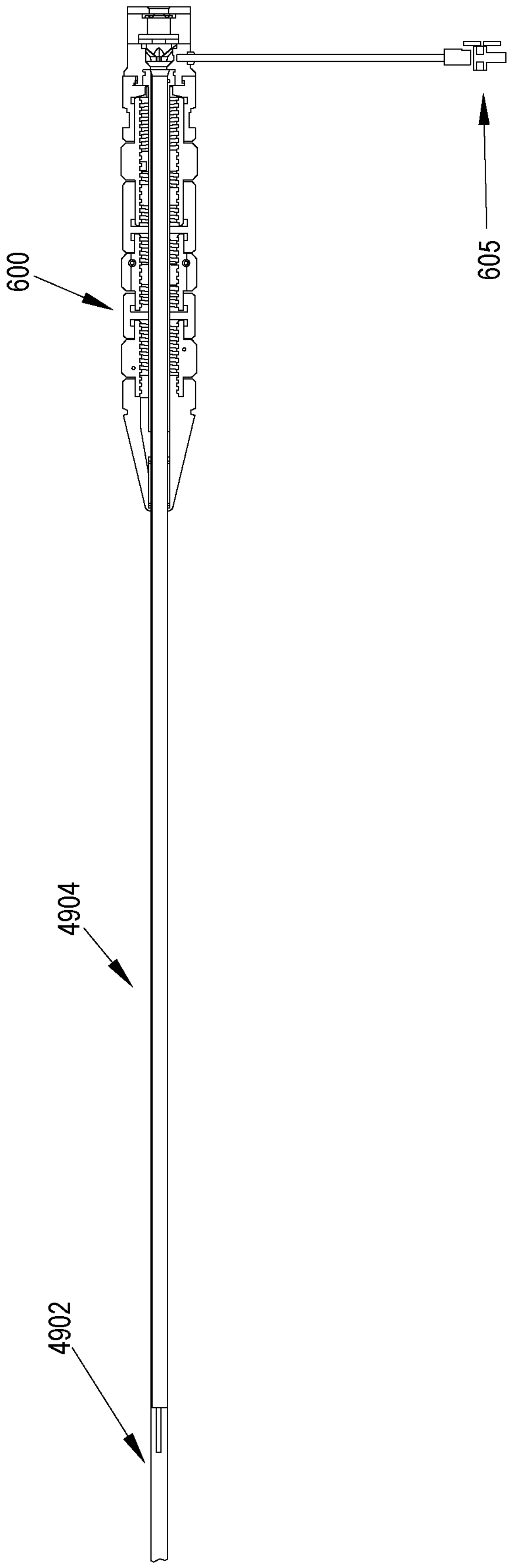
FIGS. 49A-49D show various views of an embodiment of a steerable catheter.

Referring to FIGS. 49A-52D, various aspects of another embodiment of a steerable catheter 4900 are provided. FIG. 49A shows the steerable catheter extending from the handle. A portion of the handle comprising the steerable catheter controls 600 is also shown. A stop cock 605 extends from the handle.

The steerable catheter comprises a distal deflector section 4902 and a steerable shaft 4904.

Figure 49B:
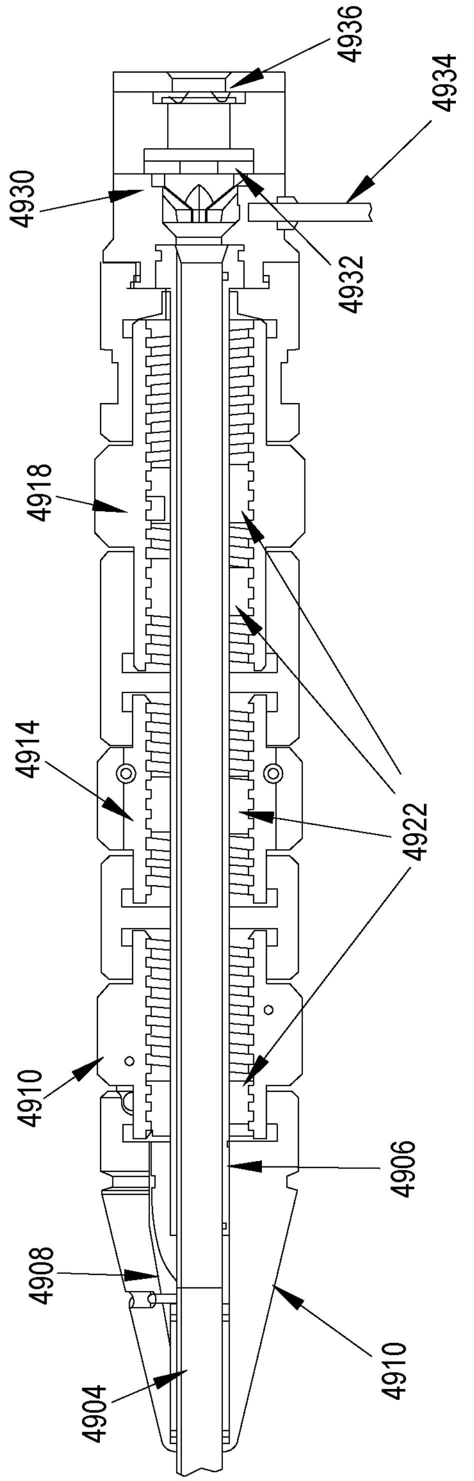

Moving to FIG. 49B, the handle controls 600 are shown in greater detail. The steerable shaft 4904 is shown extending through the handle. The pull wire(s) 4908 exit the steerable shaft at a distal portion of the handle and extend proximally towards control knobs. A rail 4906 extends along the handle, surrounding the steerable shaft lumen. Various deflector screws 4922 are positioned along the rail Various control knobs are positioned along rail. Translation of the control knobs results in tensioning or relaxing the corresponding pull wires.

A distal deflection knob 4910 is positioned towards a distal portion of the rail and is configured to control deflection of a distal section 4912 of the distal section of the steerable catheter. A height deflection knob 4914 is positioned proximally to the distal deflection knob 4910 and is configured to control deflection of a midportion 4916 of the distal section of the steerable catheter. A lateral deflection knob 4918 is positioned proximally to the height deflection knob 4914 and is configured to control deflection of a proximal portion 4920 of the distal section of the steerable catheter.

The handle further comprises a handle shell portion 4910.

A hemostasis hub 4930 is positioned towards a proximal end of the steerable catheter. The hemostasis hub 4930 comprises a valve 4932 (e.g., two layer crossing valve), a flushing tube 4934, and a backup valve 4936. Further details of the hemostasis hub are provided below.

Figure 49C:
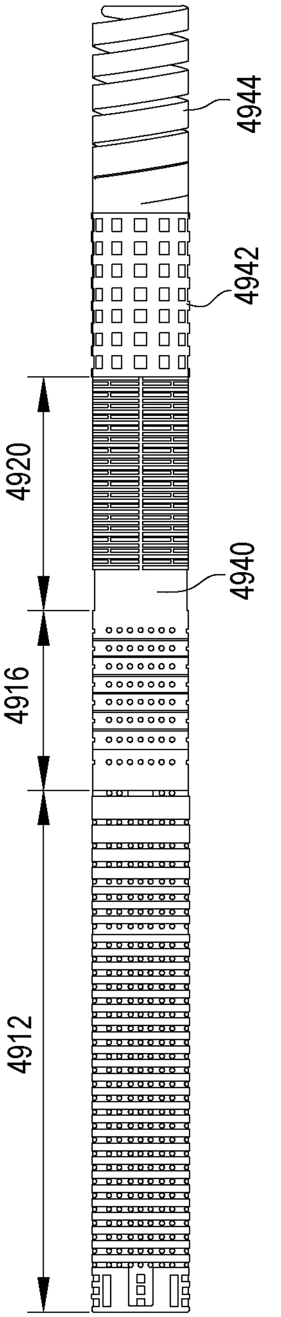
Figure 50A:
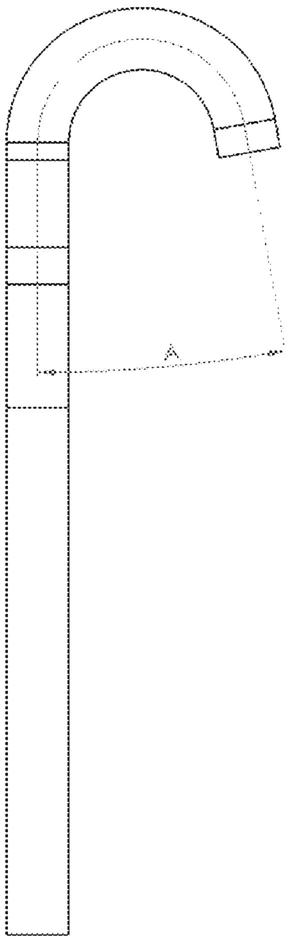
FIGS. 50A-52D show bending capabilities of various portions of the steerable catheter of FIGS. 49A-49D.
Figure 50B:
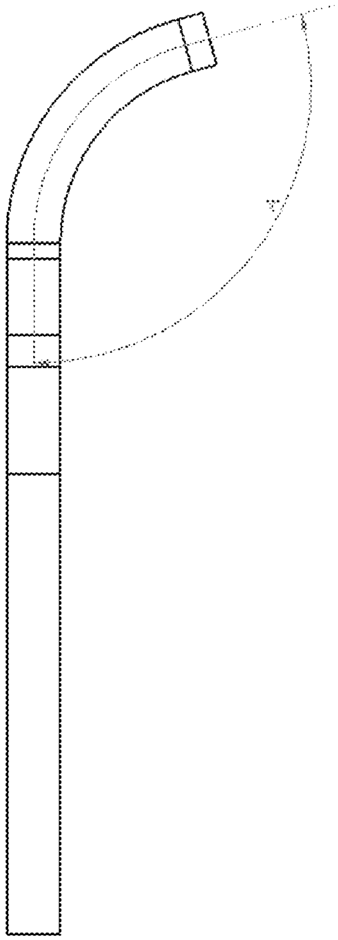

FIG. 49C shows an embodiment of a distal section 4902 of the steerable catheter. The distal portion 4912 is positioned at a distal end of the distal section. As shown in FIGS. 50A and 50B, the distal portion 4912 can be configured to deflect to an angle A from about 0-200°

In some embodiments, the distal portion 4912 comprises a length of about 40-70 mm (or about 50-60 mm, 45-65 mm, 55 mm, less than 40 mm, greater than 70 mm, etc.).

Figure 51A:
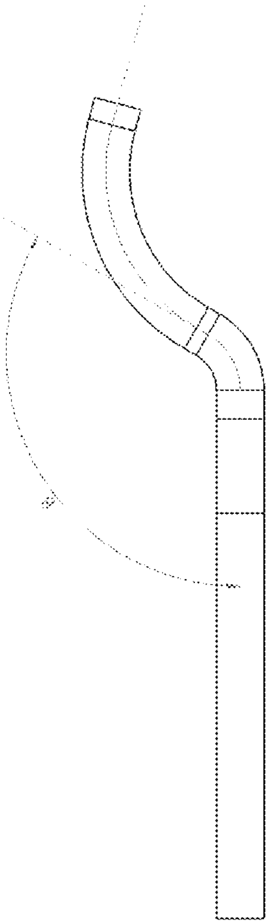
Figure 51B:
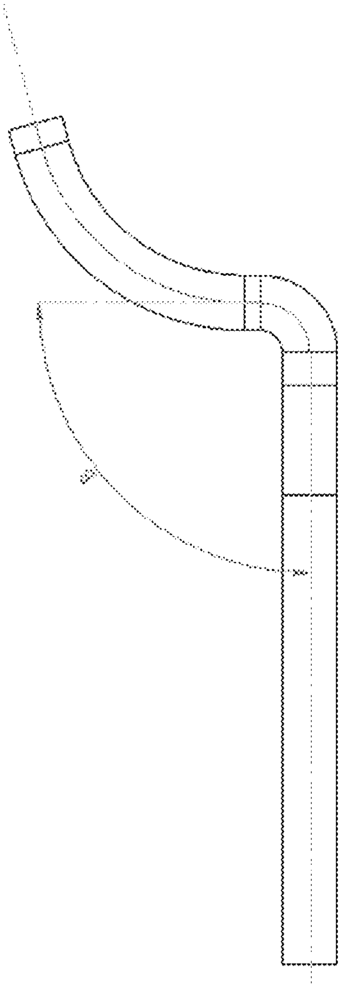
Figure 52C:
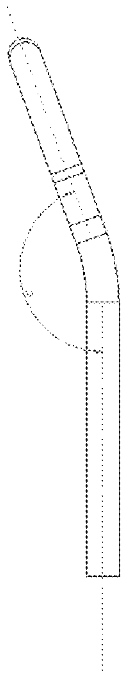
Figure 52D:
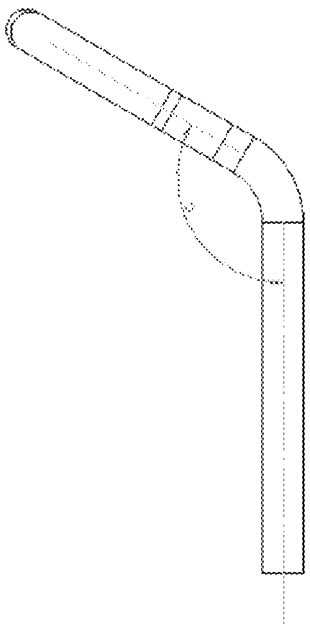
Figure 52A:
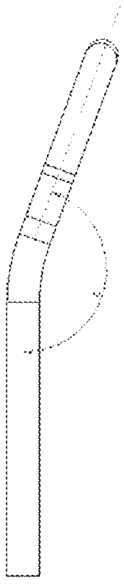
Figure 52B:
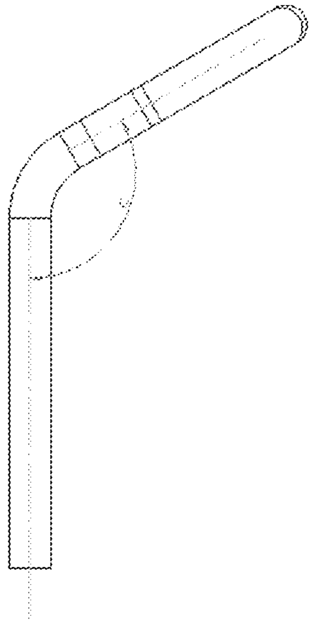

Referring back to FIG. 49C, the midportion 4916 of the distal section 4902 of the steerable catheter is positioned proximally to the distal portion 4912. As shown in FIGS. 51A and 51B, the mid portion 4916 can be configured to deflect to an angle B from about 0-90°.

In some embodiments, the midportion 4916 comprises a length of about 15-30 mm (or about 20-25 mm, 21-24 mm, less than 15 mm, greater than 30 mm, etc.).

Referring back to FIG. 49C, the proximal portion 4920 of the distal section 2902 of the steerable catheter is positioned proximally to the midportion 4916. As shown in FIGS. 52A-D, the proximal portion 4920 can be configured to allow lateral deflection (e.g., in either direction) to an angle C of about 0-90° in either direction.

In some embodiments, the length of the proximal portion 4920 is about 15-40 mm (or about 20-35 mm, or about 25-30 mm, greater than 40 mm, less than 15 mm, etc.).

The configuration of the distal portion, midportion, and proximal portions can allow the steerable catheter to navigate to the tricuspid valve of a patient.

Referring back to FIG. 49C, the distal section 2902 comprises a pull wire fixed point 4940.

The distal section 2902 comprises a lamination joining pattern portion 4942.

The distal section 2902 comprises a compression strain relief portion 4944.

Figure 49D:
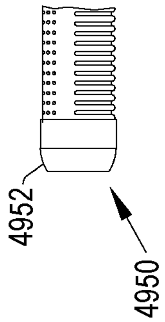

FIG. 49D shows a distal end of the distal section 2902 comprising an atraumatic tip 4950 on the end of the steerable catheter. This atraumatic tip comprises a tapered surface 4952, tapering towards the distal end of the catheter. This configuration can be designed to maintain coaxiality of the delivery catheter within the steerable catheter even during deflection of the steerable catheter (e.g., while at a maximum bend of the steerable deflector). This ensures and aids in positioning the implant coaxial to the tricuspid annulus during the procedure and reduces the risk in the system.

In some embodiments, the steerable tip is radiopaque and visible under fluoroscopy to assist in identifying catheter position and location relative to the anatomy and the other components of the delivery system.

Figure 53:
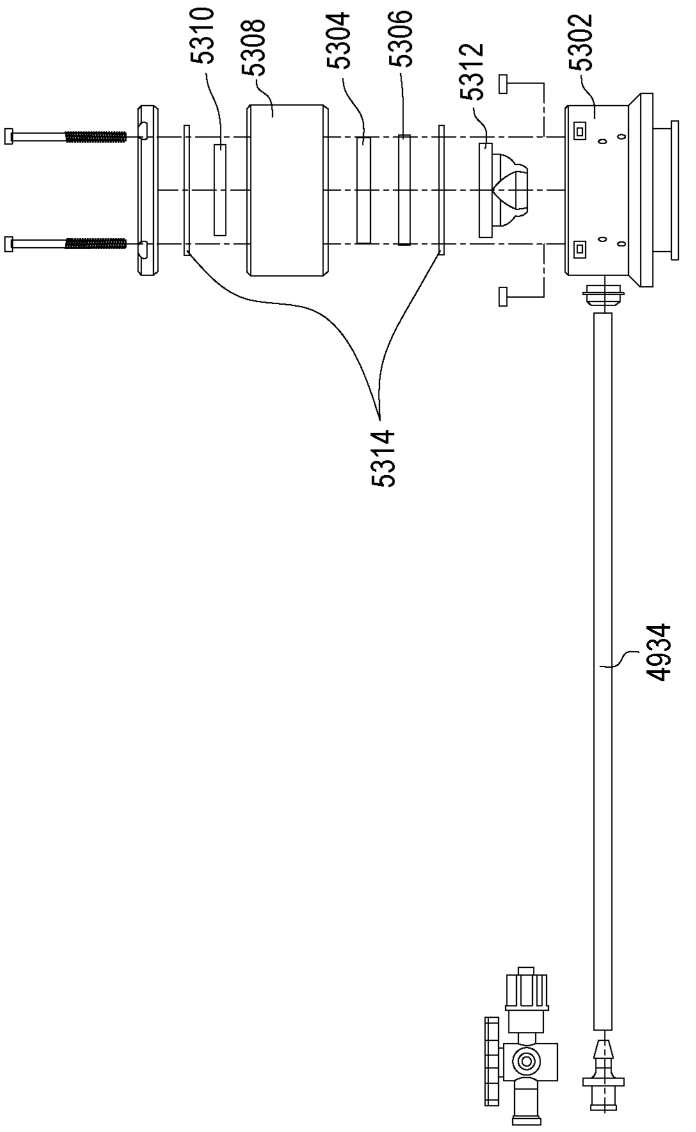
FIG. 53 shows an exploded view of an embodiment of a hemostasis hub.

FIG. 53 shows an exploded view of an embodiment of a hemostasis hub 4930 like that described with respect to FIG. 49B. The hemostasis hub can allow a clinician to maintain hemostasis during insertion and removal of catheter.

The hemostasis hub comprises a hemostasis hub housing 5302. The hub housing comprises a flushing tube 4934. The housing contains seals 5312 (e.g., duckbill valve), 5306 and 5304 and provides the ability to aspirate via flush port 4934 any air contained within the steerable catheter shaft and without introducing external air.

The hub comprises a cross slit valve 5304. The cross slit valves can help to provide a hemostatic seal after the clinician has removed the dilator from the catheter. The valve 5306 (e.g., cross-slit valve) can be positioned adjacent to a cross slit valve 5304 and be configured to assist valve coaptation.

A midplate 5308 houses a backup seal and additional valve 5310 (e.g. silicone seal with opening for passage of shaft). This portion can help prevent air from entering and blood from escaping.

The hemostasis hub can comprise one or more O-rings 5314 to ensure proper sealing.

Figure 54B:
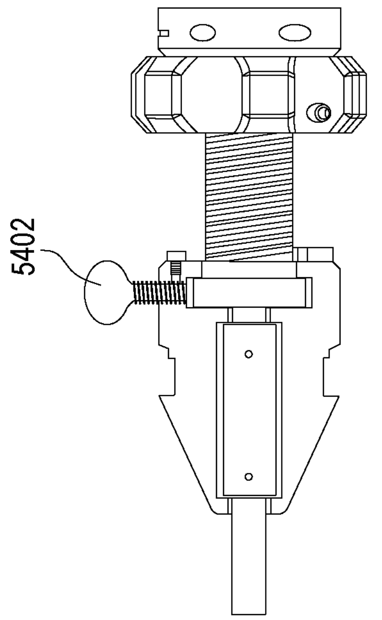
FIGS. 54A-54C show various views of an embodiment of a rotational control portion for the valve support device.
Figure 54A:
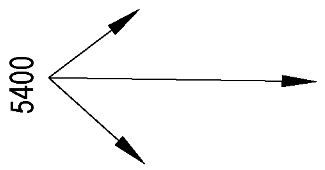
Figure 54A:
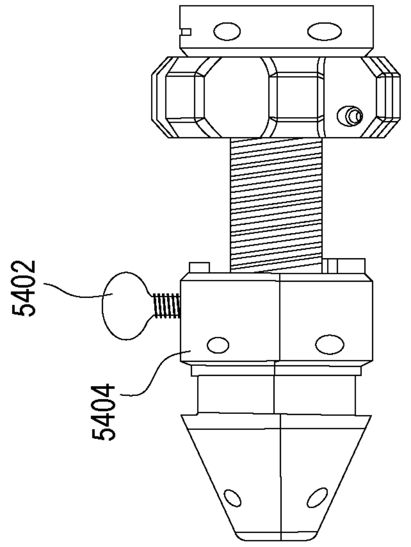
Figure 54C:
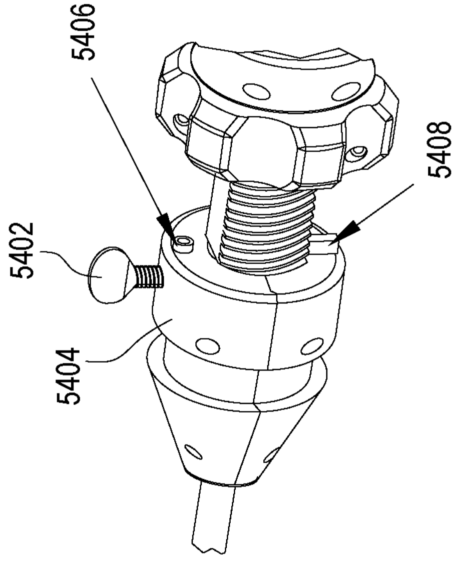

Referring now to FIGS. 54A-54C, side, side cutaway, and perspective views of an embodiment of a rotational control section 5400 are provided. A knob 5402 can be loosened to decouple the multi-lumen shaft from an outer surface of the delivery catheter. This decoupling allows the device to be rotated by rotating just the multi-lumen shaft instead of the whole delivery catheter. Rotating collar 5404 can allow for this rotation of the multi-lumen shaft and the device. Decoupling these components reduces frictional forces exerted during rotation and can allow for more precise rotational control.

The collar 5404 comprises a stop 5406 configured to interact with a stop 5408 on rod 5410 that limits rotation (e.g., up to +/−180°).

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method for positioning a device for assisting with functioning of a valve of a heart comprising:

advancing a flexible member through a delivery shaft until it butts up against a shaft of the device;

axially translating the flexible member, to adjust a height of a flow optimizer fixed to the shaft relative to an anchoring assembly of the device; and fixing the shaft to the anchoring assembly, thereby fixing the position of the flow optimizer relative to the shaft, further comprising retracting the delivery shaft to expose arms of the device.

2. The method of claim 1, further comprising expanding an arm of the device by loosening an arm loop, the arm loop extending through the delivery shaft to the device, looping around the arm, and returning to a loop control portion of a handle.

3. The method of claim 1, further comprising contracting an arm of the device by tightening an arm loop, the arm loop extending through the handle to the device, looping around the arm, and returning to a loop control portion of a handle.

4. The method of claim 1, further comprising navigating a steerable catheter through the catheter, the steerable catheter having a distal section comprising a distal portion, a midportion, and a proximal portion.

5. The method of claim 1, wherein fixing the shaft to the anchoring assembly comprises screwing a fastener into a ball joint connecting the anchoring assembly to the shaft, wherein screwing the fastener comprises advancing a torqueing tube through the delivery shaft and to the faster, further comprising engaging the torqueing tube to the fastener using an interference fit, further comprising locking the torqueing tube to the fastener by advancing an outer member over the engaged torqueing tube and fastener.

6. The method of claim 1, further comprising removing a wire connecting the handle to the device after confirming proper positioning of the device.

7. The method of claim 1, wherein the advancing and/or the axially translating is performed using a lead screw.

8. The method of claim 1, wherein the advancing and/or the axially translating comprises sliding one or more components along a rail.

9. A method for positioning a device for assisting with functioning of a valve of a heart comprising:

advancing a flexible member through a delivery shaft until it butts up against a shaft of the device;

axially translating the flexible member, to adjust a height of a flow optimizer fixed to the shaft relative to an anchoring assembly of the device; and fixing the shaft to the anchoring assembly, thereby fixing the position of the flow optimizer relative to the shaft, further comprising navigating a steerable catheter through the catheter, the steerable catheter having a distal section comprising a distal portion, a midportion, and a proximal portion, further comprising deflecting the distal portion in a first direction and amount, the midportion in a second direction and amount, and the proximal portion in a third direction and amount, wherein the first, second, and third directions and amounts are different from one another.

* * * * *